United States Patent
Min

(10) Patent No.: US 12,380,560 B2
(45) Date of Patent: Aug. 5, 2025

(54) SYSTEMS, METHODS, AND DEVICES FOR IMAGE-BASED PLAQUE ANALYSIS AND RISK DETERMINATION

(71) Applicant: Cleerly, Inc., Denver, CO (US)

(72) Inventor: James K. Min, Chapel Hill, NC (US)

(73) Assignee: Cleerly, Inc., Denver, CO (US)

( * ) Notice: Subject to any disclaimer, the term of this patent is extended or adjusted under 35 U.S.C. 154(b) by 0 days.

(21) Appl. No.: 18/674,711

(22) Filed: May 24, 2024

(65) Prior Publication Data

US 2024/0312018 A1     Sep. 19, 2024

Related U.S. Application Data

(63) Continuation of application No. 18/652,770, filed on May 1, 2024, which is a continuation-in-part of application No. 18/179,921, filed on Mar. 7, 2023.

(Continued)

(51) Int. Cl.
*G06T 7/00* (2017.01)
*A61B 6/00* (2024.01)

(Continued)

(52) U.S. Cl.
CPC ............ *G06T 7/0014* (2013.01); *A61B 6/027* (2013.01); *A61B 6/035* (2013.01); *A61B 6/4241* (2013.01);

(Continued)

(58) Field of Classification Search
CPC ......... G06T 7/0014; G06T 2207/10081; G06T 2207/30048; G06T 2207/30101;

(Continued)

(56) References Cited

U.S. PATENT DOCUMENTS

| 4,296,901 A | 10/1981 | Perrott |
| 4,945,478 A | 7/1990 | Merickel et al. |

(Continued)

FOREIGN PATENT DOCUMENTS

| AU | 2023200986 A1 | 3/2023 |
| CA | 2368390 A1 | 9/2000 |

(Continued)

OTHER PUBLICATIONS

US 11,791,027 B2, 10/2023, Buckler et al. (withdrawn)

(Continued)

*Primary Examiner* — Ross Varndell
(74) *Attorney, Agent, or Firm* — Perkins Coie LLP

(57) ABSTRACT

This application is directed to systems, methods, and devices for image based analysis of plaque. In some embodiments, the approaches herein can be used for developing treatment plans, which can include local treatment, systemic treatment, or both. In some embodiments, the approaches herein can be used for stent selection. In some embodiments, the approaches herein can be used for surgical planning, which can include robotic surgical planning. In some embodiments, the approaches herein can be used for image normalization. In some embodiments, the approaches herein can be used for identifying plaque calcification thresholds. In some embodiments, the approaches herein can be used for identifying thin cap fibroatheroma. In some embodiments, the approaches herein can be used for coronary artery tree reconstruction. Some embodiments are directed to coronary artery disease risk stratification.

18 Claims, 28 Drawing Sheets

Related U.S. Application Data

(60) Provisional application No. 63/557,396, filed on Feb. 23, 2024, provisional application No. 63/557,405, filed on Feb. 23, 2024, provisional application No. 63/557,401, filed on Feb. 23, 2024, provisional application No. 63/606,584, filed on Dec. 5, 2023, provisional application No. 63/597,528, filed on Nov. 9, 2023, provisional application No. 63/582,792, filed on Sep. 14, 2023, provisional application No. 63/519,220, filed on Aug. 11, 2023, provisional application No. 63/499,602, filed on May 2, 2023, provisional application No. 63/381,210, filed on Oct. 27, 2022, provisional application No. 63/368,293, filed on Jul. 13, 2022, provisional application No. 63/365,381, filed on May 26, 2022, provisional application No. 63/364,084, filed on May 3, 2022, provisional application No. 63/364,078, filed on May 3, 2022, provisional application No. 63/362,856, filed on Apr. 12, 2022, provisional application No. 63/362,108, filed on Mar. 29, 2022, provisional application No. 63/269,136, filed on Mar. 10, 2022.

(51) Int. Cl.
| | | |
|---|---|---|
| *A61B 6/02* | (2006.01) | |
| *A61B 6/03* | (2006.01) | |
| *A61B 6/42* | (2024.01) | |
| *A61B 6/50* | (2024.01) | |
| *G06T 5/60* | (2024.01) | |
| *G06T 7/62* | (2017.01) | |
| *G06V 10/766* | (2022.01) | |
| *G16H 30/40* | (2018.01) | |
| *G16H 50/30* | (2018.01) | |

(52) U.S. Cl.
CPC ............ *A61B 6/504* (2013.01); *A61B 6/5217* (2013.01); *G06T 5/60* (2024.01); *G06T 7/62* (2017.01); *G16H 30/40* (2018.01); *G16H 50/30* (2018.01); *G06T 2207/10081* (2013.01); *G06T 2207/20021* (2013.01); *G06T 2207/20081* (2013.01); *G06T 2207/20084* (2013.01); *G06T 2207/30048* (2013.01); *G06T 2207/30101* (2013.01); *G06V 10/766* (2022.01)

(58) Field of Classification Search
CPC ...... A61B 6/504; A61B 6/5217; G16H 30/40; G16H 50/30
See application file for complete search history.

(56) References Cited

U.S. PATENT DOCUMENTS

| | | | |
|---|---|---|---|
| 5,056,130 | A | 10/1991 | Engel |
| 5,722,408 | A | 3/1998 | Dehner et al. |
| 5,891,030 | A | 4/1999 | Johnson et al. |
| 5,944,689 | A | 8/1999 | Houser et al. |
| 6,047,080 | A | 4/2000 | Chen et al. |
| 6,320,931 | B1 | 11/2001 | Arnold |
| 6,591,004 | B1 | 7/2003 | Vanessen et al. |
| 6,993,382 | B2 | 1/2006 | Casscells et al. |
| 7,008,401 | B2 | 3/2006 | Thompson et al. |
| 7,011,655 | B2 | 3/2006 | Thompson et al. |
| 7,045,238 | B2 | 5/2006 | Gottmann et al. |
| 7,191,110 | B1 | 3/2007 | Charbel et al. |
| 7,276,044 | B2 | 10/2007 | Ferry et al. |
| 7,351,214 | B2 | 4/2008 | Burgermeister |
| 7,371,248 | B2 | 5/2008 | Dapolito et al. |
| 7,535,986 | B2 | 5/2009 | Hempel |
| 7,558,611 | B2 | 7/2009 | Arnold et al. |
| 7,570,983 | B2 | 8/2009 | Becker et al. |
| 7,705,490 | B2 | 4/2010 | Srinivasan et al. |
| 7,711,165 | B2 | 5/2010 | Lesage et al. |
| 7,715,626 | B2 | 5/2010 | Florin et al. |
| 7,766,856 | B2 | 8/2010 | Ferry et al. |
| 7,803,130 | B2 | 9/2010 | Ryan et al. |
| 7,805,385 | B2 | 9/2010 | Steck et al. |
| 7,813,549 | B2 | 10/2010 | Buelow et al. |
| 7,840,062 | B2 | 11/2010 | Boroczky et al. |
| 7,860,283 | B2 | 12/2010 | Begelman et al. |
| 7,876,939 | B2 | 1/2011 | Yankelevitz et al. |
| 7,899,764 | B2 | 3/2011 | Martin et al. |
| 7,904,977 | B1 | 3/2011 | Singh |
| 7,907,766 | B2 | 3/2011 | Lehel et al. |
| 7,912,528 | B2 | 3/2011 | Krishnan et al. |
| 7,940,974 | B2 | 5/2011 | Skinner et al. |
| 7,940,977 | B2 | 5/2011 | Begelman et al. |
| 7,953,266 | B2 | 5/2011 | Gulsun et al. |
| 7,974,681 | B2 | 7/2011 | Wallace et al. |
| 7,993,274 | B2 | 8/2011 | Pruvot et al. |
| 7,998,020 | B2 | 8/2011 | Kidd et al. |
| 8,009,793 | B2 | 8/2011 | Langheinrich et al. |
| 8,021,326 | B2 | 9/2011 | Moll et al. |
| 8,046,488 | B2 | 10/2011 | Cherukuri et al. |
| 8,068,894 | B2 | 11/2011 | Huizenga et al. |
| 8,107,695 | B2 | 1/2012 | Wollenweber |
| 8,108,069 | B2 | 1/2012 | Stahler et al. |
| 8,114,097 | B2 | 2/2012 | Brock et al. |
| 8,139,836 | B2 | 3/2012 | Arnold et al. |
| 8,144,949 | B2 | 3/2012 | Simon et al. |
| 8,186,880 | B1 | 5/2012 | Arnold |
| 8,200,466 | B2 | 6/2012 | Spilker et al. |
| 8,211,084 | B2 | 7/2012 | Kassab et al. |
| 8,257,302 | B2 | 9/2012 | Beyar et al. |
| 8,317,744 | B2 | 11/2012 | Kirschenman |
| 8,386,188 | B2 | 2/2013 | Taylor et al. |
| 8,390,438 | B2 | 3/2013 | Olson et al. |
| 8,460,236 | B2 | 6/2013 | Roelle et al. |
| 8,494,244 | B2 | 7/2013 | Dutta et al. |
| 8,526,699 | B2 | 9/2013 | Mittal et al. |
| 8,551,084 | B2 | 10/2013 | Hauck et al. |
| 8,582,854 | B2 | 11/2013 | Zhang et al. |
| 8,603,068 | B2 | 12/2013 | Weitzner et al. |
| 8,605,979 | B2 | 12/2013 | Arnold et al. |
| 8,615,288 | B2 | 12/2013 | Govari et al. |
| 8,660,326 | B2 | 2/2014 | Ohayon et al. |
| 8,684,953 | B2 | 4/2014 | Cabiri |
| 8,740,840 | B2 | 6/2014 | Foley et al. |
| 8,774,479 | B2 | 7/2014 | Madabhushi et al. |
| 8,777,854 | B2 | 7/2014 | Patwardhan et al. |
| 8,790,297 | B2 | 7/2014 | Bromander et al. |
| 8,867,822 | B2 | 10/2014 | Oh et al. |
| 8,885,905 | B2 | 11/2014 | Dey et al. |
| 8,938,106 | B2 | 1/2015 | Aulbach et al. |
| 9,005,217 | B2 | 4/2015 | Govari et al. |
| 9,008,392 | B1 | 4/2015 | Bai et al. |
| 9,058,692 | B1 | 6/2015 | Grady et al. |
| 9,066,740 | B2 | 6/2015 | Carlson et al. |
| 9,070,214 | B1 | 6/2015 | Grady et al. |
| 9,081,721 | B1 | 7/2015 | Grady et al. |
| 9,129,417 | B2 | 9/2015 | Zheng et al. |
| 9,138,566 | B2 | 9/2015 | Cabiri |
| 9,155,512 | B2 | 10/2015 | Choi et al. |
| 9,159,159 | B2 | 10/2015 | Bai et al. |
| 9,195,801 | B1 | 11/2015 | Sankaran et al. |
| 9,220,418 | B2 | 12/2015 | Choi et al. |
| 9,220,419 | B2 | 12/2015 | Choi et al. |
| 9,220,568 | B2 | 12/2015 | Bromander et al. |
| 9,235,887 | B2 | 1/2016 | Buckler et al. |
| 9,239,905 | B1 | 1/2016 | Sankaran et al. |
| 9,280,639 | B2 | 3/2016 | Sankaran et al. |
| 9,295,397 | B2 | 3/2016 | Liu et al. |
| 9,295,429 | B2 | 3/2016 | Ong et al. |
| 9,295,527 | B2 | 3/2016 | Kirschenman et al. |
| 9,320,573 | B2 | 4/2016 | Sandhu et al. |
| 9,333,324 | B2 | 5/2016 | Cohen et al. |
| 9,378,580 | B2 | 6/2016 | Grady et al. |
| 9,430,827 | B2 | 8/2016 | Kelm et al. |
| 9,538,925 | B2 | 1/2017 | Sharma et al. |
| 9,545,246 | B2 | 1/2017 | Lavender |
| 9,586,029 | B2 | 3/2017 | Shekalim et al. |

(56) References Cited

U.S. PATENT DOCUMENTS

| | | |
|---|---|---|
| 9,610,272 B2 | 4/2017 | Soni |
| 9,633,277 B2 | 4/2017 | Feldman et al. |
| 9,642,586 B2 | 5/2017 | Kelm et al. |
| 9,649,171 B2 | 5/2017 | Sankaran et al. |
| 9,655,563 B2 | 5/2017 | Liu et al. |
| 9,679,374 B2 | 6/2017 | Choi et al. |
| 9,700,219 B2 | 7/2017 | Sharma et al. |
| 9,715,562 B2 | 7/2017 | Goldstein et al. |
| 9,721,340 B2 | 8/2017 | Gillies et al. |
| 9,761,004 B2 | 9/2017 | Mittal et al. |
| 9,763,650 B2 | 9/2017 | Chen et al. |
| 9,767,557 B1 | 9/2017 | Gulsun et al. |
| 9,770,303 B2 | 9/2017 | Choi et al. |
| 9,785,748 B2 | 10/2017 | Koo et al. |
| 9,805,463 B2 | 10/2017 | Choi et al. |
| 9,805,470 B2 | 10/2017 | Bhatia et al. |
| 9,814,490 B2 | 11/2017 | Neoh et al. |
| 9,836,653 B2 | 12/2017 | Schnittman |
| 9,839,399 B2 | 12/2017 | Fonte et al. |
| 9,839,484 B2 | 12/2017 | Taylor |
| 9,881,372 B2 | 1/2018 | Gulsun et al. |
| 9,965,891 B2 | 5/2018 | Grady et al. |
| 9,980,960 B2 | 5/2018 | Chance |
| 10,010,255 B2 | 7/2018 | Fonte et al. |
| 10,010,700 B2 | 7/2018 | Romoscanu |
| 10,052,031 B2 | 8/2018 | Sharma et al. |
| 10,078,124 B2 | 9/2018 | Horkay et al. |
| 10,082,553 B2 | 9/2018 | Boss |
| 10,082,793 B1 | 9/2018 | Glaser |
| 10,130,242 B2 | 11/2018 | Ostrovsky et al. |
| 10,149,728 B2 | 12/2018 | Bencteux et al. |
| 10,170,206 B2 | 1/2019 | Koo et al. |
| 10,176,408 B2 | 1/2019 | Paik et al. |
| 10,307,131 B2 | 6/2019 | Taylor et al. |
| 10,352,411 B2 | 7/2019 | Fojtik |
| 10,354,360 B2 | 7/2019 | Sakamoto |
| 10,357,230 B2 | 7/2019 | Bolduc |
| 10,359,783 B2 | 7/2019 | Williams et al. |
| 10,398,331 B2 | 9/2019 | Relan et al. |
| 10,433,740 B2 | 10/2019 | Fonte et al. |
| 10,448,811 B2 | 10/2019 | London et al. |
| 10,451,409 B2 | 10/2019 | Tojo et al. |
| 10,453,191 B2 | 10/2019 | Shalev et al. |
| 10,456,094 B2 | 10/2019 | Fonte et al. |
| 10,456,556 B2 | 10/2019 | Cabiri |
| 10,463,835 B2 | 11/2019 | Jungles |
| 10,470,793 B2 | 11/2019 | McArthur et al. |
| 10,478,130 B2 | 11/2019 | Sharma et al. |
| 10,478,595 B2 | 11/2019 | Kokish |
| 10,483,006 B2 | 11/2019 | Itu et al. |
| 10,492,755 B2 | 12/2019 | Lin et al. |
| 10,498,755 B2 | 12/2019 | Harris et al. |
| 10,500,373 B2 | 12/2019 | Barrish et al. |
| 10,507,037 B2 | 12/2019 | Doud et al. |
| 10,517,677 B2 | 12/2019 | Sankaran et al. |
| 10,542,878 B2 | 1/2020 | Dewaele et al. |
| 10,549,071 B2 | 2/2020 | Falb et al. |
| 10,610,203 B2 | 4/2020 | Liang et al. |
| 10,632,287 B2 | 4/2020 | Romoscanu et al. |
| 10,667,673 B2 | 6/2020 | Su et al. |
| 10,695,023 B2 | 6/2020 | Antoniades et al. |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,740,880 B2 | 8/2020 | Paik et al. |
| 10,744,301 B2 | 8/2020 | Pacheco et al. |
| 10,755,810 B2 | 8/2020 | Buckler et al. |
| 10,762,624 B2 | 9/2020 | Daughton et al. |
| 10,776,988 B2 | 9/2020 | Grady et al. |
| 10,799,305 B2 | 10/2020 | Murphy et al. |
| 10,799,677 B2 | 10/2020 | Khuu et al. |
| 10,806,897 B2 | 10/2020 | Furnish |
| 10,813,612 B2 | 10/2020 | Min |
| 10,813,708 B2 | 10/2020 | Reinstein et al. |
| 10,828,468 B2 | 11/2020 | Selkee |
| 10,835,716 B2 | 11/2020 | Kim et al. |
| 10,871,536 B2 | 12/2020 | Golden et al. |
| 10,888,234 B2 | 1/2021 | Sharma et al. |
| 10,929,828 B2 | 2/2021 | Matsukura |
| 10,933,221 B2 | 3/2021 | Lepak et al. |
| 10,939,828 B2 | 3/2021 | Fonte et al. |
| 10,939,960 B2 | 3/2021 | Choi et al. |
| 10,943,142 B2 | 3/2021 | Karimabadi |
| 10,945,606 B2 | 3/2021 | Sanders et al. |
| 10,951,715 B2 | 3/2021 | Hart et al. |
| 10,959,789 B2 | 3/2021 | Yi et al. |
| 10,964,071 B2 | 3/2021 | Grady et al. |
| 10,966,619 B2 | 4/2021 | Fonte et al. |
| 10,973,469 B2 | 4/2021 | Daughton et al. |
| 10,973,583 B2 | 4/2021 | Taylor et al. |
| 10,978,210 B2 | 4/2021 | Grady et al. |
| 10,984,535 B2 | 4/2021 | Grady et al. |
| 10,987,010 B2 | 4/2021 | Grady et al. |
| 10,990,652 B2 | 4/2021 | Taylor et al. |
| 10,991,465 B2 | 4/2021 | Grady |
| 10,994,097 B2 | 5/2021 | Ludwin et al. |
| 11,013,425 B2 | 5/2021 | Fonte et al. |
| 11,017,904 B2 | 5/2021 | Sankaran et al. |
| 11,033,332 B2 | 6/2021 | Taylor |
| 11,042,822 B2 | 6/2021 | Sankaran et al. |
| 11,071,501 B2 | 7/2021 | Buckler et al. |
| 11,076,924 B2 | 8/2021 | Kim et al. |
| 11,083,524 B2 | 8/2021 | Taylor |
| 11,087,459 B2 | 8/2021 | Buckler et al. |
| 11,087,460 B2 | 8/2021 | Buckler et al. |
| 11,087,884 B2 | 8/2021 | Sankaran et al. |
| 11,090,118 B2 | 8/2021 | Taylor |
| 11,094,058 B2 | 8/2021 | Buckler et al. |
| 11,094,060 B1 | 8/2021 | Min et al. |
| 11,094,061 B1 | 8/2021 | Min et al. |
| 11,113,811 B2 | 9/2021 | Min et al. |
| 11,113,812 B2 | 9/2021 | Buckler et al. |
| 11,116,575 B2 | 9/2021 | Taylor |
| 11,120,312 B2 | 9/2021 | Buckler et al. |
| 11,120,549 B2 | 9/2021 | Min et al. |
| 11,120,550 B2 | 9/2021 | Min et al. |
| 11,120,893 B2 | 9/2021 | Choi et al. |
| 11,127,503 B2 | 9/2021 | Rabbat et al. |
| 11,132,796 B2 | 9/2021 | Min et al. |
| 11,135,012 B2 | 10/2021 | Taylor |
| 11,138,337 B2 | 10/2021 | Yousfi et al. |
| 11,141,566 B2 | 10/2021 | Cabiri |
| 11,147,950 B2 | 10/2021 | Destrebecq et al. |
| 11,154,361 B2 | 10/2021 | Taylor |
| 11,169,538 B2 | 11/2021 | Williams et al. |
| 11,185,368 B2 | 11/2021 | Spilker et al. |
| 11,185,666 B2 | 11/2021 | Choi et al. |
| 11,187,307 B2 | 11/2021 | Asselin et al. |
| 11,196,068 B2 | 12/2021 | Weingaertner et al. |
| 11,210,786 B2 | 12/2021 | Min et al. |
| 11,213,356 B2 | 1/2022 | Tanner et al. |
| 11,229,775 B2 | 1/2022 | Kim et al. |
| 11,232,564 B2 | 1/2022 | Min et al. |
| 11,234,767 B2 | 2/2022 | Viswanathan et al. |
| 11,238,587 B2 | 2/2022 | Min et al. |
| 11,244,451 B1 | 2/2022 | Min et al. |
| 11,257,584 B2 | 2/2022 | Buckler et al. |
| 11,257,585 B2 | 2/2022 | Bhatia et al. |
| 11,266,424 B2 | 3/2022 | Hofmann et al. |
| 11,272,995 B2 | 3/2022 | Landey et al. |
| 11,273,038 B2 | 3/2022 | Tang et al. |
| 11,276,170 B2 | 3/2022 | Min et al. |
| 11,278,703 B2 | 3/2022 | Kokish et al. |
| 11,288,799 B2 | 3/2022 | Min et al. |
| 11,288,813 B2 | 3/2022 | Grady et al. |
| 11,291,515 B2 | 4/2022 | Sharon et al. |
| 11,295,865 B2 | 4/2022 | Rabbat et al. |
| 11,298,187 B2 | 4/2022 | Taylor |
| 11,298,198 B2 | 4/2022 | Fournier et al. |
| 11,298,505 B2 | 4/2022 | Bailey et al. |
| 11,302,001 B2 | 4/2022 | Min et al. |
| 11,302,002 B2 | 4/2022 | Min et al. |
| 11,308,617 B2 | 4/2022 | Min et al. |
| 11,311,699 B2 | 4/2022 | Weisz et al. |

(56) References Cited

U.S. PATENT DOCUMENTS

| | | |
|---|---|---|
| 11,315,247 B2 | 4/2022 | Min et al. |
| 11,317,883 B2 | 5/2022 | Min |
| 11,318,302 B2 | 5/2022 | Asleson et al. |
| 11,321,840 B2 | 5/2022 | Min et al. |
| 11,328,824 B2 | 5/2022 | Fonte |
| 11,337,764 B2 | 5/2022 | Deboeuf et al. |
| 11,341,644 B2 | 5/2022 | Min et al. |
| 11,350,899 B2 | 6/2022 | Min |
| 11,357,469 B2 | 6/2022 | Taylor et al. |
| 11,367,190 B2 | 6/2022 | Min et al. |
| 11,382,569 B2 | 7/2022 | Grady et al. |
| 11,386,563 B2 | 7/2022 | Figueroa-Alvarez et al. |
| 11,398,029 B2 | 7/2022 | Grady et al. |
| 11,399,729 B2 | 8/2022 | Fonte et al. |
| 11,423,805 B2 | 8/2022 | Sankaran et al. |
| 11,424,036 B2 | 8/2022 | Fonte et al. |
| 11,424,038 B2 | 8/2022 | Grady et al. |
| 11,430,113 B2 | 8/2022 | Daughton et al. |
| 11,462,329 B2 | 10/2022 | Rabbat et al. |
| 11,482,339 B2 | 10/2022 | Koo et al. |
| 11,494,904 B2 | 11/2022 | Fonte et al. |
| 11,501,436 B2 | 11/2022 | Min et al. |
| 11,501,485 B2 | 11/2022 | Grady et al. |
| 11,504,019 B2 | 11/2022 | Fonte et al. |
| 11,508,063 B2 | 11/2022 | Buckler |
| 11,521,755 B2 | 12/2022 | Taylor et al. |
| 11,540,931 B2 | 1/2023 | Grady et al. |
| 11,547,367 B2 | 1/2023 | Taylor |
| 11,564,746 B2 | 1/2023 | Spilker et al. |
| 11,576,626 B2 | 2/2023 | Fonte et al. |
| 11,583,340 B2 | 2/2023 | Taylor |
| 11,589,924 B2 | 2/2023 | Passerini et al. |
| 11,592,836 B2 | 2/2023 | Williams et al. |
| 11,593,926 B2 | 2/2023 | Buckler et al. |
| 11,594,319 B2 | 2/2023 | Yousfi et al. |
| 11,599,996 B2 | 3/2023 | Isgum et al. |
| 11,605,466 B2 | 3/2023 | Grady et al. |
| 11,607,179 B2 | 3/2023 | Buckler et al. |
| 11,610,318 B2 | 3/2023 | Grady et al. |
| 11,617,620 B2 | 4/2023 | Tran et al. |
| 11,622,812 B2 | 4/2023 | Grady et al. |
| 11,638,609 B2 | 5/2023 | Sankaran et al. |
| 11,642,092 B1 | 5/2023 | Min |
| 11,642,171 B2 | 5/2023 | Jaquet et al. |
| 11,644,849 B2 | 5/2023 | Williams et al. |
| 11,646,118 B2 | 5/2023 | Grady et al. |
| 11,653,833 B2 | 5/2023 | Sanders et al. |
| 11,657,486 B2 | 5/2023 | Buckler et al. |
| 11,660,058 B2 | 5/2023 | Min et al. |
| 11,660,143 B2 | 5/2023 | Taylor et al. |
| 11,663,715 B2 | 5/2023 | Choi et al. |
| 11,672,497 B2 | 6/2023 | Min et al. |
| 11,676,359 B2 | 6/2023 | Buckler et al. |
| 11,678,937 B2 | 6/2023 | Choi et al. |
| 11,690,586 B2 | 7/2023 | Min et al. |
| 11,696,735 B2 | 7/2023 | Buckler et al. |
| 11,701,175 B2 | 7/2023 | Bai et al. |
| 11,707,325 B2 | 7/2023 | Sankaran et al. |
| 11,715,187 B2 | 8/2023 | Buckler et al. |
| 11,715,198 B2 | 8/2023 | Kim et al. |
| 11,730,437 B2 | 8/2023 | Min et al. |
| 11,737,718 B2 | 8/2023 | Min et al. |
| 11,742,070 B2 | 8/2023 | Grady et al. |
| 11,751,826 B2 | 9/2023 | Min et al. |
| 11,751,829 B2 | 9/2023 | Min et al. |
| 11,751,830 B2 | 9/2023 | Min et al. |
| 11,751,831 B2 | 9/2023 | Min |
| 11,756,690 B2 | 9/2023 | Koo et al. |
| 11,759,161 B2 | 9/2023 | Min |
| 11,766,229 B2 | 9/2023 | Min et al. |
| 11,766,230 B2 | 9/2023 | Min et al. |
| 11,779,292 B2 | 10/2023 | Min et al. |
| 11,784,329 B1 | 10/2023 | Basu et al. |
| 11,803,965 B2 | 10/2023 | Fonte et al. |
| 11,817,219 B2 | 11/2023 | Rabbat et al. |
| 11,826,106 B2 | 11/2023 | Hart et al. |
| 11,832,982 B2 | 12/2023 | Min et al. |
| 11,837,353 B2 | 12/2023 | Bhatia et al. |
| 11,847,781 B2 | 12/2023 | Grady et al. |
| 11,854,704 B2 | 12/2023 | Grady et al. |
| 11,861,831 B2 | 1/2024 | Choi et al. |
| 11,861,833 B2 | 1/2024 | Min et al. |
| 11,862,342 B2 | 1/2024 | Grady et al. |
| 11,865,195 B2 | 1/2024 | Sinusas et al. |
| 11,869,186 B2 | 1/2024 | Buckler et al. |
| 11,869,669 B2 | 1/2024 | Spilker et al. |
| 11,883,225 B2 | 1/2024 | Sankaran et al. |
| 11,887,305 B1 | 1/2024 | Grady et al. |
| 11,887,701 B2 | 1/2024 | Buckler et al. |
| 11,887,713 B2 | 1/2024 | Buckler et al. |
| 11,887,734 B2 | 1/2024 | Buckler et al. |
| 11,896,415 B2 | 2/2024 | Min et al. |
| 11,901,076 B1 | 2/2024 | Daughton et al. |
| 11,915,822 B2 | 2/2024 | Yi et al. |
| 11,918,293 B2 | 3/2024 | Grady et al. |
| 11,941,152 B2 | 3/2024 | Yousfi et al. |
| 11,967,078 B2 | 4/2024 | Min et al. |
| 11,986,280 B2 | 5/2024 | Grady et al. |
| 11,992,293 B2 | 5/2024 | Fonte et al. |
| 11,996,182 B2 | 5/2024 | Lee et al. |
| 12,004,841 B2 | 6/2024 | Sanders et al. |
| 12,008,751 B2 | 6/2024 | Buckler et al. |
| 12,016,635 B2 | 6/2024 | Taylor |
| 12,020,432 B2 | 6/2024 | Ross et al. |
| 12,026,868 B2 | 7/2024 | Buckler et al. |
| 12,027,275 B2 | 7/2024 | Koo et al. |
| 12,029,494 B2 | 7/2024 | Taylor |
| 12,035,976 B2 | 7/2024 | Choi et al. |
| 12,039,765 B2 | 7/2024 | Buckler et al. |
| 12,045,983 B2 | 7/2024 | Buckler et al. |
| 12,046,367 B2 | 7/2024 | Yi et al. |
| 12,048,490 B2 | 7/2024 | Grady et al. |
| 12,051,497 B2 | 7/2024 | Grady et al. |
| 12,059,288 B2 | 8/2024 | Taylor et al. |
| 12,068,079 B2 | 8/2024 | Sankaran et al. |
| 12,073,561 B2 | 8/2024 | Buckler et al. |
| 12,073,943 B2 | 8/2024 | Yu et al. |
| 12,079,921 B2 | 9/2024 | Grady et al. |
| 12,079,988 B2 | 9/2024 | Yi et al. |
| 12,096,990 B2 | 9/2024 | Sankaran et al. |
| 12,100,149 B2 | 9/2024 | Buckler et al. |
| 12,106,477 B2 | 10/2024 | Buckler et al. |
| 12,112,483 B2 | 10/2024 | Grady et al. |
| 12,114,933 B2 | 10/2024 | Seo et al. |
| 12,118,694 B2 | 10/2024 | Buckler et al. |
| 12,125,261 B2 | 10/2024 | Petersen et al. |
| 12,125,571 B2 | 10/2024 | Buckler et al. |
| 12,125,572 B2 | 10/2024 | Buckler et al. |
| 12,131,147 B2 | 10/2024 | Reasor |
| 12,131,471 B2 | 10/2024 | Buckler et al. |
| 12,131,472 B2 | 10/2024 | Buckler et al. |
| 12,136,214 B2 | 11/2024 | Buckler et al. |
| 2001/0047137 A1 | 11/2001 | Moreno et al. |
| 2002/0045153 A1 | 4/2002 | Kaufman et al. |
| 2002/0172663 A1 | 11/2002 | Palasis |
| 2003/0152519 A1 | 8/2003 | Koenig et al. |
| 2003/0176780 A1 | 9/2003 | Arnold et al. |
| 2004/0017936 A1 | 1/2004 | Gopinath et al. |
| 2004/0059260 A1 | 3/2004 | Truwit |
| 2004/0101181 A1 | 5/2004 | Giger et al. |
| 2004/0133094 A1 | 7/2004 | Becker et al. |
| 2004/0133100 A1 | 7/2004 | Naghavi et al. |
| 2004/0135031 A1 | 7/2004 | Stupakis |
| 2004/0136491 A1 | 7/2004 | Iatrou et al. |
| 2004/0147838 A1 | 7/2004 | Londt et al. |
| 2004/0254566 A1 | 12/2004 | Plicchi et al. |
| 2005/0020998 A1 | 1/2005 | Bonnette et al. |
| 2005/0038575 A1 | 2/2005 | Wu |
| 2005/0043614 A1 | 2/2005 | Huizenga et al. |
| 2005/0110791 A1 | 5/2005 | Krishnamoorthy et al. |
| 2005/0118632 A1 | 6/2005 | Chen et al. |
| 2005/0171508 A1 | 8/2005 | Gilboa |
| 2005/0245862 A1 | 11/2005 | Seward et al. |
| 2006/0013460 A1 | 1/2006 | Dehmeshki |

(56) References Cited

U.S. PATENT DOCUMENTS

| | | |
|---|---|---|
| 2006/0036167 A1 | 2/2006 | Shina |
| 2006/0101075 A1 | 5/2006 | Lehel et al. |
| 2006/0146010 A1 | 7/2006 | Schneider |
| 2007/0018558 A1 | 1/2007 | Chua et al. |
| 2007/0019778 A1 | 1/2007 | Clouse et al. |
| 2007/0172447 A1 | 7/2007 | Sakurada et al. |
| 2007/0239140 A1 | 10/2007 | Chechelski et al. |
| 2007/0248250 A1 | 10/2007 | Gulsun et al. |
| 2007/0260141 A1 | 11/2007 | Margolis et al. |
| 2008/0058642 A1 | 3/2008 | Gould |
| 2008/0100621 A1 | 5/2008 | Aharon et al. |
| 2008/0103389 A1 | 5/2008 | Begelman et al. |
| 2008/0118131 A1 | 5/2008 | Skinner et al. |
| 2008/0119713 A1 | 5/2008 | Le et al. |
| 2008/0119734 A1 | 5/2008 | Pruvot et al. |
| 2008/0123926 A1 | 5/2008 | Capolunghi et al. |
| 2008/0187199 A1 | 8/2008 | Gulsun et al. |
| 2008/0188962 A1 | 8/2008 | Suryanarayanan et al. |
| 2008/0226017 A1 | 9/2008 | Altman et al. |
| 2009/0012382 A1 | 1/2009 | Dutta et al. |
| 2009/0012533 A1 | 1/2009 | Barbagli et al. |
| 2009/0016588 A1 | 1/2009 | Slabaugh et al. |
| 2009/0082722 A1 | 3/2009 | Munger et al. |
| 2009/0129673 A1 | 5/2009 | Simon et al. |
| 2009/0264771 A1 | 10/2009 | Houben et al. |
| 2009/0276161 A1 | 11/2009 | Cobain |
| 2009/0278846 A1 | 11/2009 | Gulsun et al. |
| 2009/0299645 A1 | 12/2009 | Colby et al. |
| 2009/0307179 A1 | 12/2009 | Colby et al. |
| 2010/0030035 A1 | 2/2010 | Chan et al. |
| 2010/0092053 A1 | 4/2010 | Manabe et al. |
| 2010/0137711 A1 | 6/2010 | Hamilton et al. |
| 2010/0156898 A1 | 6/2010 | Voros et al. |
| 2010/0177945 A1 | 7/2010 | Moriya |
| 2010/0201786 A1 | 8/2010 | Schaefer et al. |
| 2010/0204646 A1 | 8/2010 | Plicchi et al. |
| 2010/0215225 A1 | 8/2010 | Kadomura et al. |
| 2010/0278405 A1 | 11/2010 | Kakadiaris et al. |
| 2010/0316274 A1 | 12/2010 | Langheinrich et al. |
| 2011/0026798 A1 | 2/2011 | Madabhushi et al. |
| 2011/0077591 A1 | 3/2011 | Plicchi et al. |
| 2011/0116697 A1 | 5/2011 | Dafni et al. |
| 2011/0144576 A1 | 6/2011 | Rothe et al. |
| 2011/0144658 A1 | 6/2011 | Wenderow et al. |
| 2011/0206247 A1 | 8/2011 | Dachille et al. |
| 2011/0218427 A1 | 9/2011 | Kitamura |
| 2011/0229002 A1 | 9/2011 | Arnold et al. |
| 2011/0238010 A1 | 9/2011 | Kirschenman et al. |
| 2011/0243412 A1 | 10/2011 | Grass et al. |
| 2011/0245650 A1 | 10/2011 | Kerwin et al. |
| 2011/0282182 A1 | 11/2011 | Ohayon et al. |
| 2012/0041323 A1 | 2/2012 | Taylor et al. |
| 2012/0075638 A1 | 3/2012 | Rollins et al. |
| 2012/0076377 A1 | 3/2012 | Dutta et al. |
| 2012/0128132 A1 | 5/2012 | Coolens et al. |
| 2012/0158011 A1 | 6/2012 | Sandhu et al. |
| 2012/0158432 A1 | 6/2012 | Jain et al. |
| 2012/0219198 A1 | 8/2012 | Mohr |
| 2012/0226227 A1 | 9/2012 | Weitzner et al. |
| 2012/0232005 A1 | 9/2012 | Dasseux et al. |
| 2012/0243764 A1 | 9/2012 | Dey et al. |
| 2012/0245595 A1 | 9/2012 | Kesavadas et al. |
| 2012/0263368 A1 | 10/2012 | Nakano et al. |
| 2012/0330335 A1 | 12/2012 | Shekalim et al. |
| 2013/0046168 A1 | 2/2013 | Sui |
| 2013/0066188 A1 | 3/2013 | Taerum et al. |
| 2013/0094749 A1 | 4/2013 | Oh et al. |
| 2013/0101187 A1 | 4/2013 | Sundar et al. |
| 2013/0190592 A1 | 7/2013 | Coppini et al. |
| 2013/0190595 A1 | 7/2013 | Oraevsky et al. |
| 2013/0202173 A1 | 8/2013 | Buckler et al. |
| 2013/0246034 A1 | 9/2013 | Sharma et al. |
| 2013/0304034 A1 | 11/2013 | Cabiri |
| 2013/0304035 A1 | 11/2013 | Cabiri |
| 2014/0058715 A1 | 2/2014 | Sharma et al. |
| 2014/0073976 A1 | 3/2014 | Fonte et al. |
| 2014/0114176 A1 | 4/2014 | Hirschenbain et al. |
| 2014/0276392 A1 | 9/2014 | Wong et al. |
| 2014/0276647 A1 | 9/2014 | Yu |
| 2014/0277333 A1 | 9/2014 | Lewis et al. |
| 2014/0306961 A1 | 10/2014 | Nagata |
| 2014/0343457 A1 | 11/2014 | Shekalim et al. |
| 2014/0350568 A1 | 11/2014 | Shekalim et al. |
| 2015/0009465 A1 | 1/2015 | Park et al. |
| 2015/0015702 A1 | 1/2015 | Yamaguchi et al. |
| 2015/0016702 A1 | 1/2015 | Huizenga et al. |
| 2015/0045287 A1 | 2/2015 | Chen et al. |
| 2015/0065846 A1 | 3/2015 | Choi et al. |
| 2015/0066818 A1 | 3/2015 | Choi et al. |
| 2015/0073340 A1 | 3/2015 | Pacheco et al. |
| 2015/0073342 A1 | 3/2015 | Pacheco et al. |
| 2015/0080907 A1 | 3/2015 | Herrell et al. |
| 2015/0090057 A1 | 4/2015 | Pacheco et al. |
| 2015/0099997 A1 | 4/2015 | Cabiri |
| 2015/0164342 A1 | 6/2015 | Choi et al. |
| 2015/0187025 A1 | 7/2015 | Wasserkrug et al. |
| 2015/0193944 A1 | 7/2015 | Lang et al. |
| 2015/0220240 A1 | 8/2015 | Tsukijishin et al. |
| 2015/0223832 A1 | 8/2015 | Swaney et al. |
| 2015/0265359 A1 | 9/2015 | Camarillo |
| 2015/0313677 A1 | 11/2015 | Kidd et al. |
| 2015/0314107 A1 | 11/2015 | Rothe et al. |
| 2015/0356734 A1 | 12/2015 | Ooga et al. |
| 2016/0012614 A1 | 1/2016 | Goto |
| 2016/0038002 A1 | 2/2016 | Peters et al. |
| 2016/0058303 A1 | 3/2016 | Grady et al. |
| 2016/0066861 A1 | 3/2016 | Taylor |
| 2016/0078309 A1 | 3/2016 | Feldman et al. |
| 2016/0103816 A1 | 4/2016 | Grady et al. |
| 2016/0104281 A1 | 4/2016 | Grady et al. |
| 2016/0203263 A1 | 7/2016 | Maier et al. |
| 2016/0210428 A1 | 7/2016 | Spilker et al. |
| 2016/0239564 A1 | 8/2016 | Sohma |
| 2016/0271368 A1 | 9/2016 | Falb et al. |
| 2016/0291110 A1 | 10/2016 | Balu et al. |
| 2016/0292372 A1 | 10/2016 | Kamen et al. |
| 2016/0296288 A1 | 10/2016 | Sankaran et al. |
| 2016/0300350 A1 | 10/2016 | Choi et al. |
| 2016/0306944 A1 | 10/2016 | Grady et al. |
| 2016/0310702 A1 | 10/2016 | Cabiri |
| 2016/0342765 A1 | 11/2016 | Sankaran et al. |
| 2016/0346043 A1 | 12/2016 | Jaquet et al. |
| 2016/0358333 A1 | 12/2016 | Lee et al. |
| 2017/0014034 A1 | 1/2017 | Koo et al. |
| 2017/0018081 A1 | 1/2017 | Taylor et al. |
| 2017/0046484 A1 | 2/2017 | Buckler et al. |
| 2017/0046839 A1 | 2/2017 | Paik et al. |
| 2017/0103525 A1 | 4/2017 | Hu et al. |
| 2017/0119333 A1 | 5/2017 | Zebaze et al. |
| 2017/0161455 A1 | 6/2017 | Grady et al. |
| 2017/0199654 A1 | 7/2017 | Wu et al. |
| 2017/0202621 A1 | 7/2017 | Taylor |
| 2017/0245821 A1 | 8/2017 | Itu et al. |
| 2017/0252025 A1 | 9/2017 | Cabiri et al. |
| 2017/0258433 A1 | 9/2017 | Gulsun et al. |
| 2017/0265831 A1 | 9/2017 | Sankaran et al. |
| 2017/0265832 A1 | 9/2017 | Antoniades |
| 2017/0337343 A1 | 11/2017 | Kakadiaris et al. |
| 2017/0340393 A1 | 11/2017 | Choi et al. |
| 2017/0348060 A1 | 12/2017 | Blacker |
| 2017/0360372 A1 | 12/2017 | Hauck et al. |
| 2017/0367776 A1 | 12/2017 | Kwok et al. |
| 2018/0050626 A1 | 2/2018 | Delp et al. |
| 2018/0064910 A1 | 3/2018 | Tegg |
| 2018/0078139 A1 | 3/2018 | Sanders et al. |
| 2018/0125596 A1 | 5/2018 | He et al. |
| 2018/0126122 A1 | 5/2018 | Cabiri |
| 2018/0165811 A1 | 6/2018 | Flohr et al. |
| 2018/0179189 A1 | 6/2018 | MacPhee et al. |
| 2018/0185104 A1 | 7/2018 | Olson et al. |
| 2018/0214675 A1 | 8/2018 | Shekalim et al. |
| 2018/0225847 A1 | 8/2018 | Grady et al. |
| 2018/0242944 A1 | 8/2018 | Uber et al. |
| 2018/0243033 A1 | 8/2018 | Tran et al. |

(56) References Cited

U.S. PATENT DOCUMENTS

| | | |
|---|---|---|
| 2018/0259976 A1 | 9/2018 | Williams et al. |
| 2018/0330477 A1 | 11/2018 | Paik et al. |
| 2018/0336319 A1 | 11/2018 | Itu et al. |
| 2018/0364738 A1 | 12/2018 | Bridges |
| 2019/0021608 A1 | 1/2019 | Cope et al. |
| 2019/0029519 A1 | 1/2019 | Itu et al. |
| 2019/0050807 A1 | 2/2019 | Ferguson et al. |
| 2019/0074082 A1 | 3/2019 | Buckler et al. |
| 2019/0076092 A1 | 3/2019 | Saroha et al. |
| 2019/0105112 A1 | 4/2019 | Popovic et al. |
| 2019/0110776 A1 | 4/2019 | Yu et al. |
| 2019/0111237 A1 | 4/2019 | Cabiri |
| 2019/0133456 A1 | 5/2019 | Grady et al. |
| 2019/0159737 A1 | 5/2019 | Buckler et al. |
| 2019/0167077 A1 | 6/2019 | Hancock et al. |
| 2019/0172197 A1 | 6/2019 | Buckler et al. |
| 2019/0174082 A1 | 6/2019 | Taruki et al. |
| 2019/0175130 A1 | 6/2019 | Raman et al. |
| 2019/0180153 A1 | 6/2019 | Buckler et al. |
| 2019/0180438 A1 | 6/2019 | Buckler et al. |
| 2019/0200881 A1 | 7/2019 | Grady et al. |
| 2019/0244347 A1 | 8/2019 | Buckler et al. |
| 2019/0244348 A1 | 8/2019 | Buckler et al. |
| 2019/0251713 A1 | 8/2019 | Chen et al. |
| 2019/0254690 A1 | 8/2019 | Cabiri et al. |
| 2019/0255289 A1 | 8/2019 | Cabiri |
| 2019/0282211 A1 | 9/2019 | Merritt et al. |
| 2019/0307987 A1 | 10/2019 | Yu |
| 2019/0318476 A1 | 10/2019 | Isgum et al. |
| 2019/0339712 A1 | 11/2019 | Williams et al. |
| 2019/0343404 A1 | 11/2019 | Shekalim et al. |
| 2019/0350538 A1 | 11/2019 | Wilson et al. |
| 2019/0388164 A1 | 12/2019 | Gruionu et al. |
| 2020/0000539 A1 | 1/2020 | Sholev et al. |
| 2020/0060820 A1 | 2/2020 | Ben-Zvi et al. |
| 2020/0069262 A1 | 3/2020 | Fonte et al. |
| 2020/0085501 A1 | 3/2020 | Sankaran et al. |
| 2020/0117851 A1 | 4/2020 | Grady et al. |
| 2020/0129252 A1 | 4/2020 | Kokish et al. |
| 2020/0129740 A1 | 4/2020 | Kottenstette et al. |
| 2020/0134897 A1 | 4/2020 | Grady et al. |
| 2020/0165309 A1 | 5/2020 | Yount et al. |
| 2020/0178815 A1 | 6/2020 | Choi et al. |
| 2020/0178990 A1 | 6/2020 | Chu |
| 2020/0179649 A1 | 6/2020 | Kern et al. |
| 2020/0188635 A1 | 6/2020 | Barrish et al. |
| 2020/0197111 A1 | 6/2020 | Kim et al. |
| 2020/0226749 A1 | 7/2020 | Freiman et al. |
| 2020/0237329 A1 | 7/2020 | Min |
| 2020/0237440 A1 | 7/2020 | Zabar et al. |
| 2020/0243076 A1 | 7/2020 | Kim |
| 2020/0243885 A1 | 7/2020 | Weingaertner et al. |
| 2020/0246089 A1 | 8/2020 | Schlenk et al. |
| 2020/0273579 A1 | 8/2020 | Wright et al. |
| 2020/0282181 A1 | 9/2020 | Cabiri |
| 2020/0294659 A1 | 9/2020 | Gopinath et al. |
| 2020/0297442 A1 | 9/2020 | Adebar et al. |
| 2020/0297971 A1 | 9/2020 | Beeckler et al. |
| 2020/0320775 A1 | 10/2020 | Holladay et al. |
| 2020/0337585 A1 | 10/2020 | Shochat et al. |
| 2020/0360659 A1 | 11/2020 | Wong et al. |
| 2020/0372701 A1 | 11/2020 | Grady et al. |
| 2020/0388391 A1 | 12/2020 | Upton et al. |
| 2020/0402234 A1 | 12/2020 | Daughton et al. |
| 2020/0405182 A1 | 12/2020 | Hoitink et al. |
| 2020/0405413 A1 | 12/2020 | Kokish et al. |
| 2021/0007807 A1 | 1/2021 | Sankaran et al. |
| 2021/0023337 A1 | 1/2021 | Debuys et al. |
| 2021/0030478 A1 | 2/2021 | Hart et al. |
| 2021/0035287 A1 | 2/2021 | Kim et al. |
| 2021/0035687 A1 | 2/2021 | Yi et al. |
| 2021/0042918 A1 | 2/2021 | Buckler |
| 2021/0042927 A1 | 2/2021 | Amis et al. |
| 2021/0045764 A1 | 2/2021 | Sholev et al. |
| 2021/0060310 A1 | 3/2021 | Kim et al. |
| 2021/0074435 A1 | 3/2021 | Taylor et al. |
| 2021/0077196 A1 | 3/2021 | Jaquet et al. |
| 2021/0077209 A1 | 3/2021 | Yu |
| 2021/0082579 A1 | 3/2021 | Grady et al. |
| 2021/0085397 A1 | 3/2021 | Passerini et al. |
| 2021/0090694 A1 | 3/2021 | Colley et al. |
| 2021/0093384 A1 | 4/2021 | Grady et al. |
| 2021/0151171 A1 | 5/2021 | Lee et al. |
| 2021/0153749 A1 | 5/2021 | Fonte et al. |
| 2021/0153945 A1 | 5/2021 | Choi et al. |
| 2021/0161384 A1 | 6/2021 | Sanders et al. |
| 2021/0177375 A1 | 6/2021 | Upton et al. |
| 2021/0185131 A1 | 6/2021 | Hart et al. |
| 2021/0186448 A1 | 6/2021 | Min |
| 2021/0196387 A1 | 7/2021 | Seo et al. |
| 2021/0196391 A1 | 7/2021 | Taylor et al. |
| 2021/0201495 A1 | 7/2021 | Yu et al. |
| 2021/0202110 A1 | 7/2021 | Grady et al. |
| 2021/0209757 A1 | 7/2021 | Min et al. |
| 2021/0210209 A1 | 7/2021 | Taylor et al. |
| 2021/0212565 A1 | 7/2021 | Gardner et al. |
| 2021/0217165 A1 | 7/2021 | Min et al. |
| 2021/0217534 A1 | 7/2021 | Rabbat et al. |
| 2021/0225006 A1 | 7/2021 | Grady et al. |
| 2021/0228094 A1 | 7/2021 | Grady et al. |
| 2021/0236105 A1 | 8/2021 | Hansen et al. |
| 2021/0236775 A1 | 8/2021 | Schultz |
| 2021/0236778 A1 | 8/2021 | Kim et al. |
| 2021/0241455 A1 | 8/2021 | Min et al. |
| 2021/0241920 A1 | 8/2021 | Sankaran et al. |
| 2021/0244475 A1 | 8/2021 | Taylor |
| 2021/0267690 A1 | 9/2021 | Taylor |
| 2021/0272030 A1 | 9/2021 | Sankaran et al. |
| 2021/0282719 A1 | 9/2021 | Buckler et al. |
| 2021/0282860 A1 | 9/2021 | Taylor |
| 2021/0312622 A1 | 10/2021 | Buckler et al. |
| 2021/0319558 A1 | 10/2021 | Min et al. |
| 2021/0322102 A1 | 10/2021 | Sankaran et al. |
| 2021/0334961 A1 | 10/2021 | Min et al. |
| 2021/0334962 A1 | 10/2021 | Min et al. |
| 2021/0334964 A1 | 10/2021 | Min et al. |
| 2021/0334965 A1 | 10/2021 | Min et al. |
| 2021/0334966 A1 | 10/2021 | Min et al. |
| 2021/0335497 A1 | 10/2021 | Sankaran et al. |
| 2021/0338333 A1 | 11/2021 | Sankaran et al. |
| 2021/0343010 A1 | 11/2021 | Min et al. |
| 2021/0358634 A1 | 11/2021 | Sankaran et al. |
| 2021/0358635 A1 | 11/2021 | Sankaran et al. |
| 2021/0361366 A1 | 11/2021 | Murphy et al. |
| 2021/0366111 A1 | 11/2021 | Min et al. |
| 2021/0366112 A1 | 11/2021 | Min et al. |
| 2021/0366113 A1 | 11/2021 | Min et al. |
| 2021/0366114 A1 | 11/2021 | Min et al. |
| 2021/0366115 A1 | 11/2021 | Min et al. |
| 2021/0366116 A1 | 11/2021 | Min et al. |
| 2021/0374969 A1 | 12/2021 | Grady et al. |
| 2021/0375401 A1 | 12/2021 | Choi et al. |
| 2021/0375476 A1 | 12/2021 | Rabbat et al. |
| 2021/0386390 A1 | 12/2021 | Min |
| 2021/0390689 A1 | 12/2021 | Buckler et al. |
| 2021/0397746 A1 | 12/2021 | Yousfi et al. |
| 2022/0012865 A1 | 1/2022 | Buckler et al. |
| 2022/0012877 A1 | 1/2022 | Buckler et al. |
| 2022/0012878 A1 | 1/2022 | Aoyama |
| 2022/0026924 A1 | 1/2022 | Williams et al. |
| 2022/0028070 A1 | 1/2022 | Min et al. |
| 2022/0059856 A1 | 2/2022 | Weingaertner et al. |
| 2022/0079540 A1 | 3/2022 | Sankaran et al. |
| 2022/0079681 A1 | 3/2022 | Grady et al. |
| 2022/0084198 A1* | 3/2022 | Viti .............. G06T 7/11 |
| 2022/0097817 A1 | 3/2022 | Perry et al. |
| 2022/0098249 A1 | 3/2022 | Shah et al. |
| 2022/0110687 A1 | 4/2022 | Spilker et al. |
| 2022/0110690 A1 | 4/2022 | Sankaran et al. |
| 2022/0111176 A1 | 4/2022 | Dale et al. |
| 2022/0114388 A1 | 4/2022 | Li et al. |
| 2022/0117683 A1 | 4/2022 | Schnur et al. |
| 2022/0122251 A1 | 4/2022 | Min et al. |
| 2022/0139529 A1 | 5/2022 | Bhatia et al. |

(56) References Cited

U.S. PATENT DOCUMENTS

| | | |
|---|---|---|
| 2022/0172353 A1 | 6/2022 | Yi et al. |
| 2022/0202857 A1 | 6/2022 | Brewer et al. |
| 2022/0211439 A1 | 7/2022 | Sankaran et al. |
| 2022/0211452 A1 | 7/2022 | Clark et al. |
| 2022/0216489 A1 | 7/2022 | Perry |
| 2022/0221861 A1 | 7/2022 | McVeen |
| 2022/0222825 A1 | 7/2022 | Yaacobi |
| 2022/0230312 A1 | 7/2022 | Choi et al. |
| 2022/0241019 A1 | 8/2022 | Taylor |
| 2022/0253074 A1 | 8/2022 | Williams et al. |
| 2022/0253992 A1 | 8/2022 | Buckler et al. |
| 2022/0265239 A1 | 8/2022 | Taylor et al. |
| 2022/0277443 A1 | 9/2022 | Min et al. |
| 2022/0284572 A1 | 9/2022 | Min et al. |
| 2022/0322953 A1 | 10/2022 | Fonte et al. |
| 2022/0327695 A1 | 10/2022 | Min et al. |
| 2022/0327701 A1 | 10/2022 | Grady et al. |
| 2022/0330902 A1 | 10/2022 | Forneris et al. |
| 2022/0335603 A1 | 10/2022 | Min et al. |
| 2022/0335859 A1 | 10/2022 | Sankaran et al. |
| 2022/0359063 A1 | 11/2022 | Tombropoulos et al. |
| 2022/0366562 A1 | 11/2022 | Yu et al. |
| 2022/0367066 A1 | 11/2022 | Grady et al. |
| 2022/0375072 A1 | 11/2022 | Min et al. |
| 2022/0383464 A1 | 12/2022 | Buckler et al. |
| 2022/0383495 A1 | 12/2022 | Petersen et al. |
| 2022/0386979 A1 | 12/2022 | Min et al. |
| 2022/0392065 A1 | 12/2022 | Min et al. |
| 2022/0392070 A1 | 12/2022 | Buckler |
| 2022/0398706 A1 | 12/2022 | Buckler et al. |
| 2022/0400963 A1 | 12/2022 | Buckler et al. |
| 2022/0401050 A1 | 12/2022 | Min |
| 2022/0406459 A1 | 12/2022 | Buckler et al. |
| 2022/0406470 A1 | 12/2022 | Fonte et al. |
| 2022/0409160 A1 | 12/2022 | Buckler et al. |
| 2022/0415519 A1 | 12/2022 | Buckler et al. |
| 2023/0005582 A1 | 1/2023 | Buckler et al. |
| 2023/0005583 A1 | 1/2023 | Buckler et al. |
| 2023/0005622 A1 | 1/2023 | Rabbat et al. |
| 2023/0016104 A1 | 1/2023 | Koo et al. |
| 2023/0033594 A1 | 2/2023 | Grady et al. |
| 2023/0055828 A1 | 2/2023 | Fonte et al. |
| 2023/0113005 A1 | 4/2023 | Antoniades et al. |
| 2023/0117134 A1 | 4/2023 | Clifton et al. |
| 2023/0124826 A1 | 4/2023 | Spilker et al. |
| 2023/0130265 A1 | 4/2023 | Kodali et al. |
| 2023/0132940 A1 | 5/2023 | Min et al. |
| 2023/0137093 A1 | 5/2023 | Min et al. |
| 2023/0137934 A1 | 5/2023 | Min et al. |
| 2023/0138144 A1 | 5/2023 | Min et al. |
| 2023/0138468 A1 | 5/2023 | Martinovski |
| 2023/0138889 A1 | 5/2023 | Min |
| 2023/0139102 A1 | 5/2023 | Taylor |
| 2023/0142747 A1 | 5/2023 | Min et al. |
| 2023/0144293 A1 | 5/2023 | Min et al. |
| 2023/0144338 A1 | 5/2023 | Min et al. |
| 2023/0145596 A1 | 5/2023 | Min et al. |
| 2023/0147336 A1 | 5/2023 | Min et al. |
| 2023/0147995 A1 | 5/2023 | Min et al. |
| 2023/0148977 A1 | 5/2023 | Fonte et al. |
| 2023/0148981 A1 | 5/2023 | Min et al. |
| 2023/0154000 A1 | 5/2023 | Min et al. |
| 2023/0154620 A1 | 5/2023 | Yi et al. |
| 2023/0162603 A1 | 5/2023 | Martin |
| 2023/0165544 A1 | 6/2023 | Hahn et al. |
| 2023/0169702 A1 | 6/2023 | Hahn et al. |
| 2023/0172451 A1 | 6/2023 | Seo et al. |
| 2023/0196582 A1 | 6/2023 | Grady et al. |
| 2023/0197286 A1 | 6/2023 | Grady et al. |
| 2023/0205227 A1 | 6/2023 | Williams et al. |
| 2023/0207137 A1 | 6/2023 | Buckler et al. |
| 2023/0210602 A1 | 7/2023 | Sankaran et al. |
| 2023/0218346 A1 | 7/2023 | Tran et al. |
| 2023/0218347 A1 | 7/2023 | Taylor |
| 2023/0223148 A1 | 7/2023 | Grady et al. |
| 2023/0233261 A1 | 7/2023 | Jaquet et al. |
| 2023/0237654 A1 | 7/2023 | Min et al. |
| 2023/0237759 A1 | 7/2023 | Buckler et al. |
| 2023/0240619 A1 | 8/2023 | Daughton et al. |
| 2023/0245775 A1 | 8/2023 | Buckler et al. |
| 2023/0248242 A1 | 8/2023 | Sanders et al. |
| 2023/0277247 A1 | 9/2023 | Taylor et al. |
| 2023/0289939 A1 | 9/2023 | Buckler et al. |
| 2023/0289963 A1 | 9/2023 | Min et al. |
| 2023/0290433 A1 | 9/2023 | Buckler et al. |
| 2023/0290524 A1 | 9/2023 | Taylor et al. |
| 2023/0298168 A1 | 9/2023 | Lee et al. |
| 2023/0298176 A1 | 9/2023 | Choi et al. |
| 2023/0301720 A1 | 9/2023 | Grady et al. |
| 2023/0301722 A1 | 9/2023 | Choi et al. |
| 2023/0310085 A1 | 10/2023 | Sankaran et al. |
| 2023/0326166 A1 | 10/2023 | Buckler et al. |
| 2023/0342923 A1 | 10/2023 | Lee et al. |
| 2023/0342929 A1 | 10/2023 | Kim et al. |
| 2023/0343455 A1 | 10/2023 | Kwon et al. |
| 2023/0352152 A1 | 11/2023 | Grady et al. |
| 2023/0360803 A1 | 11/2023 | Sankaran et al. |
| 2023/0360804 A1 | 11/2023 | Koo et al. |
| 2023/0368365 A9 | 11/2023 | Buckler et al. |
| 2023/0386026 A1 | 11/2023 | Buckler |
| 2023/0386633 A1 | 11/2023 | Buckler et al. |
| 2023/0386634 A1 | 11/2023 | Buckler et al. |
| 2023/0397816 A1 | 12/2023 | Forneris et al. |
| 2023/0420130 A1 | 12/2023 | Buckler et al. |
| 2023/0420131 A1 | 12/2023 | Buckler et al. |
| 2023/0420143 A1 | 12/2023 | Buckler et al. |
| 2023/0420144 A1 | 12/2023 | Buckler et al. |
| 2024/0000414 A1 | 1/2024 | Abdolmanafi et al. |
| 2024/0006066 A1 | 1/2024 | Buckler et al. |
| 2024/0013388 A1 | 1/2024 | Fonte et al. |
| 2024/0021306 A1 | 1/2024 | Buckler et al. |
| 2024/0023918 A1 | 1/2024 | Min |
| 2024/0038398 A1 | 2/2024 | Rabbat et al. |
| 2024/0046457 A1 | 2/2024 | Buckler et al. |
| 2024/0047045 A1 | 2/2024 | Bhatia et al. |
| 2024/0050159 A1 | 2/2024 | Hart et al. |
| 2024/0057960 A1 | 2/2024 | Min et al. |
| 2024/0062901 A1 | 2/2024 | Buckler et al. |
| 2024/0070863 A1 | 2/2024 | Grady et al. |
| 2024/0078671 A1 | 3/2024 | Buckler et al. |
| 2024/0078672 A1 | 3/2024 | Buckler et al. |
| 2024/0078673 A1 | 3/2024 | Buckler et al. |
| 2024/0087742 A1 | 3/2024 | Buckler et al. |
| 2024/0130702 A1 | 4/2024 | Flack et al. |
| 2024/0153229 A1 | 5/2024 | Buckler et al. |
| 2024/0153252 A1 | 5/2024 | Phillips et al. |
| 2024/0161295 A1 | 5/2024 | Buckler et al. |
| 2024/0161296 A1 | 5/2024 | Buckler et al. |
| 2024/0161297 A1 | 5/2024 | Buckler et al. |
| 2024/0202915 A1 | 6/2024 | Buckler et al. |
| 2024/0212143 A1 | 6/2024 | Buckler et al. |
| 2024/0232433 A1 | 7/2024 | Yousfi et al. |
| 2024/0259352 A1 | 8/2024 | Yousfi et al. |
| 2024/0274276 A1 | 8/2024 | Lee et al. |
| 2024/0298894 A1 | 9/2024 | Sanders et al. |
| 2024/0315777 A1 | 9/2024 | Choi et al. |
| 2024/0331151 A1 | 10/2024 | Seo et al. |
| 2024/0331848 A1 | 10/2024 | Seo et al. |

FOREIGN PATENT DOCUMENTS

| | | | |
|---|---|---|---|
| CA | 3017610 A1 | 9/2017 | |
| CA | 3238598 A1 | 5/2023 | |
| CA | 3240201 A1 | 6/2023 | |
| CN | 1556688 A | 12/2004 | |
| CN | 102415894 A | 4/2012 | |
| CN | 106999122 A | 8/2017 | |
| CN | 107530041 A | 1/2018 | |
| CN | 110914866 A | 3/2020 | |
| CN | 112288731 A | * 1/2021 | ........... G06T 11/003 |
| CN | 112336365 A | 2/2021 | |
| CN | 112567378 A | 3/2021 | |
| CN | 113439287 A | 9/2021 | |
| CN | 115511995 A | 12/2022 | |

(56) References Cited

FOREIGN PATENT DOCUMENTS

| | | |
|---|---|---|
| CN | 117501379 A | 2/2024 |
| CN | 117918872 A | 4/2024 |
| CN | 118077008 A | 5/2024 |
| CN | 118334070 A | 7/2024 |
| EP | 3185762 A1 | 7/2017 |
| EP | 3278254 A1 | 2/2018 |
| EP | 3326092 A1 | 5/2018 |
| EP | 3355762 A1 | 8/2018 |
| EP | 3384413 A1 | 10/2018 |
| EP | 3431005 A1 | 1/2019 |
| EP | 3457959 A1 | 3/2019 |
| EP | 3516561 A1 | 7/2019 |
| EP | 3533410 A1 | 9/2019 |
| EP | 3569150 A2 | 11/2019 |
| EP | 3585253 A1 | 1/2020 |
| EP | 3665702 A2 | 6/2020 |
| EP | 3803687 A1 | 4/2021 |
| EP | 3846176 A1 | 7/2021 |
| EP | 3899864 A1 | 10/2021 |
| EP | 3912550 A1 | 11/2021 |
| EP | 4147632 A1 | 3/2023 |
| EP | 4183344 A1 | 5/2023 |
| EP | 4252186 A1 | 10/2023 |
| EP | 4292098 A1 | 12/2023 |
| EP | 4312776 A1 | 2/2024 |
| EP | 4334941 A1 | 3/2024 |
| EP | 4377885 A1 | 6/2024 |
| EP | 4404141 A2 | 7/2024 |
| EP | 4418280 A2 | 8/2024 |
| EP | 4430534 A1 | 9/2024 |
| EP | 4445835 A2 | 10/2024 |
| EP | 4447838 A1 | 10/2024 |
| FR | 2908976 A1 | 5/2008 |
| GB | 2557263 A | 6/2018 |
| GB | 2618468 A | 11/2023 |
| IN | 202317079967 | 9/2024 |
| JP | 2003-150703 A | 5/2003 |
| JP | 2005-519657 A | 7/2005 |
| JP | 2007-029129 A | 2/2007 |
| JP | 2009-506854 A | 2/2009 |
| JP | 2011-115481 A | 6/2011 |
| JP | 2011-135938 A | 7/2011 |
| JP | 2012-509122 A | 4/2012 |
| JP | 2012-179360 A | 9/2012 |
| JP | 2012-196436 A | 10/2012 |
| JP | 5305821 B2 | 10/2013 |
| JP | 2014-534822 A | 12/2014 |
| JP | 2016-529037 A | 9/2016 |
| JP | 6203410 B2 | 9/2017 |
| JP | 2018-511791 A | 4/2018 |
| JP | 2021-525929 A | 9/2021 |
| JP | 2022-123103 A | 8/2022 |
| JP | 7113916 B2 | 8/2022 |
| JP | 2022-543330 A | 10/2022 |
| JP | 2023-054309 A | 4/2023 |
| JP | 2023-093605 A | 7/2023 |
| JP | 2023-118960 A | 8/2023 |
| JP | 2024-506605 A | 2/2024 |
| JP | 2024-069343 A | 5/2024 |
| JP | 7483079 B2 | 5/2024 |
| JP | 7505093 B2 | 6/2024 |
| JP | 2024-528679 A | 7/2024 |
| JP | 2024-113185 A | 8/2024 |
| JP | 2024-529232 A | 8/2024 |
| JP | 7542578 B2 | 8/2024 |
| KR | 10-2017-0120154 A | 10/2017 |
| KR | 10-2020-0115489 A | 10/2020 |
| KR | 10-2021-0042267 A | 4/2021 |
| KR | 10-2021-0096942 A | 8/2021 |
| KR | 10-2021-0121062 A | 10/2021 |
| KR | 10-2022-0155828 A | 11/2022 |
| KR | 10-2491988 B1 | 1/2023 |
| KR | 10-2023-0069884 A | 5/2023 |
| KR | 10-2023-0146038 A | 10/2023 |
| KR | 10-2024-0054248 A | 4/2024 |
| KR | 10-2024-0064617 A | 5/2024 |
| KR | 10-2690881 B1 | 8/2024 |
| KR | 10-2024-0133667 A | 9/2024 |
| KR | 10-2024-0147616 A | 10/2024 |
| KR | 10-2024-0147617 A | 10/2024 |
| WO | 03/39601 A1 | 5/2003 |
| WO | 2004/019256 A2 | 3/2004 |
| WO | 2007/029129 A2 | 3/2007 |
| WO | 2009/105530 A2 | 8/2009 |
| WO | 2010/067276 A1 | 6/2010 |
| WO | 2013/054947 A1 | 4/2013 |
| WO | 2014/107402 A1 | 7/2014 |
| WO | 2014/132829 A1 | 9/2014 |
| WO | 2015/095282 A1 | 6/2015 |
| WO | 2015/168682 A1 | 11/2015 |
| WO | 2016/022533 A1 | 2/2016 |
| WO | 2016/024128 A1 | 2/2016 |
| WO | 2016/138449 A1 | 9/2016 |
| WO | 2016/165432 A1 | 10/2016 |
| WO | 2016/168292 A1 | 10/2016 |
| WO | 2017/011555 A1 | 1/2017 |
| WO | 2017/096407 A1 | 6/2017 |
| WO | 2017/106819 A1 | 6/2017 |
| WO | 2018/078395 A1 | 5/2018 |
| WO | 2018/156961 A1 | 8/2018 |
| WO | 2019/033098 A2 | 2/2019 |
| WO | 2019/165432 A1 | 8/2019 |
| WO | 2019/200108 A1 | 10/2019 |
| WO | 2019/231844 A1 | 12/2019 |
| WO | 2019/242227 A1 | 12/2019 |
| WO | 2020/146360 A1 | 7/2020 |
| WO | 2021/011518 A1 | 1/2021 |
| WO | 2021/011533 A1 | 1/2021 |
| WO | 2021/011551 A1 | 1/2021 |
| WO | 2021/011554 A1 | 1/2021 |
| WO | 2021/026125 A1 | 2/2021 |
| WO | 2021/065312 A1 | 4/2021 |
| WO | 2021/117724 A1 | 6/2021 |
| WO | 2021/141135 A1 | 7/2021 |
| WO | 2021/141921 A1 | 7/2021 |
| WO | 2022/173534 A1 | 8/2022 |
| WO | 2022/221921 A1 | 10/2022 |
| WO | 2022/261506 A1 | 12/2022 |
| WO | 2023/004451 A1 | 2/2023 |
| WO | 2023/089559 A1 | 5/2023 |
| WO | 2023/111808 A1 | 6/2023 |
| WO | 2023/172273 A1 | 9/2023 |
| WO | 2024/095159 A1 | 5/2024 |
| WO | 2024/102879 A1 | 5/2024 |
| WO | 2024/105483 A1 | 5/2024 |
| WO | 2024/105484 A1 | 5/2024 |
| WO | 2024/171153 A1 | 8/2024 |

OTHER PUBLICATIONS

Abbara et al., "SCCT Guidelines for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6) pp. 435-449.

Abdelrahman et al., Sep. 8, 2020, Coronary computed tomography angiography from clinical uses to emerging technologies, Journal of the American College of Cardiology, 76(10): 1226-1243.

Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1) 14-17.

Ahmadi A. et al. "Do Plaques rapidly progress prior to myocardial infarction? The interplay between plaque vulnerability and progression." Circ Res. 2015; 117(1):99-104.

Ahmadi et al., "Lesion-Specific and Vessel-Related Determinants of Fractional Flow Reserve Beyond Coronary Artery Stenosis", JACCL Cardiovascular Imaging, vol. 11, No. 4. 2018 pp. 521-530.

Ahmadi et al., "Association of Coronary Stenosis and Plaque Morphology with Fractional Flow Reserve and Outcomes." JAMA

(56) References Cited

OTHER PUBLICATIONS cardiology 2016; 1 (3): 350-7. doi: 10.1001/jamacardio.2016.0263 [published Online First: Jul. 22, 2016].

Al'Aref et al., "High-risk atherosclerotic plaque features for cardiovascular risk assessment in the Prospective Multicenter Imaging Study for Evaluation of Chest Pain trial", Cardiovascular Diagnosis and Therapy, vol. 9, No. 1, Feb. 2019. pp. 89-93.

Al'Aref et al. "Clinical Applications of machine learning in cardiovascular disease and its relevance to cardiac imaging." Eur Heart J. Jul. 27, 2018. [Epub ahead of print].

Anjana, P.S. et al., "Study on Self Balancing Motorcycle Using the Concept of Reinforcement Learning," International Research Journal of Engineering and Technology (IRJET), vol. 7, Issue 4, Apr. 2020, pp. 6524-6531.

Antonopoulos et al., "Detecting Human coronary inflammation by imaging perivascular fat", Sci. Transl. Med. 9, eaal2658 (2017) Jul. 12, 2017.

Arbab-Zadeh et al., "Contemporary Reviews in Cardiovascular Medicine, Acute Coronary Events", Amercan Heart Assocation, Inc., Circulation. 2012;125:1147-1156, Mar. 6, 2012, pp. 1147-1156.

Arbab-Zadeh, et al. "the myth of the vulnerable plaque: transitioning from a focus on individual lesions to atherosclerotic disease burden for coronaiy artery disease risk assessment." J Arn Coll Cardiol.2015;65: 846-855.

Arthur S Agatston et al., Quantification ofcoronary artery calcium using ultrafast computed tomography, Journal of the American College of Cardiology, Mar. 15, 1990 , vol. 15, No. 4, pp. 827-832.

Bakhasi, et al. "Comparative Effectiveness of CT-Derived Atherosclerotic Plaque Metrics for Predicting Myocardial Ischemia." JACC Cardiovasc Imaging. Jul. 13, 2018. doi: 10.2013/j.jcmg.2018.05.019. [Epubahead of print].

Baskaran et al., "Dense calcium and lesion-specific ischemia: A comparison of CCTA with fractional flow reserve", Atherosclerosis 260, 2017 pp. 163-168.

Bax, Maxim et al., "Comparative differences in the atherosclerotic disease burden between the epicardial coronary arteries: quantitative plaque analysis on coronary computed tomography angiography", European Society of Cardiology, European Heart Journal—Cardiovascular Imaging (2021) 22, 322-330, published ahead-of-print online Nov. 11, 2020, 9 pages total.

Benjamin, et al. "Heart Disease and Stroke Statistics—2018 Update: A Report From the American Heart Association." Circulation. 2018;137: e67-e492.

Benjamin, Mina M, Rabbat, Mark G., "Machine learning-based advances in coronary computed tomography angiography," Editorial, Quantitative imaging in Medicine and Sugery, vol. 11, No. Jun. 6, 2021, http://dx.doi.org/10.21037/qims-21-99.

Bergman "Using Multicoloured Halftsone Screens for Offset Print Quality Monitoring", Linkdping Studies in Science and Technology; LiU-TEK-LIC-2005:02.

Blankstein R. et al. "Coronary CTA in the Evaluation of Stable Chest Pain: Clear Benefits, But Not for All." J Am Coll Cardiol 2017; 69 (14): 1771-73. doi: 10.1016/j.jacc.2017.02.011 [published Online First: Apr. 8, 2017].

Boogers, et al. "Automated Quantification of Coronary Plaque with Computed Tomography: Comparison with Intravascular Ultrasound using a Dedicated Registration Algorithm for Fusion-Based Quantification", Epub, (2012).

Boussoussou et al., 2023, The effect of patient and imaging characteristics on coronary CT angiography assessed perocoronary adipose tissue attenuation and gradient, Journal of Cardiovascular Computed Tomoaraphv, 17:34-42.

Budde et al., Sep. 15, 2021, CT-derived fractional flow reserve (FFRct) for functional coronary artery evaluation in the follow-up of patients after heart transplantation, European Radiology, https://doi.org/1 0/1007/s00330-0921-08246-5.

Budoff MJ, et al. "Diagnostic performance of 64-multidetector row coronary computed tomographic angiography for evaluation of coronary artery stenosis in individuals without know coronary artery disease: results from the prospective multicenter ACCURACY (Assessment by Coronary Computed Tomography of Individuals Undergoing Invasive Coronary Angiography) trial." J Am Coll Cardiol 2008; 52(21): 1724-32.

Bzdok "Classical Statistics and Statistical Learning in Imaging Neuroscience." Front Neurosci. 2017; 11:543.

Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901.

Celeng, et al "Non-invasive and Invasive Imaging of Vulnerable Coronary Plaque." trends Cardiovasc Med. 2016;26-538-47.

Cerqueira et al. "Standardized myocardial segmentation and nomenclature for tomographic imaging of the heart. A statement for healthcare professinals from the Cardiac Imaging Committee of the Council on Clinical Cardiology of the American Heart Association." Int J Cardiovasc Imaging 2002; 18(1): 539-42.

Chang et al., "Coronary Atherosclerotic Precursors of Acute Coronary Syndromes", Journal of the American College of Cardiology, vol. 71, No. 22, Jun. 5, 2018. pp. 2511-2522.

Chang et al., "Selective Referral Using CCTA Versus Direct Referral for Individuals Referred to Invasive Coronary Angiography for Suspected CAD", JACC: Cardiovascular Imaging, vol. 12, No. 7, Jul. 2019. pp. 1303-1312.

Chrencik et al., Sep. 2019, Quantitative assessment of carotid plaque morphology (geometry and tissue comoosition) using computed tomography angiography, Journal of Vascular Surgery, 70(3):858-868.

Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.

Costopoulos, et al "Intravascular Ultrasound and Optical Coherence Tomography Imaging of Coronary Atherosclerosis" Int J Cardiovasc Imaging 2016,32 189-200.

Cury et al., 2022, CAD-RADSTM 2.0—2022 coronary artery disease—reporting and data system an expert consensus document of the Society of Cardiovascular Computed Tomography (SCCT), the American College of Cardiology (ACC), the American College of Radiology (ACR) and the North America Society of Cardiovascular Imaging (NASCI), Journal of Cardiovascular Computed Tomography, https://doi.org/10.1016/j.jcct.2022.07.002.

Cury, et al. "CAD-RADS TM Coronary Artery Disease-Reporting and Data System. An Expert consensus documents of the Society of Cardiovascular Computed Tomography (SCCT), the American College of Radiology (ACR) and the North American Society for Cardiovascular Imaging (NASCI)." Endorsed by the American College of Cardiology. J Cardiovasc Compute Tomoqr. 2016;10: 269-81.

Danad et al. "Comparison of Coronary CT Angiography, SPECT, PET, and Hybrid Imaging for Diagnosis of Ischemic Heart Disease Determined by Fractional Flow Reserve." JAMA Cardiol 2017; 2 (10): 1100-07. doi 10.1001/jamacardio.2017.2471 [published Online First: Aug. 17, 2017].

De Bruyne B. et al. "Fractional flow reserve-guided PCI for stable coronary artery disease." The New England journal of medicine 2014; 371 (13): 1208-17. doi: 10.1056/NEJMoa1408758 [published Online First: Sep. 2, 2014].

De Bruyne et al , Sep. 13, 2012, Fractional flow reserve-guided PCA versus medical therapy in stable coronary disease, The New England Journal of Medicine, 367(11) 991-1001.

De Graaf, et al. "Automatic Quantification and Characterization of Coronary Atherosclerosis with Computed Tomography Coronary Angiography: Cross-Correlation with Intravascular Ultrasound Virtual Histology", Int J Cardiovasc, pp. 1177-1190, (2013).

De Graaf, et al. "Feasibility of an Automated Quantitative Computed Tomography Angiography—Derived Risk Stratification of Patients with Suspected CAD." Am J Cardiol (2014).

Delong ER, et al. "Comparing the areas under two or more correlated receiver operating characteristic curves: a nonparametric approach." Biometrics 1988; 44 (3): 837-45. [published Online First: Sep. 1, 1988 1.

(56) References Cited

OTHER PUBLICATIONS

Dey et al., "Direct Quantatitive In Vivo Comparison of Calcified Atherosclerotic Plaque on Vascular MRI and CT by Multimodality Image Registration" Journal of Magnetic Resonance Imaging 23:345-354 (2006).

Dey et al., 2018, Integrated prediction of lesion-specific ischemia from quantitative coronary CT Angiography using machine learning: a multicenter study, European Radiology, 28(6):2655-2664.

Dey, et al. "Comparison of Quantitative Atherosclerotic Plaque Burden from Coronary CT Angiography in Patients with First Acute Coronary Syndrome and Stable CAD" J Cardiovasc Comput tomogr (2014).

Dey, et al. "Non-Invasive Measurement of Coronary Plaque from Coronary CT Angiography and its Clinical Implication", Experl Review of Cardiovascular Therapy (2013).

Diaz-Zamudio, et al. "Automated Quantitative Plaque Burden from Coronary CT Angiography Non-Invasively Predicts Hemodynamic Significance by Using Fractional Flow Reserve in Intermediate Coronary Lesions." Radiology (2015).

Douglas et al., "Outcomes of Anatomical versus Functional Testing for Coronary Artery Disease", N Engl J Med. Apr. 2, 2015, p. 1291-1300.

Douglas et al., Aug. 2, 2016, 1-year outcomes of FFRCT-guided care in patients with suspected coronary disease, Journal of the American College of Cardiology, 68(5):435-445.

Driessen et al., "Adverse Plaque Characteristic Relate More Strongly With Hyperemic Fractional Flow Reserve and Instantaneous Wave-Free Ratio Than With Resting Instantaneous Wave-Free Ratio", JACC: Cardiovascular Imaging, 2019, in 11 pages.

Driessen et al., "Effect of Plaque Burden and Morphology on Myocardial Blood Flow and Fractional Flow Reserve", Journal of the American College of Cardiology, vol. 71, No. 5, 2018 p. 499-509.

Dwivedi et al., "Evaluation of Atherosclerotic Plaque in Non-invasice Coronary Imaging", Korean Circulation Journal, Feb. 2018. 48(2), pp. 124-133.

Ehara et al. "Spotty calcification typifies the culprit plaque in patients with acute myocardial infarction: an intravascular ultrasound study." Circulation 2004; · 110(22): 3424-9.

Erickson BJ, et al. "Machine Learning for Medical Imaging." Radiographics 2017; 37(2) pp. 505-515.

Eskerud et al., "Total coronary atherosclerotic plaque burden is associated with myocardial ischemia in non-obstructive coronary artery disease", 2021 IJC Heart & Vasculature 35:100831 9 pages (Year: 2021), Elsevier B.V.

Fawaz, Ziad, "Design and Control of a Self-balancing Bicycle Using an Electric Linear Actuator," A thesis submitted in partial fulfillment of the requirements for the degree of Master of Science in Engineering (Electrical Engineering) in the University of Michigan-Dearborn 2019, https://deepblue.lib.umich.edu/bitstream/handle/2027.42/148871/MastersThesis_FinalDraft (3).pdf?sequence=1, 34 pp.

Ferencik et al., "Use of High-Risk Coronary Atherosclerotic Plaque Detection for Risk Stratification of Patients With Stable Chest Pain", JAMA Cardiol, Feb. 2018 in 19 pages.

Ferencik, et al. "Computed Tomography-Based High-Risk Coronary Plaque Score to Predict Acute Coronary Syndrome Among Patients with Acute Chest Pain—Results from the ROMICAT II Trial" J Cardiovascular Comput Tomogr., 2015 ; 9(6): 538-545. doi:10.1016/j.jcct.2015.07.003.

Fihn et al. "2012 ACCF/AHA/ACP/AATS/PCNA/SCAI/STS Guideline for the Diagnosis and the Management of Patients With Stable Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603.

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi: 10.1016/j.jacc.2014.07.017.

Friedman et al., "Additive logistic regression: a statistical view of boosting (With discussion and a rejoinder by the authors)." Ann Statist 2000; 28(2) pp. 337-407.

Funama, Yoshinori, et al. "Improved estimation of coronary plaque and luminal attenuation using a vendor-specific model-based iterative reconstruction algorithm in contrast-enhanced CT coronary angiography." Academic radiology 24.9.

Gaemperli et al. "Cardiac hybrid imaging." Eur Heart J 2011; 32(17): 2100-8.

Gaur et al., "Coronary plaque quantification and fractional flow reserve by coronary computed tomography angiography identify ischaemia-causing lesions", European Heart Journal, 2016 pp. 1220-1227.

Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.

Gogas, et al. "Assessment of Coronary Atherosclerosis by IVUS and IVUS-based Imaging Modalities: Profession and Regression Studies, Tissue Composition and Beyond." Int J Cardiovasc Imaging. 2011;27: 225-37.

Goldstein et al., "Moving beyond regression techniques in cardiovascular risk prediction: applying machine learning to address analytic challenges." Eur Heart J. 2017; 38(23) pp. 1805-1814.

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016.

Gupta et al., Apr. 8, 2015, Moving beyond luminal stenosis: imaging strategies for stroke prevention in asymptomatic carotid stenosis, Cerebrovascular Diseases, 39:253-261.

Guyon et al., "An introduction to variable and feature selection." J Mach Learn Res. 2003; 3:1157-1182.

Hadamitzky et al., "Optimized Progostic Score for Coronary Computed Tomographic Angiography", Journal of the American College of Cardiology, vol. 62, No. 5, 2013, pp. 468-476.

Hall et al., "Benchmarking attribute selection techniques for discrete clas data mining." IEEE Transaction on Knowledge and Data Engineering 2003; 15(6): pp. 1437-1447.

Hall et al., "The WEKA data mining software: an update." SIGKDD Explor Newsl. 2009; 11(1) pp. 10-18.

Hampe, N., Van Velzen, S. G., Aben, J., Collet, C., & Isgum, I. (2023). Deep Learning-Based Prediction of Fractional Flow Reserve along the Coronary Artery. ArXiv. /abs/2308.04923.

Han et al. "Incremental role of resting myocardial computed tomography perfusion for predicting physiologically significant coronary artery disease: A machine learning approach." J Nucl Cardiol. 2018; 25(1) pp. 223-233.

Han et al., "Quantitative measurement of lipid rich plaque by coronary computed tomography angiography: A correlation of histology in sudden cardiac death", Atherosclerosis, 2018 pp. 426-433.

Hausleiter et al. "Estimated radiation dose associated with cardiac CT angiography." JAMA 2009; 301(5): 500-7.

Heo et al., "Optimal boundary detection method and window settings for coronary atherosclerotic plaque vol. analysis in coronary computed tomography angiography: comparison with intravascular ultrasound", Eur Radiol, (2016) 26:31, pp. 3190-3198.

Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.

(56) References Cited

OTHER PUBLICATIONS

Howard G. et al. "Cigarette smoking and progression of atherosclerosis: The Atherosclerosis Risk in Communities (AIRC) Study." JAMA 1998; 279(2) pp. 119-124.
Hundley WG et al. "Society for Cardiovascular Magnetic Resonance guidelines for reporting cardiovascular magnetic resonance examinations." J Cardiovasc Magn Reson 2009; 11:5.
Job, Mark, Section 510(k) premarket notification of intent to market device "Plaque View, Model No. CSPV-001 A" as filed and Review, K043111, Department of Health & Human Services, Food and Drug Administration, Nov. 18, 2004, 5 pages, Silver Springs, Maryland.
Kanamori et al. "Robust Loss Functions for Boosting" Neural Computation. 2007; 19(8) pp. 2183-2244.
Kang, et al. "Structured Learning Algorithm for Detection of Nonobstructive and Obstructive Coronary Plaque Lesions from Computed Tomography Angiography", Journal of Medical Imaging, (2015).
Kang, et al. Automated Knowledge-Based Detection of Nonobstructive and Obstructive Arterial Lesions from Coronary CT Angiography. Med Phys. 40(4): 041912-1-041912-10.
Kanitsar et al., 2002, CPR—curved planar reformation, IEEE Visualization, DOI: 10.1109/VISUAL.2002.1183754, 8 pp.
Karlof et al , 2019, Correlation of computed tomography with carotid plaque transcriptomes associates calcification with lesion-stabilization, atherosclerosis, 288 175-185.
Karlof et al , 2021, Carotid plaque phenotyping by correlating plaque morphology from computed tomography angiography with transcriptional profiling, Eur J Vas Endovas Surg , 62 716-726.
Kim et al , "Natural History of Diabetic Coronary Atherosclerosis by Quantitative Measurement of Serial Coronary Computed Tomographic Angiography", JACC Cardiovascular Imaging, vol. 11, No. 10, 2018 pp. 1461-1471.
Klass O, et al. "Coronary plaque imaging with 256-slice multidetector computed tomography: interobserver ariability of volumetric lesion parameters with semiautomatic plaque analysis software", Int J Cardiovasc Imaging, (2010). 26; pp. 711-720.
Klein et al. :Diagnostic quality of time-averaged ECG-Gated CT data, SPIE medical imaging, 2019.
Knuiman et al "An Empirical comparison of multivariable methods for estimating risk of death from coronary heart disease" J Cardiovasc Risk 1997, 4(2) pp. 127-134.
Kolossvary, et al "Radiomic Features Are Superior to Conventional Quantitative Computed Tomographic Metrics to Identify Coronary Plaques with Napkin-Ring Sign" Circ Cardiovasc Imaging 2017,10.
Koo BK, et al. "Diagnosis of ischemia-causing coronary stenoses by noninvasive fractional flow reserve computed from coronary computed tomographic angiograms. Results from the prospective multicenter Discovery-Flow (Diagnosis of Ischemia-Causes Stenoses Obtained via Noninvasive Fractional Flow Reserve) study." J Am Coll Cardiol 2011; 58 (19): 1989-97. doi: 10.1016/j.jacc.2011.06.066 [published Online First: Oct. 29, 2011].
Kramer et al. "Standardized cardiovascular magnetic resonance imaging (CMR) protocols, society for cardiovascular magnetic resonance: board of trustees task force on standardized protocols." J Cardiovasc Magn Reson 2008; 10:35. doi: 10.1186/1532-429X-10-35.
Kwan et al , "Bridging the gap for lipid lowering therapy plaque regression, coronary computed tomographic angiography, and imaging-guided personalized medicine" Expert Rev Cardiovasc Ther 2017, 15(7) pp. 547-558.
Kwee et al., Apr. 2010, Systematic review on the association between calcification in carotid plaques and clinical ischemic symptoms, Journal of Vascular Surgery, 51(4):1015-1025.
Lee et al., "Differences in Progression to Obstructive Lesions per High-Risk Plaque Features and Plaque Volumes With CCTA", JACC: Cardiovascular Imaging, 2019 in 9 pages.
Lee et al., "Effects of Statins on Coronary Atherosclerotic Plaques—The PARADIGM (Progession of AtheRosclerotic PlAque Determined by Computed TomoGraphic Angiography Imaging) Study", JACC: Cardiovascular Imaging, 2018.
Lee et al., "Identification of High-Risk Plaques Destined to Cause Acute Coronary Syndrome Using Coronary Computed Tomographic Angiography and Computational Fluid Dynamics", JACC: Cardiovascular Imagini:t vol. ·12, No. 6, Jun. 2019. pp. 1032-1043.
Lee et al., "Quantification of Coronary Atherosclerosis in the Assessment of Coronary Artery Disease." Circ Cardiovasc Imaging. 2018; 11(7): e007562.
Lee et al., Rationale and design of the Coronary Computed Tomographic Angiography for Selective Cardiac Catheterization: Relation to Cardiovascular Outcomes, Cost Effectiveness and Quality of Life (CONSERVE) trial:, Am Heart J, 2017; vol. 186, pp. 48-55.
Lee et al., "Rationale and design of the Progession of AtheRosclerotic PlAque Determined by Computed TomoGraphic Angiography Imaging (PARADIGM) registry: A comprehensive exploration of plaque progression and its impact on clinical outcomes from a multicenter serial coronary computed tomographic angiography study", American Heart Journal, vol. 182. 2016 pp. 72-79.
Lee et al., "Reproducibility in the assessment of noncalcified coronary plaque with 256-slice multi-detector CT and automated plaque analysis software", Int J Cardiovasc Imaging; 2010; 26:237-244.
Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.
Libby P. "Mechanisms of acute coronary syndromes and their implications for therapy." N Engl J Med. 2013; 368: 2004-13.
Lu et al., "Central Core Laboratory versus Site Interpretation of Coronary CT Angiography: Agreement and Association with Cardiovascular Events in tlie PROMISE Trial", Radiology: vol. 287, No. 1, Apr. 2018, pp. 87-95.
Lundberg, et al. "A Unified Approach to Interpreting Model Predictions." 31st Conference on Neural Information Processing Systems (NIPS 2017).
MacAlpin, Feb. 1980, Contribution of dynamic vascular wall thickening to luminal narrowing during coronary arterial constriction, Circulation, 60(2) 296-301.
Mancio, Jennifer, et al "Perivascular adipose tissue and coronary atherosclerosis" Hear 104 20 (2018) 1654-1662 (Year 2018).
Maurovich-Horvat et al., 2014, Comprehensive plaque assessment by coronary CT angiography, Nature Reviews Cardiology, 11 (7):390-402.
Maurovich-Horvat, et al. "The napkin-ring sign indicates advanced atherosclerotic lesions in coronary CT angiography.", JACC Cardiovasc Imaging 2012; 5(12): 1243-52.
Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j.jacc.2008.08.058.
Melikian et al. "Fractional flow reserve and myocardial perfusion imaging in patients with angiographic multivessel coronary artery disease." JACC Cardiovasc Interv 2010; 3 (3): 307-14. doi: 10.1016/'.'cin.2009.12.010 [published Online First: Mar. 20, 2010].
Mettler et al. "Effective doses in radiology and diagnostic nuclear medicine: a catalog." Radiology 2008; 248(1): 254-63.
Michail et al., Jan. 2021, Feasibility and validity of computed tomography-derived fractional flow reserve in patients with severe aortic stenosis, Circ. Cardiovasc., Interv. 14:e009586.
Miller et al. "Diagnostic performance of coronary angiography by 61-row CT." N Engel J Med 2008; 359 (22): 2324-36. doi: 10.1056/NEJMoa0806576 [published Online First: Nov. 29, 2008].
Min et al "Prognostic value of multidetector coronary computed tomographic angiography for predication of all-cause mortality" J Am Coll Cardio 2007, 50(12) 1161-70.
Min et al , "Atherosclerosis, Stenosis, and Ischemia", JACC Cardiovascular Imaging, vol. 11, No. 4, Apr. 2018 pp. 531-533.
Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].
Min et al., "The Immediate Effects of Statins on Coronary Atherosclerosis", JACC: Cardiovascular Imaging, vol. 11, No. 6, Jun. 2018. pp. 839-841.

(56) References Cited

OTHER PUBLICATIONS

Min et al., 2022, Coronary CTA plaque vol. severity stages according to invasive coronary angiography and FFR, Journal of Cardiovascular Computed Tomography, https://doi.org/10.1016/j.jcct.2002.03.001.

Min, "Atherosclerotic plaque characterization: a need for a paradigm shift for prediction of risk", European Heart Journal—Cardiovascular Imaging, Oct. 2017. pp. 1340-1341.

Min, "Chess and Coronary Artery Ischemia: Clinical Implication of Machine-Learning Applications", Circulation: Cardiovascular Imaging, 2018 in 4 pages.

Min, et al. "Rationale and Design of the CONFIRM (Coronary CT Angiography Evaluation for Clinical Outcomes: An International Multicenter) Registry." J Cardiovasc Comput Tomogr. 2011;5: 84-92.

Mintz GS. "Intravascular Imaging of Coronary Calcification and its Clinical Implications." JACC Cardiovasc Imaging. 2015;8: 461-471.

Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First:Sep. 3, 2013].

Motoyama et al. "Atherosclerotic plaque characterization by 0.5-mm-slice multislice computed tomographic imaging." Circ J 2009; 71(3): 363-6.

Motoyama et al. "Computed tomographic angiography characteristics of atherosclerotic plaques subsequently resulting in acute coronary syndrome." J Am Coll Cardiol 2009; 54(1): 49-57.

Motoyama et al. "Multislice computed tomographic characteristics of coronary lesions in acute coronary syndromes." J Am Coll Cardiol 2007; 50(4): 319-26.

Motwani et al., "Machine learning for prediction of all-cause mortality in patients with suspected coronary artery disease: a 5-year multicentre prospective registry analysis", European Heart Journal, 2017, pp. 500-507.

Murgia et al., Aug. 2020, Plaque imaging vol. analysis: technique and application, Cardiovasc Diagn Ther, 10 (4):1032-1047.

Naghavi, et al. From Vulnerable Plaque to Vulnerable Patient: a call for new definitions and risk assessment strategies: Part 1. Circulation. 2003; 108: 1664-72.

Nair, et al. "Automated Coronary Plaque Characterisation with intravascular ultrasound backscatter: ex vivo validation." EuroIntervention. 2007; 3: 113-20.

Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.

Nakazato et al., "Additive diagnostic value of atherosclerotic plaque characteristics to non-invasive FFR for identification of lesions causing ischaemia: results from a prospective international multicentre trial", http://www.pcronline.com/eurointervention/aheadof print/201509-02/ in 9 pages.

Nakazato et al., "Aggregate Plaque Volume by Coronary Computed Tomography Angiography Is Superior and Incremental to Luminal Narrowing for Diagnosis of Ischemic Lesions of Intermediate Stenosis Severity", Journal of the American College of Cardiology, vol. 62, No. 5, 2013 pp. 460-467.

Nakazato et al., "Atherosclerotic plaque characterization by CT angiography for identification of high-risk coronary artery lesions: a comparison to optical coherence tomography", European Heart Journal—Cardiovascular Imaging, vol. 16, 2015. pp. 373-379.

Nakazato et al., "Relationship of low- and high-density lipoproteins to coronary artery plaque composition by CT angiography", Journal of Cardiovascular Computed Tomography 7, 2013, pp. 83-90.

Nakazato et al., "Quantification and characterisation of coronary artery plaque vol. and adverse plaque features by coronary computed tomographic angiography: a direct comparison to intravascular ultrasound", Eur Radiol (2013) 23, pp. 2109-2117.

Narula et al., 2021, SCCT 2021 expert consensus document of coronary computed tomographic angiography: a report of the Society of Cardiovascular Computed Tomography, Journal of Cardiovascular Computed Tomography.

Neglia et al "Detection of significant coronary artery disease by noninvasive anatomical and functional imaging" Circ Cardiovasc Imaging 2015, 8 (3) doi 10 1161/CIRCIMAGING 114 002179 [published Online First Feb. 26, 2015].

Newby et al., "Coronary CT Angiography and 5-Year Risk of Myocardial Infarction", The New England Journal of Medicine, Aug. 25, 2018, pp. 924-933.

Newby et al., "CT coronary angiography in patients with suspected angina due to coronary heart disease (Scot-Heart): an open-label, parallel-group, multicentre trial", www.thelancet.com, vol. 385.Jun. 13, 2015, pp. 2383-2391.

Nicholls et al. "Intravascular ultrasound-derived measures of coronary atherosclerotic plaque burden and clinical outcome." J Am Coll Cardiol. 2010; 55(21): pp. 2399-2407.

Nicholls, et al. "Effect of Evolocumab on Coronary Plaque Composition." J Am Coll Cardiol. 2018;72: 2012-2021.

Norgaard et al., 2020, Clinical outcomes following real-world computed tomography angiography-derived factional flow reserve testing in chronic coronary syndrome patients with calcification, European Heart Journal-Cardiovascular Imaging, doi: 10.1093/ehic/jeaa173.

Norgaard et al., Apr. 1, 2014, Diagnostic performance of noninvasive fractional flow reserve derived from coronary computed tomography angiography in suspected coronary artery disease, Journal of the American Colleae of Cardioloav, 63(12):1145-1155.

Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664.(Year: 2013).

Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).

Oikonomou et al., Aug. 28, 2018, Non-invasive detection of coronary inflammation using computed tomography7 and prediction of residual cardiovascular risk (the CRIPS CT Study): a post-hoc analysis of prospective outcome data, The Lancet, 382(10151):929-393.

Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).

Otsuka et al. "Napkin-ring sign on coronary CT angiography for the prediction of acute coronary syndrome." JACC Cardiovasc Imaging 2013; 6(4): 448-57.

Ovrehus et al., "CT-based total vessel plaque analyses improves prediction of hemodynamic significance lesions as assessed by fractional flow reserve in patients with stable angina pectoris", Journal of Cardiovascular Computed Tomography 12, 2018 pp. 344-349.

Ovrehus, et al. "Reproducibility of Semi-Automatic Coronary Plaque Quantification in Coronary CT Angiography with Sub-mSv Radiation Dose." J Cardiovasc Comput Tomogr, (2016).

Papadopoulou, et al. "Detection and Quantification of Coronary Atherosclerotic plaque by 64-slice multidetector CT: A systematic head-to-head comparison with intravascular ultrasound." Atherosclerosis. 2011;219: 163-70.

Papadopoulou, et al. Reproducibility of CT Angiography Data Analysis Using Semiautomated Plaque Quantification Software: Implications for the Design of Longitudinal Studies. Int J Cardiovasc Imaging.

Park et al., "Atherosclerotic Plaque Characteristics by CT Angiography Identify Coronary Lesions That Cause Ischemia", JACC: Cardiovascular Imaging, vol. 8, No. 1, 2015 in 10 pages.

Park, et al. "Clinical Feasibility of 3D Automated Coronary Atherosclerotic Plaque Quantification Algorithm on Coronary Computed Tomography Angiography: Comparison with Intravascular Ultrasound" European Radiology (2015), 25: 3073-3083.

(56) References Cited

OTHER PUBLICATIONS

Park, et al. "Visual-functional Mismatch between Coronary Angiography and Fractional Flow Reserve." JACC Cardiovasc Interv. 2012; 5: 1029-36.

Patel et al., 2019, 1-year impact on medical practice and clinical outcomes of FFRCT, JACC: Cardiovascular Imaging, https://doi.org/10.,1016/j.jcmg.2019.03.003, 9 pp.

Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].

Pedregosa, et al. "Scikit-learn: Machine Learning in Python." Journal of Machine Learning Research, 2011; 12: 2825-2830.

Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.

Puchner et al., Mar. 2015, High-Risk Coronary Plaque at Coronary CT Angiography is Associated with NAFLD, Independent of Coronary Plaque and Stenosis Burden, ,J Cardiovasc Comput Tomogr., 27413):693-701.

Puchner, et al. "High-Risk Plaque Detected on Coronary CT Angiography Predicts Acute Coronary Syndrome independent of Significant Stenosis in Patients with Acute Chest Pain" J Am Coif Cardio/2014.

Raff, et al. "SCCT guidelines for the interpretation and reporting of coronary computed tomographic angiography" J Cardiovasc Comput Tomogr 2009: 3(2): 122-36.

Rehani et al. "ICRP Publication 117. Radiological protection in fluoroscopically guided procedures performed outside the imaging department." Ann ICRP 2010; 40(6): 1-102.

Rizvi et al., "Rationale and Design of the CREDENCE Trial computed Tomographic evaluation of atherosclerotic Determinants of myocardial Ischemia", BMC Cardiovascular Disorders, 2016, in 10 pages.

Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.

Rongero, Jeff D., Section 510(k) premarket notification of intent to market device "Vessel Analysis and Autoplaque for ORS Visual" as filed and Review, K122429, Department of Health & Human Services, Food and Drug Administration, Nov. 28, 2012, 11 pages, Silver Springs, Maryland.

Roy-Cardinal et al. "Intravascular Ultrasound Image Segmentation: A Three-Dimensional Fast-Marching Method Based on Grey Level Distributions", IEEE Transactions on Medical Imaging, vol. 25, No. 5, May 2006.

Rozie et al., 2009, Atherosclerotic plaque volume and composition in symptomatic carotid arteries assess with the multidetector CT angiography; relationship with severity of stenosis and cardiovascular risk factors, Eur Radiol, 19:2294-2301.

Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.

Samady H. et ai. "Coronary artery wall shear is associated with progression and transformation of atherosclerotic plaque and arterial remodeling in patients with coronary artery disease." American Heart Association Circulation, vol. 124, Issue 7, Aug. 16, 2011, pp. 779-788.

Schinkel et al "Noninvasive evaluation of ischaemic heart disease myocardial perfusion imaging or stress echocardiography?" European Heart Journal (2003) 24, 789-800.

Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.

Schuurman, et al. "Prognostic Value of intravascular Ultrasound in Patients with Coronary Artery Disease." J Am Coll Cardioi. 2018;72: 2003-2011.

Seghier et al , "Lesion identification using unified segmentation-normalisation models and fuzzy clustering" Neurolmage 40(2008) 1253-1266.

Seifarth, et al. "Histopathological Correlates of the Napkin-Ring Sign Plaque in Coronary CT Angiography." Send to Atherosclerosis. 2012;224: 90-6.

Sharma et al., "Stress Testing Versus CT Angiography in Patients With Diabetes and Suspected Coronary Artery Disease", Journal of the American College of Cardiology, vol. 73, No. 8, 2019 pp. 893-902.

Shaw et al "Optimal medical therapy with or without percutaneous coronary intervention to reduce ischemic burden results from the Clinical Outcomes Utilizing Revascularization and Aggressive Drug Evaluation (COURAGE) trail nuclear substudy" Circulation 2008, 117 (10) 1283-91 doi 10 116/CIRCULATIONAHA 107 743963.

Shaw et al. "Why all the focus on cardiac imaging?" JAAC Cardiovasc Imaging 2010; 3(7): 789-94 doi: 10.16/j.jcmg.2010.05.004.

Sheahan et al., Feb. 2018, Atheroscierotic plaque tissue: noninvasive quantitative assessment of characteristics with software-aided measurements from conventional CT angiography, Radiology, 286(2):622-631.

Shin S et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.

Siasos, et al. "Local Low Shear Stress and Endotheliai Dysfunction in Patients with Nonobstructive Coronary Atherosclerosis." J Arn Coll Cardiol. 2018;71: 2092-2102.

Smith, John, Section 5 IO(k) premarket notification of intent to market device "Picture archiving and communications system" as filed and Review, K190868, Department of Health & Human Services, Food and Drug Administration, Nov. 5, 2019, 10 pages, Silver Springs, Maryland.

Smith, John, Section 5 IO(k) premarket notification of intent to market device "Picture archiving and communications system" as filed and Review, K202280, Department of Health & Human Services, Food and Drug Administration, Oct. 2, 2020, 9 pages, Silver Springs, Maryland.

Smith, John, Section 510(k) premarket notification of intent to market device "Adjunctive cardiovascular status indicator" as filed and Review, K231335, Department of Health & Human Services, Food and Drug Administration, Sep. 8, 2023, 9 pages, Silver Springs, Maryland.

Song et al. "Comparison of machine learning techniques with classical statistical models in predicting health outcomes." Stud Health Technol Inform. 2004; 107(Pt 1) pp. 736-740.

Staruch, et al. "Automated Quantitative Plaque Analysis for Discrimination of Coronary Chronic Total Occlusion and Subtotal Occlusion in Computed Tomography Angiography", J Thoracic Imaging, (2016).

Stone, et al. "A prospective natural-history stucy of coronary atherosclerosis." N Engl J Med 2011; 364(3): 226-35.

Stuijfzand, et al. "Stress Myocardial Perfusion Imaging vs Coronary Computed Tomographic Angiography for Diagnosis of Invasive Vessel-Specific Coronary Physiology Predictive Modeling Results From the Computed Tomographic Evaluation of Atherosclerotic Determinants of Myocardial Ischemia (CREDENCE) Trial", JAMA Cardiology, doi:10.1001/jamacardio.2020.3409, Aug. 19, 2020.

Sun et al., Mar. 2017, Carotid plaque lipid content and fibrous cap status predict systemic cv outcomes, JACC: Cardiovascular Imaging, 10(3):241-249.

Sun, et al. "Diagnostic Value of Multislice Computed Tomography Angiography in Coronary Artery Disease: a Meta-Analysis." Eur J Radial. 2006;60: 279-86.

Taylor et al., "Patient-Specific Modeling of Cardiovascular Mechanics", Annu. Rev. Biomed. Eng. Nov. 2009:109-139.

The Copenhagen Wheel, https://senseable.mit.edu/copenhagenwheel/, website pages, 2 pages, printed on Oct. 2, 2023 (origination date unknown).

(56) References Cited

OTHER PUBLICATIONS

Thim, et al. "Unreliable Assessment of Necrotic Core by Virtual Histology Intravascular Ultrasound in Porcine Coronary Artery Disease." Circ Cardiovasc Imaging. 2010;3: 384-91.
Thygesen, et al. "Third Universal Definition of Myocardial Infarction." Glob Heart. 2013;7: 275-95.
Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.
Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.
Tomey MI, et al. "Advances in the understanding of plaque composition and treatment options: year in review." J Am Coll Cardio. 2014; 63(16) pp. 1604-1616.
Tonino et al., "Angiographic versus functional severity of coronary artery stenoses in the FAME study fractional flow reserve versus angiography in multivessel evaluation." Journal of the American College of Cardiology 2010; 55 (25): 2816-21. doi: 10.1016/j.jacc. 2009.11-096 [published Online First:2010/06/291.
Tonino et al., Jan. 15, 2009, Fractional flow reserve versus angiography for guiding percutaneous coronary interventions, The New England Journal of Medicine, 360(3):213-224.
U.S. Food and Drug Administration, Nov. 5, 2010, K100868 501(k) Summary, 10 pp.
U.S. Food and Drug Administration, Oct. 2, 2020, K202280 501(k) Summary, 9 pp.
Van Ooijen, et al. "Coronary Artery Imaging with Multidetector CT: Visualization Issues" RadioGraphics, vol. 23. (2003).
Van Rosendael et al., "Maximization of the usage of coronary CTA derived plaque information using a machine learning based algorithm to improve risk stratification; insights from the CONFIRM registry", Journal of Cardiovascular Computed Tomography 12, 2018, pp. 204-209.
Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.
Velivelli, S. L.S., et al., "Antifungal symbiotic peptide NCR044 exhibits unique structure and multifaceted mechanisms of action that confer plant protection.", Proceedings of the National Academy of Sciences, vol. 117, Issue. 27, 2020, pp. 16043-16054.
Versteylen MO, et al. "Additive value of semiautomated quantification of coronary artery diseae using cardiac computed tomographic angiography to predict future acute coronary syndrome." J Am Coll Cardiol. 2013; 61(22): pp. 2296-2305.
Virmani, et al. "Atherosclerotic plaque progression and vulnerability to rupture: angiogenesis as a source of intraplaque hemorrage." Arterioscler Thromb Vasc Biol. 2005; 25: 2054-61.
Virmani, et al. "Lessons from sudden coronary death: a comprehensive morphological classification scheme for atherosclerotic lesions." Arterioscler Thromb Vasc Biol. 2000;20: 1262-75.
Virmani, et al. "Pathology of the Vulnerable Plaque." J Am Coll Cardiol. 2006; 47: C13-8.
Wei, et al. "Computerized Detection of Noncalcified Plaques in Coronary CT Angiography: Evaluation of Topological Soft Gradient Prescreening Method and Luminal Analysis" Med Phys, (2014).
Weir-MacCall et al., "Impact of Non-obstructive left main disease on the progession of coronary artery disease: A PARADIGM substudy", Journal of Cardiovascular Computed Tomography 12, 2018, pp. 231-237.

Weisenfeld et al. "Automatic Segmentation of Newborn Brain MRI", NIH PA Author Manuscript 2010.
Williams et al. "Use of Coronary Computed Tomographic Angiography to Guide Management of Patients with Coronary Disease." Journal of American College of Cardiology 2016; 67 (15) : 1759-68. doi: 10.1016/J.Jacc.2016.02.026 [published Online First: Apr. 16, 2016].
Williams et al., "Coronary Artery Plaque Characteristics Associated With Adverse Outcomes in the SCOT-HEART Study", Journal of the American College of Cardiology, vol. 73, No. 3, Jan. 29, 2019.DD. 291-301.
Wilson et al. "Prediction of coronary heart disease using risk factor categories" Circulation 1998; 97(18) pp. 1837-1847.
Wintermark et al., May 2008, High-resolution CT imaging of carotid artery atheroscierotic plaques, Am J Neuroradiol, 29:875-882.
Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.
Won et al., "Longitudinal quanititive assessment of coronary plaque progression related to body mass index using serial coronary computed tomography angiography", European Heart Journal—Cardiovascular Imaging, 2019 pp. 591-599.
Won, Philip, Section 510(k) premarket notification of intent to market device "Medical image management and processing system" as filed and Review, K212758, Department of Health & Human Services, Food and Drug Administration, May 19, 2023, 9 pages, Silver Springs, Maryland.
Wu et al., Jun. 11, 2018. Group normalization, arXiv:1803.08494v3, [cs.CV], 10 pp.
Xu et al., Aug. 2023, ELIXR: Towards a general purpose X-ray artificial intelligence system through alignment of large language models and radiology vision encoders, arXiv.2308.01317 [cs.CV], 54 pp.
Yang et al., "Prognostic Implications of Comprehensive Whole Vessel Plaque Quantification Using Coronary Computed Tomography Angiography", Jun. 2021 JACC Asia vol. 1 No. 1:37-48 (Year 2021), Elsevier on behalf of the American College of Cardiology Foundation.
Yang, et al. "Automatic centerline extraction of coronary arteries in coronary computed tomographic angiography" The International Journal of Cardiocascular Imaging, 28, pp. 921-933. (2012).
Yokoya K, et al. "Process of progression of coronary artery lesions from mild or moderate stenosis to moderate or severe stenosis: A study based on four serial coronary arteriograms per year." Circulation 1999; 100(9); pp. 903-909.
Zeb I et al. "Effect of statin treatment on coronary plaque progression—a serial coronary CT angiography study." Atherosclerosis. 2013; 231(2) pp. 198-204.
Zhao Z., et al. "Dynamic nature of nonculprit coronary artery lesion morphology in STEMI: a serial IVUS analysis from HORIZONS-AMI trial." JACC Cardiovasc Imaging, 2013; 6(1) pp. 86-95.
Zreik et al., Dec. 10, 2018, A recurrent CNN for automatic detection and classification of coronary artery plaque and stenosis in coronary CT angiography, arXiv:1803/04360v4, 11 pp.
Zreik, M., et al. "Deep Learning Analysis of Coronary Arteries in Cardiac CT Angiography for Detection of Patients Requiring Invasive Coronary Angiography," IEEE Transactions on Medical Imaging 39, 1545-1557 (2020).
Zreik, M., et al. "Deep learning analysis of the myocardium for identification of patients with functionally significant coronary artery stenosis with coronary CT angiography.", Medical Image Analysis, vol. 44, Nov. 16, 2017, 42 pages.

* cited by examiner

| kVp \ Lumen HU | <100 | 100-199 | 200-299 | 300-399 | .... | >800 |
|---|---|---|---|---|---|---|
| 120 | 400 | 425 | 450 | 475 | .... | 525 |
| 100 | 425 | 450 | 475 | 500 | .... | 550 |
| 80 | 450 | 475 | 500 | 525 | .... | 600 |

SYSTEMS, METHODS, AND DEVICES FOR IMAGE-BASED PLAQUE ANALYSIS AND RISK DETERMINATION

PRIORITY AND RELATED APPLICATIONS

This application is a continuation of U.S. patent application Ser. No. 18/652,770, filed May 1, 2024, which is a continuation in part of and claims the benefit of priority to U.S. patent application Ser. No. 18/179,921, filed Mar. 7, 2023. U.S. patent application Ser. No. 18/179,921 claims the benefit of priority to U.S. Provisional Application No. 63/381,210, filed Oct. 27, 2022; U.S. Provisional Application No. 63/368,293, filed Jul. 13, 2022; U.S. Provisional Application No. 63/365,381, filed May 26, 2022; U.S. Provisional Application No. 63/364,084, filed May 3, 2022; U.S. Provisional Application No. 63/364,078, filed May 3, 2022; U.S. Provisional Application No. 63/362,856, filed Apr. 12, 2022; U.S. Provisional Application No. 63/362,108, filed Mar. 29, 2022; and U.S. Provisional Application No. 63/269,136, filed Mar. 10, 2022. This application also claims the benefit of priority to U.S. Provisional Application No. 63/557,405 filed Feb. 23, 2024; U.S. Provisional Application No. 63/557,401 filed Feb. 23, 2024; U.S. Provisional Application No. 63/606,584 filed Dec. 5, 2023; U.S. Provisional Application No. 63/597,528 filed Nov. 9, 2023; U.S. Provisional Application No. 63/582,792 filed Sep. 14, 2023; U.S. Provisional Application No. 63/519,220 filed Aug. 11, 2023; U.S. Provisional Application No. 63/557,396 filed Feb. 23, 2024; and U.S. Provisional Application No. 63/499,602 filed May 2, 2023. The contents of each of the above listed applications are incorporated by reference herein in their entirety. Any and all applications for which a foreign or domestic priority claim is identified in the Application Data Sheet as filed with the present application are hereby incorporated by reference under 37 CFR 1.57.

TECHNICAL FIELD

The present application relates to non-invasive image-based plaque analysis and risk determination. Some embodiments relate to treatment plans for plaque. Some implementations related to guiding local and/or systemic plaque treatment using image-based plaque analysis. Some embodiments relate to normalization of medical images for plaque analysis, vascular analysis, or both. Some embodiments related to coronary artery disease risk stratification. Some embodiments related to reconstructing a coronary artery tree using one or more image series. Some embodiments related to approaches for identifying calcified plaques using coronary computed tomography angiography. Some implementations relate to adjusting a variable plaque categorization threshold. Some embodiments relate to approaches for detecting thin cap fibroatheroma using coronary computed tomography angiography. Some embodiments relate to stent selection and surgical planning.

BACKGROUND

The approaches described in this section are approaches that could be pursued, but not necessarily approaches that have been previously conceived or pursued. Thus, unless otherwise indicated, it should not be assumed that any of the material described in this section qualifies as prior art merely by virtue of its inclusion in this section.

Coronary plaque presents a significant health problem. However, there are problems with current diagnostic and treatment approaches. Accordingly, improved approaches are needed.

SUMMARY

Various embodiments described herein relate to systems, devices, and methods for image-based plaque analysis and risk determination. In particular, in some embodiments, the systems, devices, and methods described herein are related to analysis of one or more regions of plaque, such as for example coronary plaque, based on one or more distances, volumes, densities, radiodensities, shapes, morphologies, embeddedness, and/or axes measurements.

Various embodiments described herein relate to systems, devices, and methods for guiding local and/or systemic plaque treatment using image-based plaque analysis. In particular, in some embodiments, the systems, devices, and methods described herein are related to image-based analysis of one or more regions of plaque, such as for example coronary plaque, based on one or more distances, volumes, densities, radiodensities, shapes, morphologies, embeddedness, and/or axes measurements. For example, in some embodiments, the systems, devices, and methods described herein are related to using one or more such analyses of plaque to determine and/or guide determining local and/or systemic treatment of plaque for a patient. In some embodiments, the systems, devices, and methods described herein are configured to utilize machine learning (ML) and/or artificial intelligence (AI).

Various embodiments described herein relate to systems, devices, and methods for normalization of medical images for plaque and/or vascular analysis. Some embodiments relate more particularly to image processing algorithms that can be used to compare images taken with different image acquisition parameters.

Various embodiments described herein relate to systems, devices, and methods for image-based coronary artery disease (CAD) risk stratification.

Various embodiments described herein relate to systems, devices, and methods for reconstructing coronary artery trees.

Various embodiments described herein relate to systems, devices, and methods for plaque categorization, and in particular to automatically adjusting plaque categorization thresholds for computed tomography images.

Various embodiments described herein relate to systems, devices, and methods for detecting thin-cap fibroatheroma using coronary computed tomography angiography.

Various embodiments described herein relate to systems, devices, and methods for analyzing lesions in blood vessels. Some embodiments relate to stent selection. Some embodiments relate to surgical planning. Some embodiments relate to robotic surgical planning.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

Detailed descriptions of implementations of the present invention will be described and explained through the use of the accompanying drawings.

Figure 1:
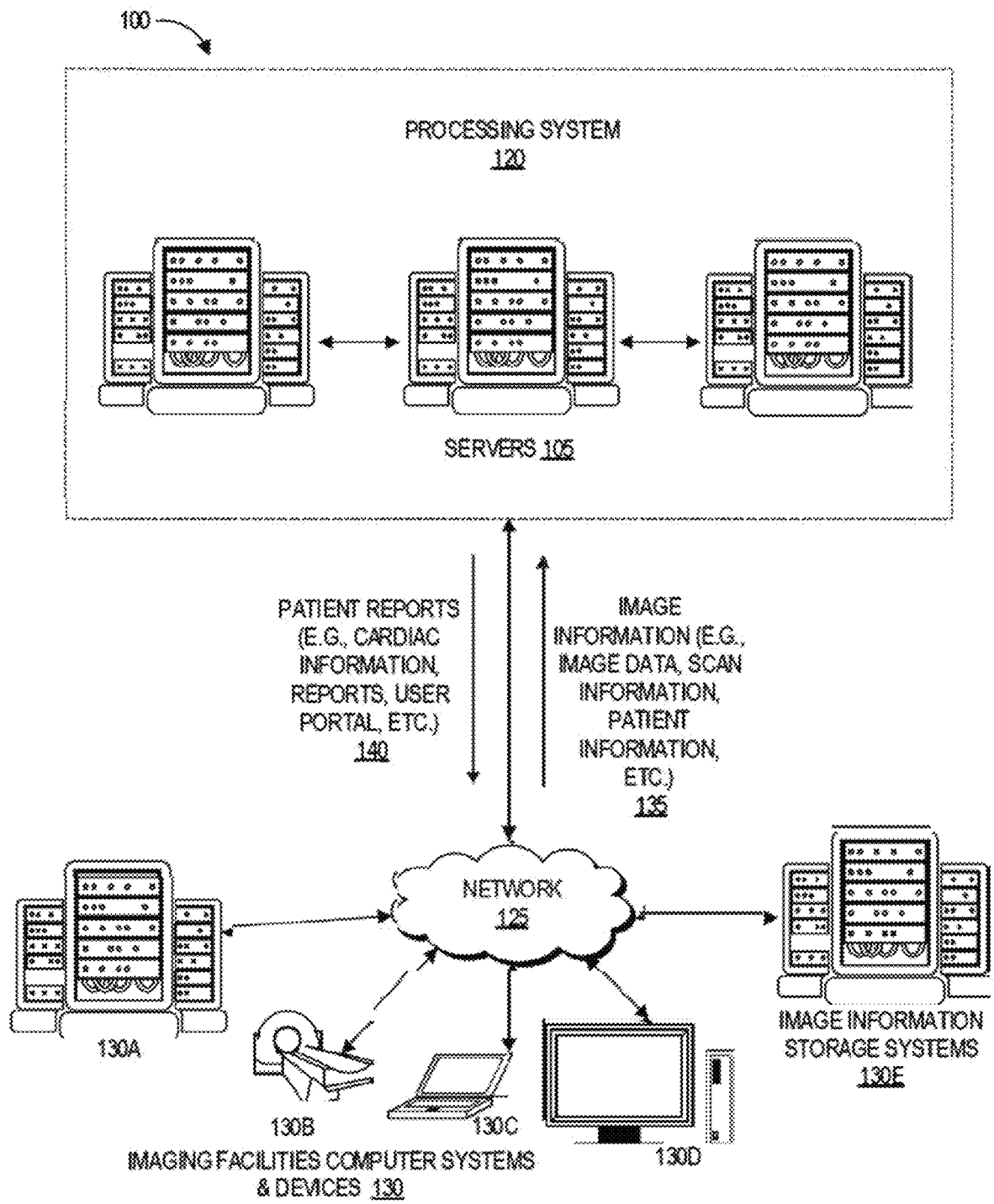
FIG. 1 depicts a schematic of an example embodiment of a system that includes a processing system configured to characterize coronary plaque.

The technologies described herein will become more apparent to those skilled in the art from studying the Detailed Description in conjunction with the drawings. Embodiments or implementations describing aspects of the invention are illustrated by way of example, and the same references can indicate similar elements. While the drawings depict various implementations for the purpose of illustration, those skilled in the art will recognize that alternative implementations can be employed without departing from the principles of the present technologies. Accordingly, while specific implementations are shown in the drawings, the technology is amenable to various modifications.

DETAILED DESCRIPTION

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

"Plaque" or "a region of plaque" or "one or more regions of plaque" may be referred to simply as "plaque" for ease of reference unless otherwise indicated, explicitly or by context. For example, in some embodiments, the systems, devices, and methods described herein are related to plaque analysis based on one or more of distance between plaque (e.g., coronary plaque) and a vessel wall, distance between plaque and a lumen wall, length along longitudinal axis of plaque, length along latitudinal axis of plaque, area or volume of low density non-calcified plaque, area or volume of non-calcified plaque, area or volume of calcified plaque, area or volume of total plaque, a ratio(s) between one or more of area or volume of low density non-calcified plaque, area or volume of non-calcified plaque, area or volume of calcified plaque, or area or volume of total plaque, and one or more of area or volume of low density non-calcified plaque, area or volume of non-calcified plaque, area or volume of calcified plaque, or area or volume of total plaque, embeddedness of low density non-calcified plaque, non-calcified plaque, calcified plaque, total plaque, or any plaque, and/or the like. In some embodiments, the systems, devices, and methods described herein are configured to determine a risk of coronary artery disease (CAD) and/or major adverse cardiovascular event (MACE), such as myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein. In some embodiments, the systems, devices, and methods described herein can be configured to generate a plurality of proposed treatments, from which an interventionist may select.

In some embodiments, the systems, methods, and devices described herein are configured to analyze one or more coronary computed tomography angiography (CCTA) images to identify one or more high-risk plaques or atherosclerosis. In some embodiments, high-risk plaque or atherosclerosis can be identified when one or more high-risk factors are present, including for example high volume, burden, composition, density (also referred to herein as material density), radiodensity, and/or the like. In some embodiments, high-risk plaque or atherosclerosis can be identified on the patient level, at the lesion level, or at any other intermediate level.

In some embodiments, the systems, methods, and devices described herein can be configured to analyze total plaque volume for a patient and/or presence and/or prevalence or extent of high-risk plaques. For example, in some embodiments, high-risk plaques can be identified based on low attenuation, low material density, low radiodensity, and/or high lesion-level plaque volume. In some embodiments, the systems, methods, and devices described herein can be configured to determine or generate a lesion-level risk score. In some embodiments, a lesion-level risk score can be configured to be used to identify one or more local lesions that have a poor prognosis and/or that comprise a high or relatively high risk of becoming a culprit lesion at the time of a future MI or other MACE.

INTRODUCTION

Coronary heart disease affects over 17.6 million Americans. The current trend in treating cardiovascular health issues is generally two-fold. First, physicians generally review a patient's cardiovascular health from a macro level, for example, by analyzing the biochemistry, blood content, and/or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure, in which a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 25,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen and/or to generate a more effective treatment plan, it can be important to more fully understand the cardiovascular disease of a patient. Specifically, it can be advantageous to better understand the arterial vessel health of a patient. For example, it is helpful to understand whether plaque build-up in a patient is mostly fatty matter build-up or mostly calcified matter build-up, because the former situation may warrant treatment with heart medicines, such as statins, whereas in the latter situation a patient should be subject to further periodic monitoring without prescribing heart medicine or implanting any stents. However, if the plaque build-up is significant enough to cause severe stenosis or narrowing of the arterial vessel such that blood flow to heart muscle might be blocked, then an invasive angioplasty procedure to implant a stent may likely be required because heart attack or sudden cardiac death (SCD) could occur in such patients without the implantation of a stent to enlarge the vessel opening. Sudden cardiac death is one of the largest causes of natural death in the United States, accounting for approximately 325,000 adult deaths per year and responsible for nearly half of all deaths from cardiovascular disease. For males, SCD is twice as common as compared to females. In general, SCD strikes people in the mid-30 to mid-40 age range. In over 50% of cases, sudden cardiac arrest occurs with no warning signs.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients, whereas arteries containing "bad" or unstable plaque or plaque comprising fatty material are considered more life threatening because such bad plaque may rupture within arteries, releasing such fatty material into the arteries. Such a fatty material release in the bloodstream can cause inflammation that may result in a blood clot. A blood clot within an artery can prevent blood from traveling to heart muscle, which can cause a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture in which there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

In some embodiments, the systems, devices, and methods described herein are configured to utilize non-invasive medical imaging technologies, such as a CT imaging or CCTA for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image or CCTA, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, fat, and/or one or more measurements thereof from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk and/or disease state assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is in stark contrast to existing measures today which do not produce reproducible prognosis or assessment, take extensive amounts of time, and/or require invasive procedures. In some embodiments, the systems, methods, and devices described herein comprise and/or are configured to utilize any one or more of such techniques described in US Patent Application Publication No. US 2021/0319558, which is incorporated herein by reference in its entirety.

As such, in some embodiments, the systems, devices, and methods described herein are able to provide physicians and/or patients specific quantified and/or measured data relating to a patient's plaque and/or ischemia that do not exist today. In some embodiments, such detailed levels of quantified plaque parameters from image processing and downstream analytical results can provide more accurate and useful tools for assessing the health and/or risk of patients in completely novel ways.

Disclosed are methods for identification of high-risk plaques using volumetric characterization of coronary plaque and perivascular adipose tissue data by computed tomography (CT) scanning. The volumetric characterization of the coronary plaque and perivascular adipose tissue allows for determination of the inflammatory status of the plaque by CT scanning. This is of use in the diagnosis, prognosis, and treatment of coronary artery disease. While certain example embodiments are shown by way of example in the drawings and will herein be described in detail, these embodiments are capable of various modifications and alternative forms. There is no intent to limit example embodiments to the particular forms disclosed, but on the contrary, example embodiments are to cover all modifications, equivalents, and alternatives falling within the scope of example embodiments.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes all combinations of one or more of the associated listed items.

The terminology used herein is for the purpose of describing embodiments only and is not intended to be limiting to example embodiments. As used herein, the singular forms "a," "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof. In this specification, the term "and/or" picks out each individual item as well as all combinations of them.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein. It should also be noted that in some alternative implementations, the functions/acts noted may occur out of the order noted in the figures. For example, two functions/acts shown in succession may in fact be executed concurrently or may sometimes be executed in the reverse order, depending upon the functionality/acts involved.

In the drawings, the dimensions of layers and regions are exaggerated for clarity of illustration. It will also be understood that when a layer (or tissue) is referred to as being "on" another layer or tissue, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being 'between' two layers, it can be the only layer between the two layers, or one or more intervening layers may also be present. Like reference numerals refer to like elements throughout.

In some embodiments, the system can be configured to characterize a particular region of plaque as high-risk or low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

Overview of Example Processing System to Characterize Coronary Plaque

This disclosure includes methods and systems of using data generated from images collected by scanning a patient's arteries to identify coronary artery plaques that are at higher risk of causing future heart attack or acute coronary syndrome. In particular, the characteristics of perivascular coronary fat, coronary plaque, and/or the coronary lumen, and the relationship of the characteristics of perivascular coronary fat, coronary plaque, and/or the coronary lumen are discussed to determine ways for identifying the coronary plaque that is more susceptible to implication in future ACS, heart attack and death. The images used to generate the image data may be CT images, CCTA images, or images generated using any applicable technology that can depict the relative densities of the coronary plaque, perivascular fat, and coronary lumen. For example, CCTA images may be used to generate two-dimensional (2D) or volumetric (three-dimensional (3D)) image data, and this image data may be analyzed to determine certain characteristics that are associated with the radiodensities of the coronary plaque, perivascular fat, and/or coronary lumen. In some implementations, the Hounsfield scale is used to provide a measure of the radiodensity of these features. A Hounsfield unit, as is known, represents an arbitrary unit of x-ray attenuation used for CT scans. Each pixel (2D) or voxel (3D) of a feature in the image data may be assigned a radiodensity value on the Hounsfield scale, and then these values characterizing the features may be analyzed.

In various embodiments, processing of image information may include: (1) determining scan parameters (for example, mA (milliampere), kVp (peak kilovoltage)); (2) determining the scan image quality (e.g., noise, signal-to-noise ratio, contrast to noise ratio); (3) measuring scan-specific coronary artery lumen densities (e.g., from a point distal to a coronary artery wall to a point proximal to the coronary artery wall to distal to the coronary artery, and from a central location of the coronary artery to an outer location (e.g., outer relative to radial distance from the coronary artery): (4) measuring scan-specific plaque densities (e.g., from central to outer, abruptness of change within a plaque from high-to-low or low-to-high) as a function of their 3D shape; and (5) measuring scan-specific perivascular coronary fat densities (from close to the artery to far from the artery) as a function of its 3D shape.

From these measurements, which are agnostic to any commonly known features of ischemia-causing atherosclerosis, the systems and methods of some embodiments described herein can determine several characteristics, including but not limited to one or more of:

1. A ratio of lumen attenuation to plaque attenuation, wherein the volumetric model of scan-specific attenuation density gradients within the lumen adjusts for reduced luminal density across plaque lesions that are more functionally significant in terms of risk value;
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases;
3. A ratio of lumen attenuation/plaque attenuation/fat attenuation;
4. A ratio of #1-3 as a function of 3D shape of atherosclerosis, which can include a 3D texture analysis of the plaque;
5. The 3D volumetric shape and path of the lumen along with its attenuation density from the beginning to the end of the lumen;
6. The totality of plaque and plaque types before and after any given plaque to further inform its risk; or
7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

Other characteristics can also be determined.

The above listed characteristics/metrics, and others, can be analyzed together to assess the risk of the plaque being implicated in future heart attack, ACS, ischemia, or death. This can be done through development and/or validation of a traditional risk score or through machine learning methods. Factors for analysis from the metrics that are likely to be associated with heart attack, ACS, ischemia or death, may include one or more of: (1) a ratio of [bright lumen:dark plaque]; (2) a ratio of [dark plaque:light fat]; (3) a ratio of [bright lumen:dark plaque:light fat]; or (4) a low ratio of [dark lumen:dark myocardium in 1 vessel area]/[lumen:myocardium in another vessel area]. Some improvements in the disclosed methods and systems may include one or more of: (1) using numerical values from ratios of [lumen:plaque], [plaque:fat] and [lumen:plaque:fat] instead of using qualitative definitions of atherosclerotic features; (2) using a scan-specific [lumen:plaque attenuation] ratio to characterize plaque; (3) using a scan-specific [plaque:fat attenuation] ratio to characterize plaque; (4) using ratios of [lumen:plaque:fat circumferential] to characterize plaque; or (5) integration of plaque volume and type before and after as a contributor to risk for any given individual plaque.

Atherosclerotic plaque features may change over time with medical treatment (e.g., colchicine and statin medications) and while some of these medications may retard progression of plaque, they also have very important roles in promoting the change in plaque. While statin medications may have reduced the overall progression of plaque, they may also have actually resulted in an increased progression of calcified plaque and a reduction of non-calcified plaque. This change will be associated with a reduction in heart attack or ACS or death, and the disclosed methods can be used to monitor the effects of medical therapy on plaque risk over time. Also, this method can also be used to identify individuals whose atherosclerotic plaque features or [lumen:plaque]/[plaque:fat]/[lumen:plaque:fat] ratios indicate that they are susceptible to rapid progression or malignant transformation of disease. In addition, these methods can be applied to single plaques or to a patient-basis wherein whole-heart atherosclerosis tracking can be used to monitor risk to the patient for experiencing heart attack (rather than trying to identify any specific plaque as being causal for future heart attack). Tracking can be done by automated co-registration processes of image data associated with a patient over a period of time.

FIG. 1 depicts a schematic of an example of an embodiment of a system 100 that includes a processing system 120 configured to characterize coronary plaque. The processing system 120 may include one or more servers (or computers) 105 each configured with one or more processors. In some embodiments, the processing system 120 includes non-transitory computer memory components for storing data and non-transitory computer memory components for storing instructions that are executed by the one or more processors data communication interfaces, the instructions configuring the one or more processors to perform methods of analyzing image information. A more detailed example of a server/computer 105 is described in reference to FIG. 6.

In some embodiments, the system 100 also includes a network. The processing system 120 can be in communication with the network 125. The network 125 may include, as at least a portion of the network 125, the Internet, a wide area network (WAN), a wireless network, or the like. In some embodiments, the processing system 120 is part of a "cloud" implementation, which can be located anywhere that is in communication with the network 125. In some embodiments, the processing system 120 is located in the same geographic proximity as an imaging facility that images and stores patient image data. In some embodiments, the processing system 120 is located remotely from where the patient image data is generated or stored.

FIG. 1 also illustrates in system 100 various computer systems and devices 130 (e.g., of an imaging facility) that may be related to generating patient image data and that are also connected to the network 125. One or more of the devices 130 may be at an imaging facility that generates images of a patient's arteries, a medical facility (e.g., a hospital, doctor's office, etc.) or may be the personal computing device of a patient or care provider. For example, as illustrated in FIG. 1, an imaging facility server (or computer) 130A may be connected to the network 125. Also, in this example, a scanner 130B in an imaging facility may be connected to the network 125. One or more other computer devices may also be connected to the network 125. For example, a laptop 130C, a personal computer 130D, and/or and an image information storage system 130E may also be connected to the network 125, and communicate with the processing system 120, and each other, via the network 125.

In some examples, the scanner 130B can be a computed tomography (CT) scanner that uses a rotating X-ray tube and a row of detectors to measure X-ray attenuations by different tissues in the body and form a corresponding image. In another example, a scanner 130B can use a spinning tube ("spiral CT") in which an entire X-ray tube and detectors are spun around a central axis of the area being scanned. In another example, the scanner 130B can utilize electron beam tomography (EBT). In another example, the scanner 130B can be a dual source CT scanner with two X-ray tube systems. In another example, the scanner 130B can be a multi-source CT scanner with more than two X-ray tube systems. In another example, the scanner 130B can include a fast switching X-ray tube system. The methods and systems described herein can also use images from other CT scanners. In some examples, the scanner 130B is a photon counting CT scanner, a spectral CT scanner, or a dual energy CT scanner. A photon counting CT scanner, a spectral CT scanner, a multispectral CT scanner, or a dual energy CT scanner can help provide more detailed higher resolution images that better show small blood vessels, plaque, and other vascular pathologies, and allow for the determination of absolute material densities over relative densities. In general, a photon counting CT scanner may use an X-ray detector to count photons and quantifies the energy, determining the count of the number of photons in several discrete energy bins, resulting in higher contrast to noise ratio, and improved spatial resolution and spectral imaging compared to conventional CT scanners. Each registered photon can be assigned to a specific bin depending on its energy, such that each pixel measures a histogram of the incident X-ray spectrum. This spectral information can provide several advantages. First, it can be used to quantitatively determine the material composition of each pixel in the reconstructed CT image, as opposed to the estimated average linear attenuation coefficient obtained in a conventional CT scan. The spectral/energy information can be used to remove beam hardening artifacts that occur at higher linear attenuation of many materials that shifts mean energy of the X-ray spectrum towards higher energies. Also, use of more than two energy bins can allow discrimination between objects (bone, calcifications, contrast agents, tissue, etc.). In some embodiments, images generated using a photon counting CT scanner can allow assessment of plaques at different monochromatic energies as well as different polychromatic spectra (e.g., 100 kVp, 120 kVp, 140 kVp, etc.), and this can change definition of non-calcified and calcified plaques compared to conventional CT scanners. A spectral CT scanner can use different X-ray wavelengths (or energies) to produce a CT scan. A dual energy CT scanner can use separate X-ray energies to detect two different energy ranges. In an example, a dual energy CT scanner (also known as spectral CT) can use an X-ray detector with separate layers to detect two different energy ranges ('dual layer'). In another example, a dual energy CT scanner can use a single scanner to scan twice using two different energy levels (e.g., electronic kVp switching). Images can be formed from combining the images detected at each different energy level, or the images may be used separately to assess a medical condition of a patient. In addition to providing absolute material densities, a photon counting CT scanner can also allow for evaluation of images that are "monochromatic" as opposed to the typical CT, which is polychromatic spectra of light. As noted above, features (e.g., low density non-calcified plaque, calcified plaque, non-calcified plaque) that are depicted images formed using a photon counting CT scanner, a spectral CT scanner, or a dual energy CT scanner may have different radiodensities than those depicted in images formed from a conventional CT scanner, that is, such images may affect or change the definition of calcified and non-calcified plaque. However, radiodensities of calcified and non-calcified plaque, or other features depicted in images formed from a photon counting CT scanner, a spectral CT scanner, or a dual energy CT scanner, can be normalized to correspond to densities of conventional CT scanners and to the densities disclosed herein. Accordingly, the radiodensities disclosed herein can be directly correlated to radiodensities of images generated with a photon counting CT scanner, a spectral CT scanner, or a dual energy CT scanner such that the systems and methods, analysis, plaque densities etc. disclosed herein are directly applicable to images formed from a photon counting CT scanner, a spectral CT scanner, or a dual energy CT scanner, and can be directly applicable to images formed from a photon counting CT scanner, a spectral CT scanner, or a dual energy CT scanner that are normalized to equivalent conventional CT scanner radiodensities.

The information communicated from the devices 130 to the processing system 120 via the network 125 may include image information 135. In various embodiments, the image information 135 may include 2D or 3D image data of a patient, scan information related to the image data, patient information, and other imagery or image related information that relates to a patient. For example, the image information may include patient information including (one or more) characteristics of a patient, for example, age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, lab results and the like. In some embodiments, the image information includes identification information of the patient, for example, patient's name, patient's address, driver's license number, Social Security number, or indicia of another patient identification. Once the processing system 120 analyzes the image information 135, information relating to a patient 140 may be communicated from the processing system 120 to a device 130 via the network 125. The patient information 140 may include for example, a patient report. Also, the patient information 140 may include a variety of patient information which is available from a patient portal, which may be accessed by one of the devices 130.

In some embodiments, image information comprising a plurality of images of a patient's coronary arteries and patient information/characteristics may be provided from one or more of the devices 130 to the one or more servers 105 of the processing system 120 via a network 125. In some embodiments, the processing system 120 is configured to generate coronary artery information using the plurality of images of the patient's coronary arteries to generate two-dimensional and/or three-dimensional data representations of the patient's coronary arteries. In some embodiments, the processing system 120 analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligence techniques, the data representations of the patient's coronary arteries may be compared to other patients' data representations (e.g., that are stored in a database) to determine additional information about the patient's health. For example, based on certain plaque conditions of the patient's coronary arteries, the likelihood of a patient having a heart attack or other adverse coronary effect can be determined. Also, for example, additional information about the patient's risk of CAD may also be determined.

Figure 2:
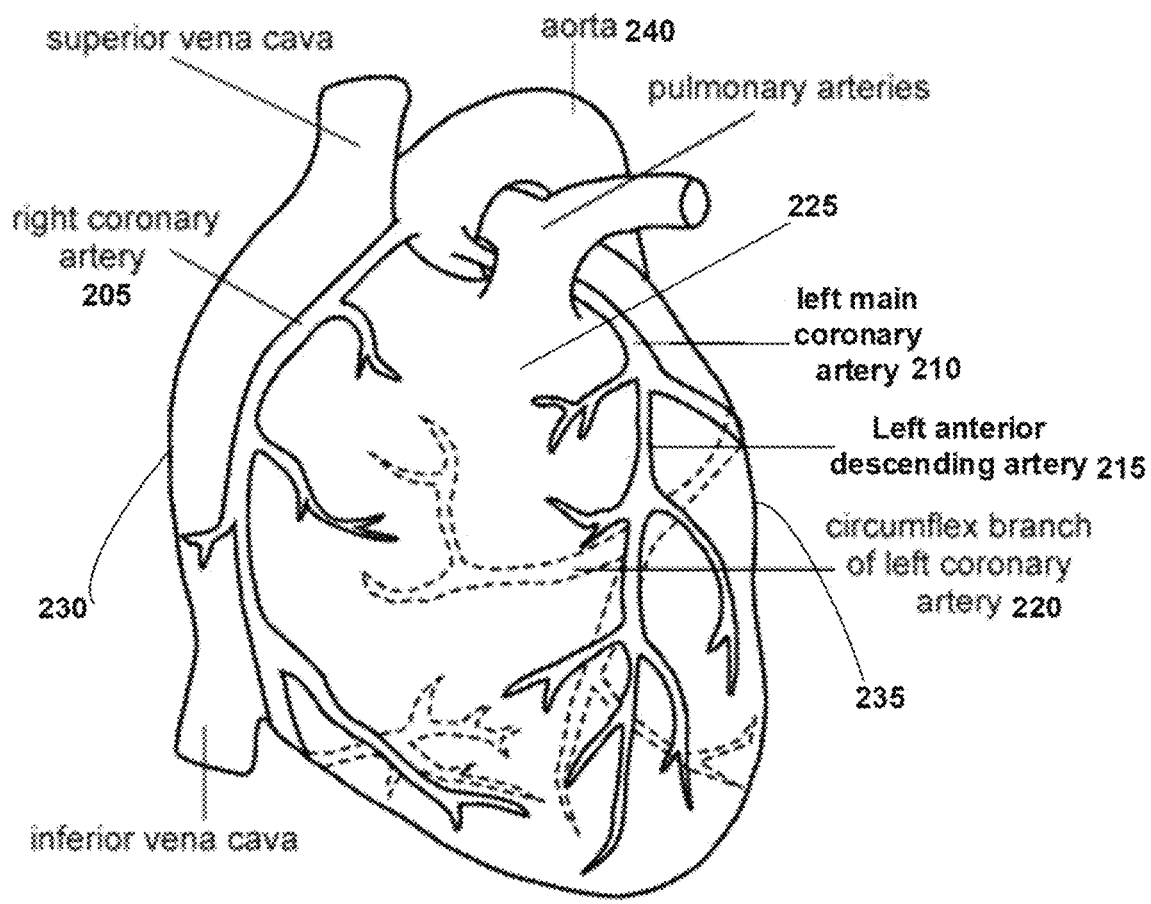
FIG. 2 is a schematic illustrating an example of a heart muscle and its coronary arteries.

FIG. 2 is a schematic illustrating an example of a heart muscle 225 and its coronary arteries. The coronary vasculature includes a complex network of vessels ranging from large arteries to arterioles, capillaries, venules, veins, etc. FIG. 2 depicts a model of a portion of the coronary vasculature that circulates blood to and within the heart and includes an aorta 240 that supplies blood to a plurality of coronary arteries, for example, a left anterior descending (LAD) artery 215, a left circumflex (LCX) artery 220, and a right coronary (RCA) artery 205, described further below. Coronary arteries supply blood to the heart muscle 225. Like all other tissues in the body, the heart muscle 225 needs oxygen-rich blood to function. Also, oxygen-depleted blood must be carried away. The coronary arteries wrap around the outside of the heart muscle 225. Small branches dive into the heart muscle 225 to bring it blood. The examples of methods and systems described herein may be used to determine information relating to blood flowing through the coronary arteries in any vessels extending therefrom. In particular, the described examples of methods and systems may be used to determine various information relating to one or more portions of a coronary artery where plaque has formed which is then used to determine risks associated with such plaque, for example, whether a plaque formation is a risk to cause an adverse event to a patient.

The right side 230 of the heart 225 is depicted on the left side of FIG. 2 (relative to the page) and the left side 235 of the heart is depicted on the right side of FIG. 2. The coronary arteries include the right coronary artery (RCA) 205 which extends from the aorta 240 downward along the right side 230 of the heart 225, and the left main coronary artery (LMCA) 210 which extends from the aorta 240 downward on the left side 235 of the heart 225. The RCA 205 supplies blood to the right ventricle, the right atrium, and the SA (sinoatrial) and AV (atrioventricular) nodes, which regulate the heart rhythm. The RCA 205 divides into smaller branches, including the right posterior descending artery and the acute marginal artery. Together with the left anterior descending artery 215, the RCA 205 helps supply blood to the middle or septum of the heart.

The LMCA 210 branches into two arteries, the anterior interventricular branch of the left coronary artery, also known as the left anterior descending (LAD) artery 215 and the circumflex branch of the left coronary artery 220. The LAD artery 215 supplies blood to the front of the left side of the heart. Occlusion of the LAD artery 215 is often called the widow-maker infarction. The circumflex branch of the left coronary artery 220 encircles the heart muscle. The circumflex branch of the left coronary artery 220 supplies blood to the outer side and back of the heart, following the left part of the coronary sulcus, running first to the left and then to the right, reaching nearly as far as the posterior longitudinal sulcus.

Figure 3:
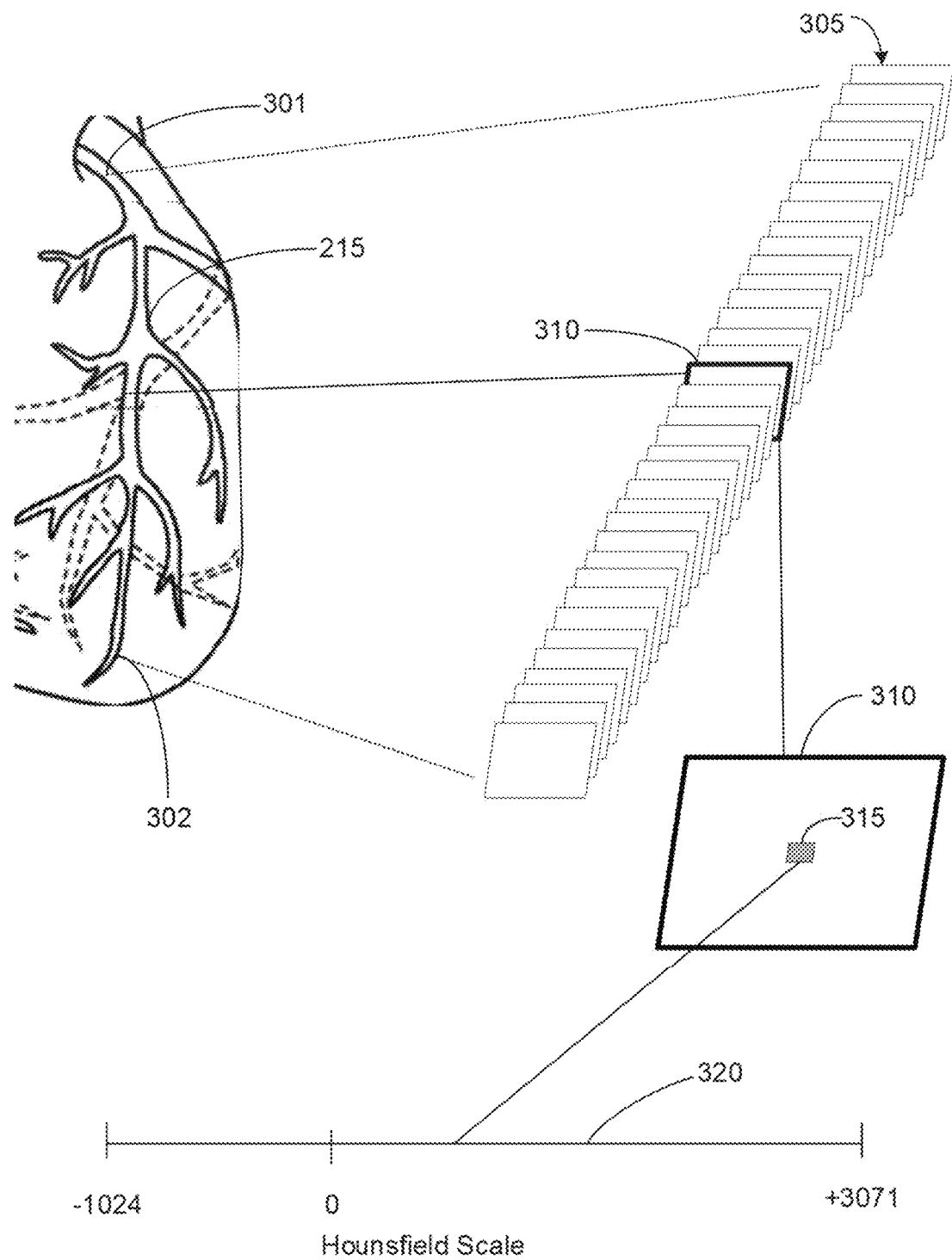
FIG. 3 illustrates an example of a set of images generated from scanning along a coronary artery, including a selected image of a portion of a coronary artery, and how image data may correspond to a value on the Hounsfield Scale.

FIG. 3 illustrates an example of a set of images generated from scanning along a coronary artery, including a selected image of a portion of a coronary artery, and how image data may correspond to a value on the Hounsfield Scale. As discussed in reference to FIG. 1, in addition to obtaining image data, scan information including metrics related to the image data, and patient information including characteristics of the patient may also be collected.

A portion of a heart 225, the LMCA 210, and the LAD artery 215 is illustrated in the example of FIG. 3. A set of images 305 can be collected along portions of the LMCA 210 and the LAD artery 215, in this example from a first point 301 on the LMCA 210 to a second point 302 on the LAD artery 215. In some examples, the image data may be obtained using noninvasive imaging methods. For example, CCTA image data can be generated using a scanner to create images of the heart in the coronary arteries and other vessels extending therefrom. Collected CCTA image data may be subsequently used to generate three-dimensional image models of the features contained in the CCTA image data (for example, the right coronary artery 205, the left main coronary artery 210, the left anterior descending artery 215, the circumflex branch of the left coronary artery 220, the aorta 240, and other vessels related to the heart that appear in the image data.

In various embodiments, different imaging methods may be used to collect the image data. For example, ultrasound or magnetic resonance imaging (MRI) may be used. In some embodiments, the imaging methods involve using a contrast agent to help identify structures of the coronary arteries, the contrast agent being injected into the patient prior to the imaging procedure. The various imaging methods may each have their own advantages and disadvantages of usage, including resolution and suitability of imaging the coronary arteries. Imaging methods which may be used to collect image data of the coronary arteries are constantly improving as improvements to the hardware (e.g., sensors and emitters) and software are made. The disclosed systems and methods contemplate using CCTA image data and/or any other type of image data that can provide or be converted into a representative 3D depiction of the coronary arteries, plaque contained within the coronary arteries, and perivascular fat located in proximity to the coronary arteries containing the plaque such that attenuation or radiodensity values of the coronary arteries, plaque, and/or perivascular fat can be obtained. In some embodiments, the imaging modality can comprise one or more of CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), near-field infrared spectroscopy (NIRS), contrast-enhanced CT, or non-contrast CT.

Referring still to FIG. 3, a particular image 310 of the image data 305 is shown, which represents an image of a portion of the left anterior descending artery 215. The image 310 includes image information, the smallest point of the information manipulated by a system referred to herein generally as a pixel, for example pixel 315 of image 310. The resolution of the imaging system used to capture the image data will affect the size of the smallest feature that can be discerned in an image. In addition, subsequent manipulation of the image may affect the dimensions of a pixel. As one example, the image 310 in a digital format, may contain 4000 pixels in each horizontal row, and 3000 pixels in each vertical column. Pixel 315, and each of the pixels in image data 310 and in the image data 305, can be associated with a radiodensity value that corresponds to the density of the pixel in the image. Illustratively shown in FIG. 3 is mapping pixel 315 to a point on the Hounsfield scale 320. The Hounsfield scale 320 is a quantitative scale for describing radiodensity. The Hounsfield unit scale linear transformation of the original linear attenuation coefficient measurement into one in which the radiodensity of distilled water at standard pressure and temperature is defined as zero Hounsfield units (HU), while the radiodensity of air at standard pressure and temperature is defined as −1000 HU. Although FIG. 3 illustrates an example of mapping pixel 315 of image 310 to a point on the Hounsfield scale 320, such an association of a pixel to a radiodensity value can also be done with 3D data. For example, after the image data 305 is used to generate a three-dimensional representation of the coronary arteries.

Once the data has been obtained and rendered into a three-dimensional representation, various processes can be performed on the data to identify areas of analysis. For example, a three-dimensional depiction of a coronary artery may be segmented to define a plurality of portions of the artery and identified as such in the data. In some embodiments, the data may be filtered (e.g., smoothed) by various methods to remove anomalies that are the result of scanning or other various errors. Various known methods for segmenting and smoothing the 3D data may be used, and therefore for brevity of the disclosure will not be discussed in any further detail herein.

Figure 4:
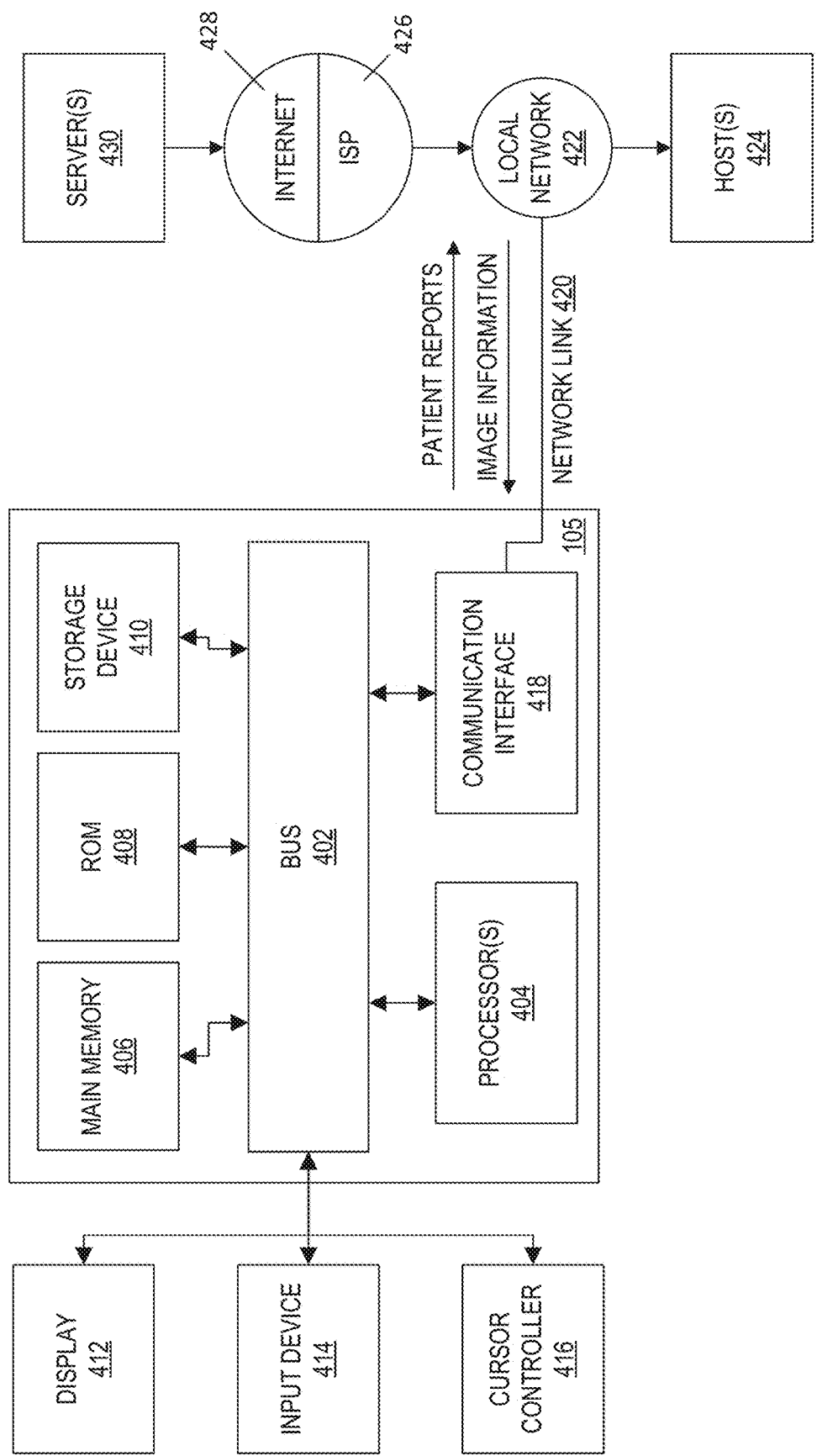
FIG. 4 is a block diagram that illustrates a computer system upon which various embodiments may be implemented.

FIG. 4 is a block diagram that illustrates a computer system 400 upon which various embodiments may be implemented. In some embodiments, the computer system 400 includes a bus 402 or other communication mechanism for communicating information, and a hardware processor, or multiple processors, 404 coupled with bus 402 for processing information. Hardware processor(s) 404 may be, for example, one or more general purpose microprocessors.

In some embodiments, the computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, may render the computer system 400 into a special-purpose machine that is customized to perform the operations specified in the instructions. The main memory 406 may, for example, include instructions that analyze image information to determine characteristics of coronary features (e.g., plaque, perivascular fat, and coronary arteries) to produce patient reports containing information that characterizes aspects of the patient's health relating to their coronary arteries. For example, one or more metrics may be determined, the metrics including one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature.

In some embodiments, the computer system 400 further includes a read only memory (ROM) 408 or other static storage device coupled to bus 402 for storing static information and instructions for processor 404. In some embodiments, a storage device 410, such as a magnetic disk, optical disk, or USB thumb drive (Flash drive), etc., is provided and coupled to bus 402 for storing information and instructions.

Computer system 400 may be coupled via bus 402 to a display 412, such as a cathode ray tube (CRT) or LCD display (or touch screen), for displaying information to a computer user. In some embodiments, an input device 414, including alphanumeric and other keys, is coupled to bus 402 for communicating information and command selections to processor 404. Another type of user input device can include cursor control 416, such as a mouse, a trackball, or cursor direction keys for communicating direction information and command selections to processor 404 and for controlling cursor movement on display 412. In some embodiments, this input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 400 may include a user interface module to implement a GUI that may be stored in a mass storage device as computer executable program instructions that are executed by the computing device(s). Computer system 400 may further, as described below, implement the techniques described herein using customized hard-wired logic, one or more ASICs or FPGAs, firmware and/or program logic which in combination with the computer system causes or programs computer system 400 to be a special-purpose machine. According to some embodiments, the techniques herein are performed by computer system 400 in response to processor(s) 404 executing one or more sequences of one or more computer readable program instructions contained in main memory 406. Such instructions may be read into main memory 406 from another storage medium, such as storage device 410. In some embodiments, execution of the sequences of instructions contained in main memory 406 causes processor(s) 404 to perform the process steps described herein. In some embodiments, hard-wired circuitry may be used in place of or in combination with software instructions.

Various forms of computer readable storage media may be involved in carrying one or more sequences of one or more computer readable program instructions to processor 404 for execution. For example, the instructions may initially be carried on a magnetic disk or solid state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

In some embodiments, the computer system 400 also includes a communication interface 418 coupled to bus 402. In some embodiments, the communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN (or WAN component to communicate with a WAN). Wireless links may also be implemented. In any such implementation, communication interface 418 sends and receives electrical, electromagnetic, or optical signals that carry digital data streams representing various types of information.

In some embodiments, the network link 420 typically provides data communication through one or more networks to other data devices. For example, network link 420 may provide a connection through local network 422 to a host computer 424 or to data equipment operated by an Internet Service Provider (ISP) 426. In some embodiments, the ISP 426 in turn provides data communication services through the worldwide packet data communication network now commonly referred to as the "Internet" 428. Local network 422 and Internet 428 may both use electrical, electromagnetic, or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

Accordingly, in some embodiments, the computer system 105 comprises a non-transitory computer storage medium storage device 410 configured to at least store image information of patients. The computer system 105 can also include non-transitory computer storage medium storage that stores instructions for the one or more processors 404 to execute a process (e.g., a method) for characterization of coronary plaque tissue data and perivascular tissue data using image data gathered from a computed tomography (CT) scan along a blood vessel, the image information including radiodensity values of coronary plaque and perivascular tissue located adjacent to the coronary plaque. Executing the instructions, in some embodiments, the one or more processors 404 can quantify, in the image data, the radiodensity in regions of coronary plaque, quantify in the image data, radiodensity in at least one region of corresponding perivascular tissue adjacent to the coronary plaque, determine gradients of the quantified radiodensity values within the coronary plaque and the quantified radiodensity values within the corresponding perivascular tissue, determine a ratio of the quantified radiodensity values within the coronary plaque and the corresponding perivascular tissue, and characterizing the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. In some embodiments, a network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression, or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Some aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

Based on the identified features and/or quantified measurements, for example from analyzing one or more medical images, in some embodiments, the system can be configured to generate a risk assessment and/or track the progression of a plaque-based disease or condition, such as for example atherosclerosis, stenosis, ischemia, myocardial infarction, and/or major adverse cardiovascular event (MACE), using raw medical images. As described further herein, in some embodiments the system can perform risk assessment and/or tracking the progression of a plaque-based disease based on other patients' information. For example, by comparing or evaluating features in a patient's medical images and patient information (e.g., age, gender, BMI, medication, blood pressure, heart rate, height, weight, race, whether the patient is a smoker or non-smoker, medical history, family history of disease, etc.) to features in other patients' medical images and their associated patient information including their outcome after a period of time.

Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or response to non-response to medication and/or lifestyle change and/or other treatment and/or invasive procedure. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is in stark contrast to existing measures today which do not produce reproducible prognosis or assessment, take extensive amounts of time, and/or require invasive procedures.

In some embodiments, image information comprising a plurality of images of a patient's coronary arteries and patient information/characteristics may be provided from one or more of the devices to the one or more servers of the processing system via a network. The processing system is configured to generate coronary artery information using the plurality of images of the patient's coronary arteries to generate two-dimensional and/or three-dimensional data representations of the patient's coronary arteries. Then, the processing system analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligence techniques, the data representations of the patient's coronary arteries may be compared to other patients' data representations (e.g., that are stored in a database) to determine additional information about the patient's health. In some embodiments, the artificial intelligence can be trained using a dataset of other patients' data representations to identify correlations in data. For example, based on certain plaque conditions of the patient's coronary arteries, the likelihood of a patient having a heart attack or other adverse coronary effect can be determined. Also, for example, additional information about the patient's risk of CAD may also be determined.

In some embodiments, the coronary plaque information of a patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, a neural network is used to compare a patient's coronary artery information to numerous (e.g., 10,000+) other patients' coronary artery information. For such patients that have similar patient information and similar cardiac information, risk assessments of the plaque of the patient being examined may be determined.

In some embodiments, Deep Learning (DL) methods, machine learning (ML) methods, and/or artificial intelligence (AI) methods can be used to analyze image information. In an example, this analysis can comprise image segmentation, feature extraction, and classification. In some embodiments, ML methods can comprise image feature extraction and image-based learning from raw data. In some embodiments, the ML method can receive an input of a large training set to learn to ignore variations that could otherwise skew the results of the method. In some embodiments, DL can comprise a Neural Network (NN) with three or more layers that can improve the accuracy of determinations. Advantageously, in some embodiments, DL can obviate the need for pre-processing data and, instead, process raw data. For example, while a human may input a hierarchy of important features of coronary image information for a ML algorithm to make determinations, DL algorithms can determine which features are important and use these features to make determinations. Advantageously, in some embodiments, a DL algorithm can adjust itself for accuracy and precision. In some embodiments, ML and DL algorithms can perform supervised learning, unsupervised learning, and reinforcement learning.

In some embodiments, NN approaches, including convolutional neural networks (CNN) and recurrent convolutional neural networks (RCNN), among others, can be used to analyze information in a manner similar to high-level cognitive functions of a human mind. In some embodiments, a NN approach can comprise training an object recognition system numerous medical images in order to teach it patterns in the images that correlate with particular labels. In some embodiments, a CNN can comprise a NN where the nodes of each layer are clustered, the clusters overlap, and each cluster feeds data to multiple nodes of the next layer. In some embodiments, a RCNN can comprise a CNN where recurrent connections are incorporated in each convolutional layer. Advantageously, in some embodiments, the recurrent connections can make object recognition a dynamic process despite the fact that the input is static.

In some embodiments, the vessel identification algorithm, coronary artery identification algorithm, and/or plaque identification algorithm can be trained on a plurality of medical images wherein one or more vessels, coronary arteries, and/or regions of plaque are pre-identified. Based on such training, for example by use of a CNN in some embodiments, the system can be configured to automatically and/or dynamically identify from raw medical images the presence and/or parameters of vessels, coronary arteries, and/or plaque. In some embodiments, the system can be configured to utilize one or more AI and/or ML algorithms to identify and/or analyze vessels or plaque, derive one or more quantification metrics and/or classifications, and/or generate a treatment plan. In some embodiments, the system can be configured to utilize an AI and/or ML algorithm to identify areas in an artery that exhibit plaque buildup within, along, inside and/or outside the arteries. In some embodiments, input to the AI and/or ML algorithms can include images of a patient and patient information (or characteristics), for example, one or more of age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, lab results, and/or the like. In an example where a NN is used, the NN can be trained using information from a plurality of patients, where the information for each patient can include medical images and one or more patient characteristics.

In some embodiments, the system can be configured to utilize one or more AI and/or ML algorithms to automatically and/or dynamically identify one or more regions of plaque using image processing. For example, in some embodiments, the one or more AI and/or ML algorithms can be trained using a CNN on a set of medical images on which regions of plaque have been identified, thereby allowing the AI and/or ML algorithm to automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

In some embodiments, the one or more vascular morphology parameters and/or plaque parameters can comprise quantified parameters derived from the medical image. For example, in some embodiments, the system can be configured to utilize an AI and/or ML algorithm or other algorithm to determine one or more vascular morphology parameters and/or plaque parameters. As another example, in some embodiments, the system can be configured to determine one or more vascular morphology parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

In some embodiments, the system is configured to classify atherosclerosis of a subject based on the quantified atherosclerosis as one or more of high risk, medium risk, or low risk. In some embodiments, the system is configured to classify atherosclerosis of a subject based on the quantified atherosclerosis using an AI, ML, and/or other algorithm. In some embodiments, the system is configured to classify atherosclerosis of a subject by combining and/or weighting one or more of a ratio of volume of surface area, volume, heterogeneity index, and radiodensity of the one or more regions of plaque.

In some embodiments, the system can be configured to identify one or more regions of fat, such as epicardial fat, in the medical image, for example using one or more AI and/or ML algorithms to automatically and/or dynamically identify one or more regions of fat. In some embodiments, the one or more AI and/or ML algorithms can be trained using a CNN on a set of medical images on which regions of fat have been identified, thereby allowing the AI and/or ML algorithm to automatically identify regions of fat directly from a medical image. In some embodiments, the system can be configured to identify regions of fat based on the radiodensity values typically associated with fat, for example by setting a predetermined threshold or range of radiodensity values that are typically associated with fat with or without normalizing using a normalization device.

In some embodiments, the system is configured to utilize an AI, ML, and/or other algorithm to characterize the change in calcium score based on one or more plaque parameters derived from a medical image. For example, in some embodiments, the system can be configured to utilize an AI and/or ML algorithm that is trained using a CNN and/or using a dataset of known medical images with identified plaque parameters combined with calcium scores. In some embodiments, the system can be configured to characterize a change in calcium score by accessing known datasets of the same stored in a database. For example, the known dataset may include datasets of changes in calcium scores and/or medical images and/or plaque parameters derived therefrom of other subjects in the past. In some embodiments, the system can be configured to characterize a change in calcium score and/or determine a cause thereof on a vessel-by-vessel basis, segment-by-segment basis, plaque-by-plaque basis, and/or a subject basis.

In some embodiments, the systems disclosed herein can be used to dynamically and automatically determine a necessary stent type, length, diameter, gauge, strength, and/or any other stent parameter for a particular patient based on processing of the medical image data, for example using AI, ML, and/or other algorithms.

In some embodiments, the system can be configured to utilize an AI and/or ML algorithm to generate the patient-specific report. In some embodiments, the patient-specific report can include a document, AR experience, VR experience, video, and/or audio component.

Figure 5A:
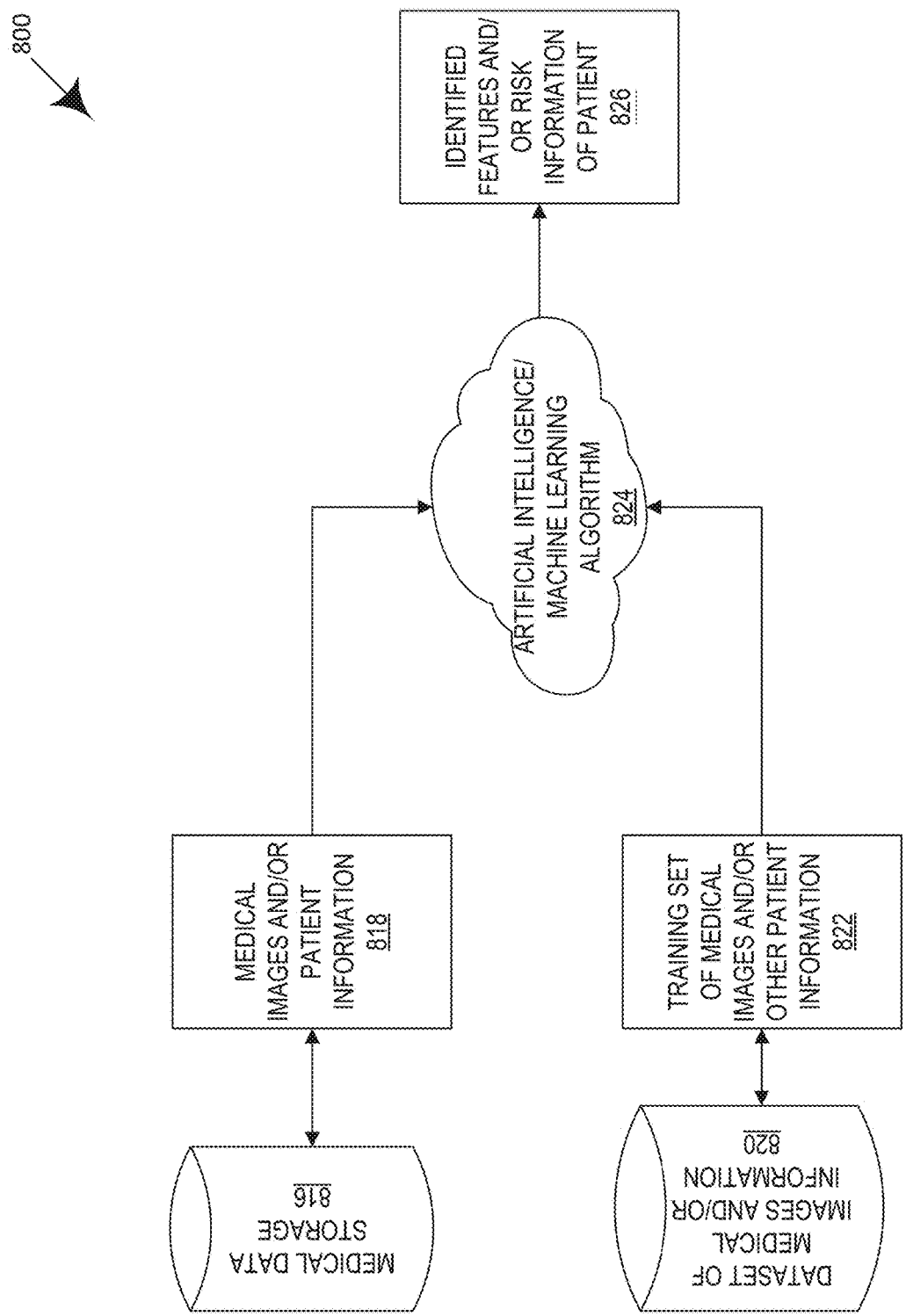
FIG. 5A is a block diagram that illustrates an example process for identifying features of medical images using artificial intelligence or machine learning.

FIG. 5A is a block diagram that illustrates an example of a process and/or system 800 (both referred to here as a "system" for ease of reference) for identifying features and/or risk information of a patient using AI/ML based on non-invasively obtained medical images of the patient and/or patient information. In some embodiments, a current patient's medical data including images and/or patient information is first obtained and electronically stored on medical data storage 816 (e.g., cloud storage, hard disk, etc.). In some embodiments, the system 800 obtains medical images and/or patient information 818 from the medical data storage 816 and preprocesses it, if necessary, for example to reformat it as necessary for further processing. The system 800 can also obtain a training set of medical images and/or patient information 822 from a stored dataset 820 of medical images and/or information of other patients (e.g., hundreds, thousands, tens of thousands, or hundreds of thousands or more of other patients). The medical images and information of other patients can be used to train the AI/ML algorithm 824 prior to processing the medical images and/or patient information 818 of the current patient, as described in further detail in reference to FIGS. 5C and 5D. In some embodiments, the AI/ML algorithm 824 can include one or more NN's, for example, as described in reference to the example NN illustrated in FIG. 6. The ML/AI 824 processes the medical images and/or patient information 818 of the current patient and generates outputs of identified features and/or risk information 826 of the current patient.

Figure 5B:
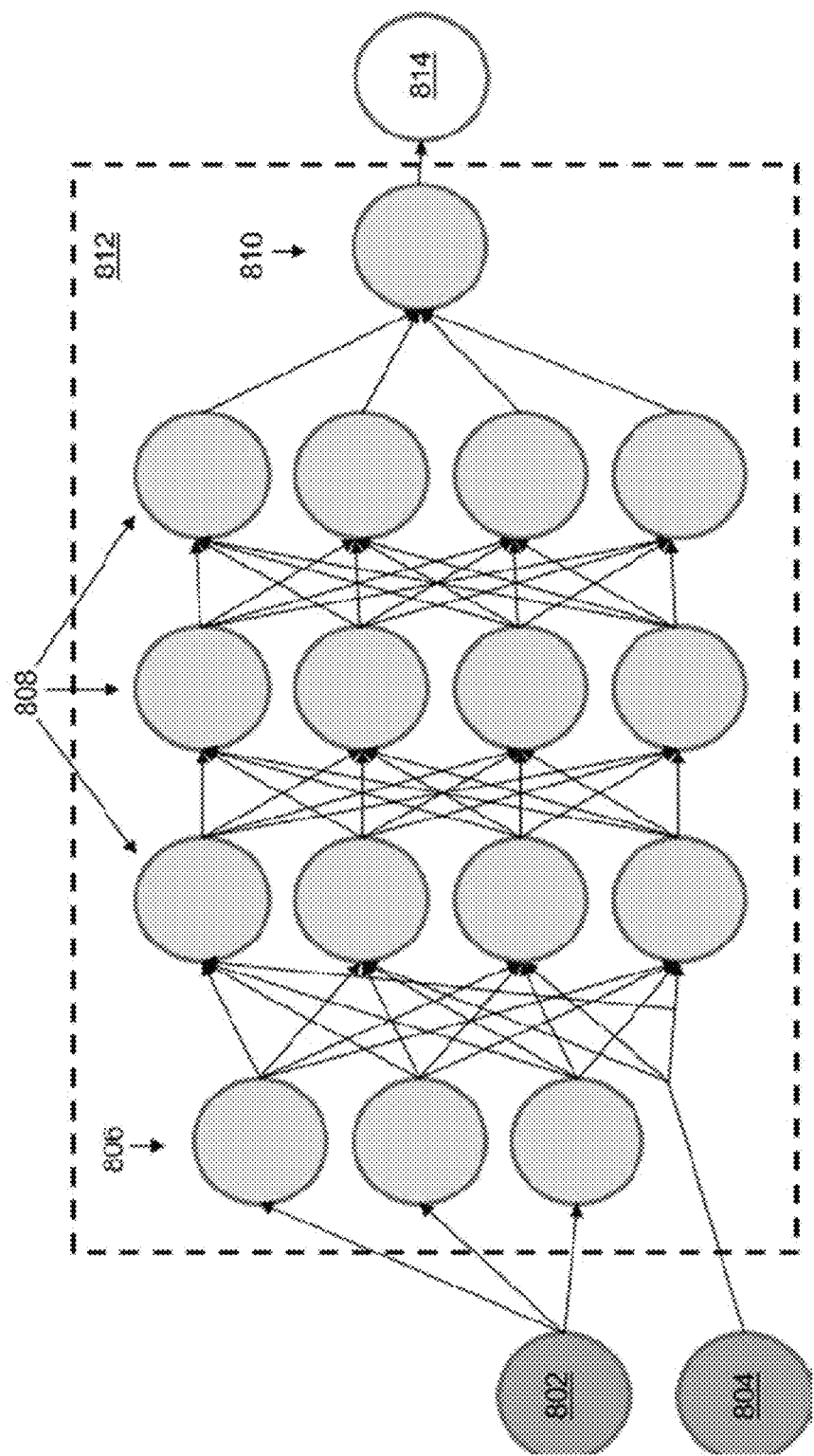
FIG. 5B is a schematic illustrating an example neural network that makes determinations about characteristics of a patient based on medical images.

FIG. 5B is a schematic illustrating an example of a NN 812 that makes determinations 814 about characteristics of a (current) patient based on inputs that include medical images 802. In some embodiments, the NN 812 can be configured to receive other inputs 804. In some embodiments, the other inputs 804 can be medical images of other patients. In some embodiments, the other inputs 804 can be medical history of other patients. In some embodiments, the other inputs 804 can be medical history of the (current) patient. The NN 812 can include an input layer 806. In some embodiments, the NN 812 can be configured to present the training pattern to the input layer 806. In some embodiments, the NN 812 can include one or more hidden layers 808. In some embodiments, the input layer 806 can provide signals to the hidden layers 808, and the hidden layers 808 can receive signals from the input layer 806. In some embodiments, the hidden layers 808 can pass signals to the output layer 810. In some embodiments, one or more hidden layers 808 may be configured as convolutional layers (comprising neurons/nodes connected by weights, the weights corresponding to the strength of the connection between neurons), pooling layers, fully connected layers and/or normalization layers. In some embodiments, the NN 812 may be configured with pooling layers that combine outputs of neuron clusters at one layer into a single neuron in the next layer. In some embodiments, max pooling and/or average pooling may be utilized. In some embodiments, max pooling may utilize the maximum value from each of a cluster of neurons at the prior layer. In some embodiments, back propagation may be utilized, and the corresponding neural network weights may be adjusted to minimize or reduce the error. In some embodiments, the loss function may comprise the Binary Cross Entropy loss function.

In some embodiments, the NN 812 can include an output layer 810. In some embodiments, the output layer 810 can receive signals from the hidden layers 808. In some embodiments, the output layer can generate determinations 814. In some embodiments, the NN 812 can make determinations 814 about characteristics of the patient. In some embodiments, the determinations 814 can include a characterized set of plaque. In some embodiments, the determinations 814 can include a patient's risk of CAD.

Figure 5C:
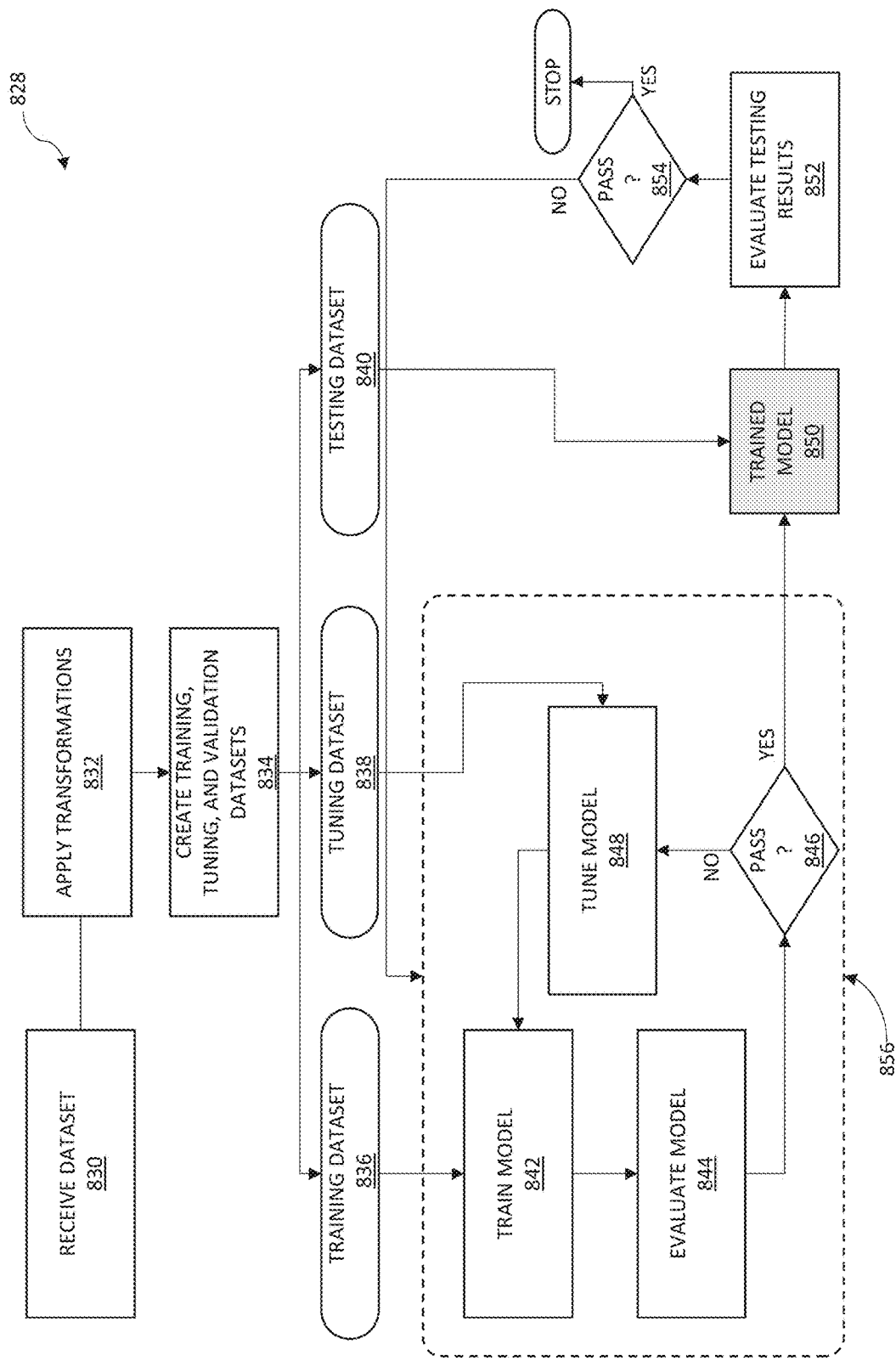
FIG. 5C depicts a flow chart for training an artificial intelligence or machine learning model according to some embodiments.

FIG. 5C depicts an example of a process in a flow diagram for training an artificial intelligence or machine learning model. The process 828 can be performed on a computing system. Various embodiments of such a process for training an AI or ML model can include additional features and/or CAN exclude certain illustrated features (for example, when a transformed/preprocessed dataset is received such that "apply transformations" in block 832 does not need to be performed.)

As illustrated in the example of FIG. 5C, at block 830 the system receives a dataset. At block 832, one or more transformations may be performed on the data in the dataset. In an example, data may require transformations to conform to expected input formats, to conform with expected formatting, e.g., date formatting, units (e.g., pounds vs kilograms, Celsius vs Fahrenheit, inches vs centimeters, etc.), be of a consistent format, and the like. In some embodiments, the data may undergo conversions to prepare it for use in training an AI or ML algorithm, for example, categorical data may be encoded in a particular manner. In some embodiments, nominal data may be encoded using one-hot encoding, binary encoding, feature hashing, or other suitable encoding methods. In some embodiments, ordinal data may be encoded using ordinal encoding, polynomial encoding, Helmert encoding, and so forth. In some embodiments, numerical data may be normalized, for example by scaling data to a maximum of 1 and a minimum of 0 or −1. In some embodiments, a dataset can include images, and the images can undergo resizing, orienting, color correction, deskewing, color space transformations, and so forth. These are merely examples, and the skilled artisan will readily appreciate that other transformations are possible.

At block 834, the system may create, from the received dataset, training, tuning, and testing/validation datasets. In some embodiments, the training dataset 836 may be used during training to determine features for forming a model that can be used for prediction, classification, and so forth. In some embodiments, the tuning dataset 838 may be used to select final models (e.g., final model weights) and to prevent or correct overfitting that may occur during training with the training dataset 836, which can otherwise lead to poor generalization of the model. In some embodiments, the testing dataset 840 may be used after training and tuning to evaluate the model. For example, in some embodiments, the testing dataset 840 may be used to check if the model is overfitted to the training dataset. For example, when iterative training is used, overfitting can be indicated by continued improvement in the model performance on training data (e.g., the loss function or error continues to improve) while performance on a testing dataset improves for some period of time or number of training iterations, but then starts to decrease.

In some embodiments, the system, in training loop 856, may train the model at block 842 using the training dataset 836. In some embodiments, training may be conducted in a supervised, unsupervised, or partially supervised manner. In some embodiments of the present disclosure, supervised training may be used. At 844, in some embodiments, the system may evaluate the model according to one or more evaluation criteria. For example, in some embodiments, the evaluation may include determining how well the model can determine image transformations to account for changes in image acquisition parameters. In other embodiments, the evaluation can include determining how well the model can identify thin cap fibroatheroma. Other uses of AI/ML models are described herein, and different evaluation criteria can be used for different uses. At 846, in some embodiments, the system may determine if the model meets the one or more evaluation criteria. In some embodiments, if the model fails evaluation, the system may, at 848, tune the model using the tuning dataset 838, repeating the training 842 and evaluation 844 until the model passes the evaluation at 846. In some embodiments, once the model passes the evaluation at 846, the system may exit the model training loop 856. In some embodiments, the testing dataset 836 may be run through the trained model 842 and, at block 844, the system may evaluate the results. In some embodiments, if the evaluation fails, at block 846, the system may reenter training loop 856 for additional training and tuning. If the model passes, the system may stop the training process, resulting in a trained model 850. In some embodiments, the training process may be modified. For example, in some embodiments, the system may not use a tuning dataset 838. In some embodiments, the system may not use a testing dataset 840.

In some embodiments, testing can be performed within training loop 856, and training can be stopped once improvement in the model's performance on testing data stops improving or starts to decrease. For example, training can stop to avoid overfitting the model to the training data. In some embodiments, training can stop after a defined number of iterations.

Figure 5D:
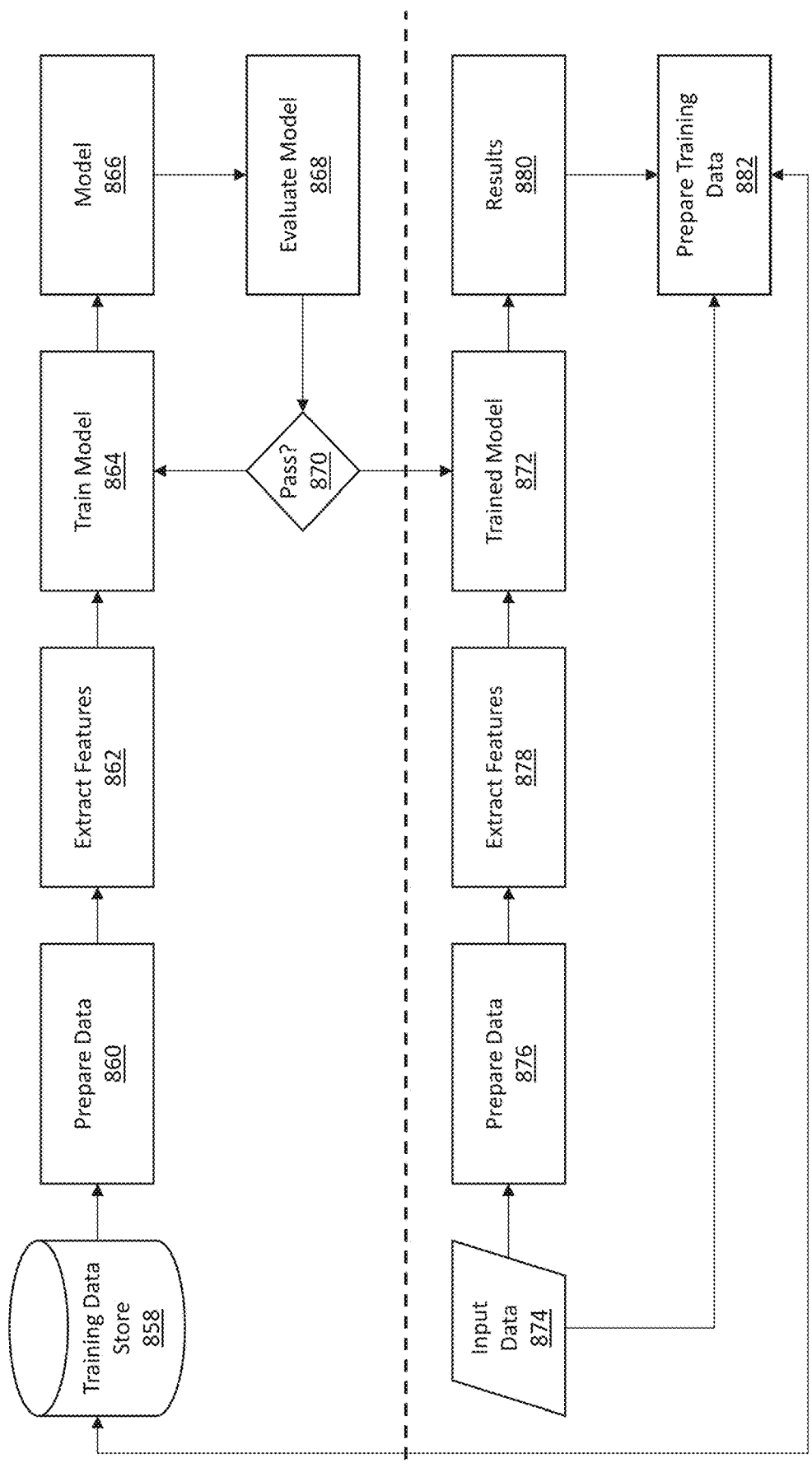
FIG. 5D illustrates an example of training and using an AI/ML model according to some embodiments.

FIG. 5D illustrates an example of a process for training and using an AI/ML model. In some embodiments, training data store 858 can store data for training a model. For example, in some embodiments, training data store 858 can store a patient's medical images and/or information about a patient's physiology, such as weight, BMI, and so forth. At block 860, in some embodiments, a system can be configured to prepare the training data if it was not previously prepared for use in training a model. In some embodiments, as described briefly above, preparing the training data can include performing one or more normalization procedures, standardization procedures, and so forth, such as converting units (e.g., between Fahrenheit and Celsius, between inches and centimeters, between pounds and kilograms), converting dates to a standard format, converting times to a standard format, and so forth, processing images (e.g., size, orientation, color space, etc.). In some embodiments, it can be desirable to exclude certain data as additional data can consume additional computing resources and it can take longer to train a model. However, in some embodiments, exclusions may not be desirable as there can be a risk that a model may not accurately account for the influence of changes in image acquisition parameters on a resulting result. At block 862, the system can extract features from the training data and, at block 864, can train the model using the training data to produce model 866. At block 868, in some embodiments, the system can evaluate the model to determine if it passes one or more criteria. In some embodiments, at decision point 870, if the model fails, the system can perform additional training. In some embodiments, if, at decision point 870, the model passes, the system can make available trained model 872, which can be the model 872 after training is complete.

In some embodiments, the trained model 872 can be used to evaluate a particular patient. The input data 874 can relate to a specific input for which the outputs of the trained model 872 are desired. At block 876, the system can prepare the input data 874, for example as described above in relation to the stored training data. In some embodiments, at block 878, the system can extract features from the prepared user data. In some embodiments, the system can be configured to feed the extracted features to the trained model 872 to produce results 880.

In some embodiments, the input data 874, the results 880, and/or other information can be used to train the model. At block 882, in some embodiments, the system can prepare the input data 874 and the results 880 for use in training the model 872. In some embodiments, the system can store the prepared data in training data store 858. In some embodiments, the prepared data can be stored, additionally or alternatively, in another database or data store. In some embodiments, the system can retrain the model periodically, continuously, or whenever an operator indicates to the system that the model should be retrained. Thus, in some embodiments, the trained model 872 can evolve over time, which can result in improved performance of the model (e.g., improved predictive capability, improved classification capability, and so forth) over time.

A dataset used for training or testing can include, for example, CT images, coronary computed tomography angiography (CCTA) images, extracted vessels, image acquisition parameters, patient information (e.g., patient identifier, patient weight, patient body mass index, etc.), and/or any other relevant information.

In some embodiments, a machine learning model can be trained using supervised learning, where the training data includes input data (e.g., images, patient information, etc.) as input and a desired output (e.g., classifications, stratifications, labels, etc.), for example a risk assessment, labeled coronary artery tree, etc. . . . . A representation of the input data can be provided to the model. Output from the model can be compared to the desired output. For example, in a classification model, the desired output can be the true classification of the input, which can be compared with a classification determined by the model. In some embodiments, based on the comparison, the model can be modified, such as by changing weights associated with nodes of the neural network or parameters of the functions used at each node in the neural network (e.g., applying a loss function). The model can be modified until it produces the desired output with a desired level of accuracy.

Computer System

Figure 6:
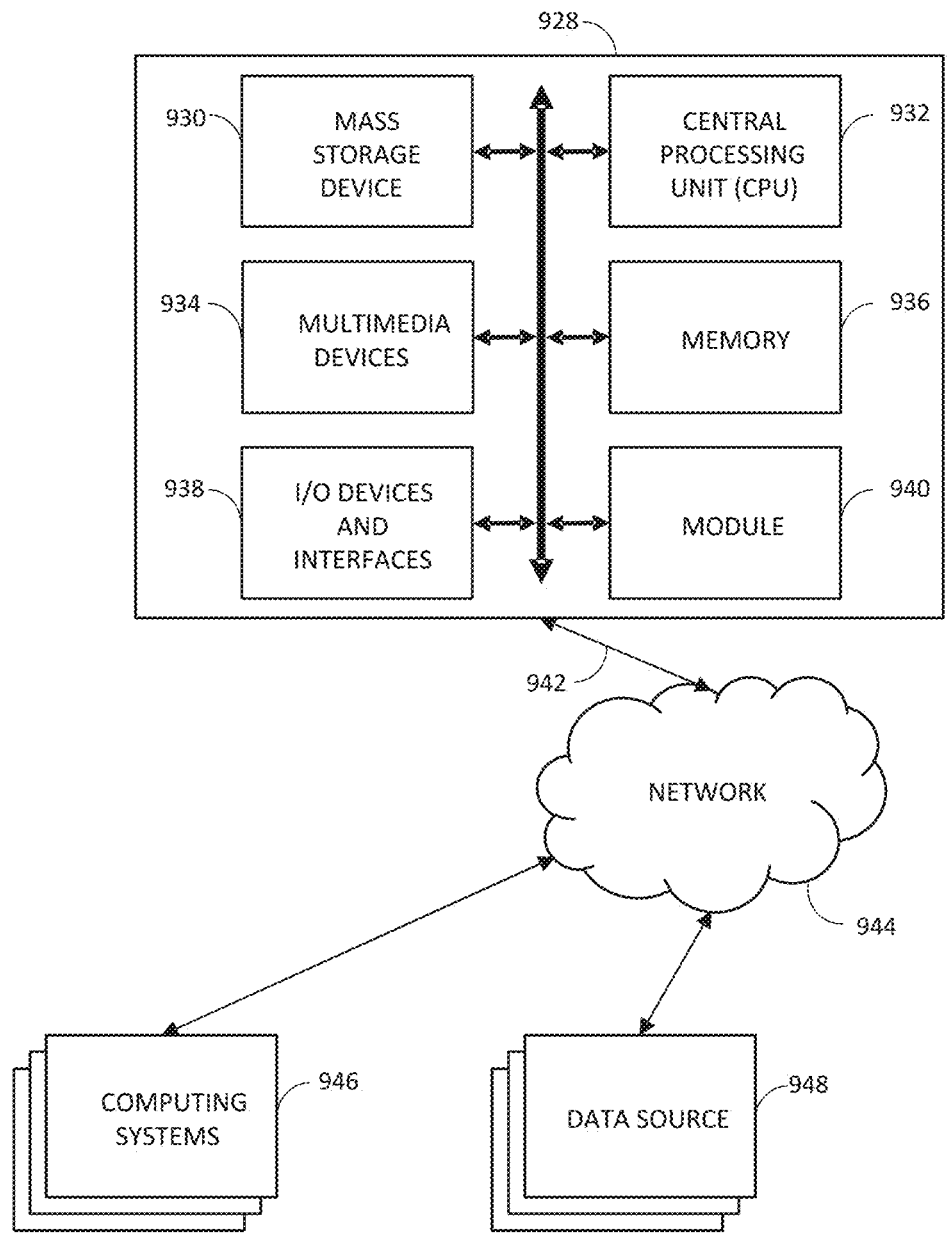
FIG. 6 is a block diagram depicting an embodiment of a computer hardware system configured to run software for implementing one or more embodiments of systems, methods, and devices described herein.

In some embodiments, the systems, processes, and methods described herein are implemented using a computing system, such as the one illustrated in FIG. 6. The example computer system 928 is in communication with one or more computing systems 946 and/or one or more data sources 948 via one or more networks 944. While FIG. 5A illustrates an embodiment of a computing system 928, it is recognized that the functionality provided for in the components and modules of computer system 928 can be combined into fewer components and modules, or further separated into additional components and modules.

The computer system 928 can comprise a Plaque Analysis Module 940 that carries out the functions, methods, acts, and/or processes described herein. The Plaque Analysis Module 940 executed on the computer system 928 by a central processing unit 306 discussed further below.

In general the word "module," as used herein, refers to logic embodied in hardware or firmware or to a collection of software instructions, having entry and exit points. Modules are written in a program language, such as JAVA, C#, C, or C++, or the like. Software modules can be compiled or linked into an executable program, installed in a dynamic link library, or can be written in an interpreted language such as JavaScript, BASIC, PERL, LUA, PHP, or Python and any such languages. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within specially designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 928 includes one or more processing units (CPU) 932, which can comprise a microprocessor. The computer system 928 further includes a physical memory 936, such as random access memory (RAM) for temporary storage of information, a read only memory (ROM) for permanent storage of information, and a mass storage device 930, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 928 are connected to the computer using a standards-based bus system. The bus system can be implemented using various protocols, such as Peripheral Component Interconnect (PCI), PCI Express, Micro Channel, SCSI, Industrial Standard Architecture (ISA) and Extended ISA (EISA) architectures.

The computer system 928 includes one or more input/output (I/O) devices and interfaces 938, such as a keyboard, mouse, touch pad, and printer. The I/O devices and interfaces 938 can include one or more display devices, such as a monitor, which allows the visual presentation of data to a user. More particularly, a display device provides for the presentation of GUIs as application software data, and multi-media presentations, for example. The I/O devices and interfaces 938 can also provide a communications interface to various external devices. The computer system 928 can comprise one or more multi-media devices 934, such as speakers, video cards, graphics accelerators, and microphones, for example.

Computing System Device/Operating System

The computer system 928 can run on a variety of computing devices, such as a server, a Windows server, a Structure Query Language server, a Unix Server, a personal computer, a laptop computer, and so forth. In other embodiments, the computer system 928 can run on a cluster computer system, a mainframe computer system and/or other computing system suitable for controlling and/or communicating with large databases, performing high volume transaction processing, and generating reports from large databases. The computing system 928 is generally controlled and coordinated by an operating system software, such as z/OS, Windows, Linux, UNIX, BSD, SunOS, Solaris, macOS, iOS, iPadOS, or other compatible operating systems, including proprietary operating systems and/or open source operating systems. Operating systems control and schedule computer processes for execution, perform memory management, provide file system, networking, and I/O services, and provide a user interface, such as a graphical user interface (GUI), among other things.

Network

The computer system 928 illustrated in FIG. 6 is coupled to a network 944, such as a LAN, WAN, or the Internet via a communication link 942 (wired, wireless, or a combination thereof). Network 944 communicates with various computing devices and/or other electronic devices. Network 944 is communicating with one or more computing systems 946 and one or more data sources 948. The Plaque Analysis Module 914 can access or can be accessed by computing systems 946 and/or data sources 948 through a web-enabled user access point. Connections can be a direct physical connection, a virtual connection, and other connection type. The web-enabled user access point can comprise a browser module that uses text, graphics, audio, video, and other media to present data and to allow interaction with data via the network 944.

The output module can be implemented as a combination of an all-points addressable display such as a cathode ray tube (CRT), a liquid crystal display (LCD), a plasma display, or other types and/or combinations of displays. The output module can be implemented to communicate with input devices 938 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

Other Systems

The computing system 928 can include one or more internal and/or external data sources (for example, data sources 948). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 928 can also access one or more databases 948. The databases 948 can be stored in a database or data repository. The computer system 928 can access the one or more databases 948 through a network 944 or can directly access the database or data repository through I/O devices and interfaces 938. The data repository storing the one or more databases 948 can reside within the computer system 928.

URLs and Cookies

In some embodiments including any of the embodiments disclosed herein (above or below) one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Normalization of Medical Images for Plaque Analysis and Vascular Analysis—8006

Described herein are systems, methods, and devices for normalizing medical images, such as for coronary plaque analysis, vascular analysis, and/or the like. In some embodiments, the systems, methods, and devices herein can be configured to utilize one or more AI/ML models for normalizing medical images.

Cardiology patients, such as those who suffer from heart disease, may undergo serial imaging procedures (e.g., annual imaging procedures, quarterly imaging procedures, etc.). Imaging procedures can include, for example, computed tomography (CT) imaging, for example coronary computed tomography angiography (CCTA) imaging. It can be significant to compare images collected over time, for example to determine whether a patient's condition is stable, improving, or getting worse. However, comparing images over time can present significant challenges. For example, different imaging equipment may be used, different image acquisition parameters can be used when collecting images (e.g., different integration times, x-ray intensity, x-ray energy, peak kilovoltage (kVp), current (mA), and so forth). In some cases, a patient's physiology may change. For example, a patient may gain or lose weight, which can affect the attenuation of x-rays by tissue. In some cases, a patient's hydration level can impact x-ray attenuation. Additionally, tissue is generally not rigid and may move depending on the patient's position, breathing, heartbeat, etc. Accordingly, it can be difficult to co-register two serial imaging scans and/or to determine clinically significant differences between the two scans (as opposed to, for example, differences that arise because of different imaging conditions or unrelated changes to patient physiology). Without a reliable standard or other way of ensuring a meaningful comparison between images, it can be difficult to determine changes in plaque, lumen measurements, lumen composition, and so forth.

One approach to normalizing images collected at different times is to use a physical calibration device during an imaging procedure. A physical calibration device can include, for example, one or more standards, such as water, which can be imaged at the same settings as the image of the patient. In some cases, a standard can include a sticker or patch worn by the patient during the imaging procedure. In some cases, images of physical calibration devices can be compared between imaging procedures, which can inform how the patient images should be adjusted to account for differences in imaging conditions. However, there are several drawbacks to such approaches. For example, imaging the physical calibration device can add time to an imaging procedure, consume additional storage space, and so forth. In some cases, an individual may have to spend time adjusting the physical calibration device images to determine how to adjust the patient images. When a sticker is placed on a patient's body, placement of the sticker can add extra time and steps to an imaging procedure, different placement of the sticker may impact the apparent electromagnetic properties of the sticker, and so forth.

Imaging results can depend on a variety of imaging parameters as well as on the physiology of the patient. For example, imaging results can vary depending on the method of helical CT scanning (e.g., single source, dual source, multi-source, rapid switching, fast pitch helical), the type of detector (e.g., energy integrating or photon counting), the type of energy used (e.g., single energy or dual energy), the current through the x-ray generator (mA), the peak kilovoltage (kVp), the image noise, the signal level, the signal to noise ratio, contrast opacification, contrast to noise ratio, and so forth.

According to some embodiments, an image normalization algorithm can be provided. For example, in some embodiments, a database, data store, or other source of data can include a large number of previously-captured images. In some embodiments, each patient represented in the data store can have undergone more than one imaging procedure using different image acquisition parameters. In some embodiments, a polynomial regression can be carried out to determine how to normalize a second scan based on a first scan, such that direct comparisons can be made between the first scan and the second scan.

As described herein, there can be a large number of variables that can affect an image, including settings of an imaging device (e.g., a CT scanner) and/or changes in patient physiology over time. An image may vary linearly with some variables but may vary nonlinearly with other variables. Thus, carrying out a polynomial regression to develop an image processing algorithm may be difficult or even infeasible. In some embodiments, an AI/ML model can be used to generate an image processing algorithm and/or can be used to process images. For example, in some embodiments, an AI/ML model can be trained by providing sets of images with different known image acquisition parameters and/or patient physiological parameters to the model and training the model to determine modifications that should be made to an image to account for difference in one or more image acquisition parameters and/or one or more differences in patient physiology.

In some embodiments, scan normalization can be carried out using a single model for all imaging systems (e.g., for all CT scanners). However, such an approach can require a relatively large number of samples to obtain reliable ground truth information that can be broadly applied to different CT scanners or other imaging devices. Additionally, a model that is generalized for all CT scanners or other imaging devices may be relatively complex as compared with models for specific CT scanners, specific models of CT scanner, etc. In some implementations, a normalization model for an individual CT scanner can be set or otherwise configured at the time of onboarding. In some embodiments, a normalization model can be shared by CT scanners of a particular model or group of models (e.g., multiple models of CT scanner may have the same or very similar imaging hardware). In some implementations, however, even individual scanners of the same model can perform somewhat differently. Thus, it can be important to ensure that the normalization model accurately normalizes images for a particular CT scanner. In some embodiments, a normalization model can be tuned for a specific CT scanner. In some embodiments, a normalization model, whether specific to a particular scanner, specific to a model of scanner, or otherwise, can be periodically tuned to maintain and/or improve performance of the normalization model.

Normalization challenges are not necessarily limited to image acquisition conditions, patient physiology, etc. For example, in some cases, image reconstruction algorithms can affect apparent intensity, for example depending upon a voxel definition, type of iterative reconstruction, and so forth. In some cases, noise levels in an image can affect normalization. In some embodiments, reconstruction approaches can be standardized, which can ensure relatively consistent effects of image reconstruction algorithms.

In some embodiments, image normalization can be carried out on a global level, for example without regard to the anatomical feature present in an image. In some embodiments, image normalization can be carried out at a more localized level, which can help to account for, for example, localized effects of blooming at so forth.

There can be many different CT scanners, many different imaging parameters, and so forth. In some embodiments, images from real imaging procedures can be used in training an AI/ML model for image normalization and/or in determining parameters for a polynomial regression. In some embodiments, additionally or alternatively, images can be simulated with different imaging parameters. The use of simulated images can significantly expand the number of images that can be used, the variety of imaging parameters that can be used, and so forth which may, in some cases, result in improved models or polynomial regressions.

In some embodiments, a system can be configured to present a default normalization to a user. In some embodiments, the system can provide an interface, configuration file, etc., that can enable the user to adjust normalization settings, thereby enabling a user to use their expert judgment to optimize and/or customize image normalization.

Coronary Artery Disease Risk Stratification/*8007*/

Also disclosed herein are systems, methods, and devices for image-based coronary artery disease (CAD) risk stratification. In some embodiments, the systems, methods, and devices described herein can be configured to integrate one or more inputs of stenosis, atherosclerosis, ischemia, or a combination thereof to determine and/or to facilitate determination of risk stratification of a CAD of a subject. In some embodiments, additional information can be input, such as information about (e.g., placement, diameter, length, type of stent, etc.) In some embodiments, the systems, methods, and devices described herein can be configured to utilize one or more AI/ML algorithms to combine and/or consider one or more inputs of stenosis, atherosclerosis, ischemia, additional information, or any combination thereof, to determine and/or to facilitate determination of risk stratification of CAD of a subject. In some embodiments, the systems, methods, and devices described herein are configured to provide a prognosis of a risk of CAD of a subject and/or likelihood of a major adverse cardiovascular event (MACE) occurring in a subject. In some embodiments, the approaches described herein can be used to determine a predicted prognosis based on one or more possible treatments, such as stenting, treatment with medications, changes in diet, changes in exercise, etc. In some embodiments, the approaches herein can be used to determine prognoses over time. For example, a physician may consider short and long term benefits and risks of a particular treatment approach.

Current solutions and/or techniques for risk stratification of CAD do not take into account the totality of the circumstances, including but not limited to stenosis, atherosclerosis, ischemia, or any combination thereof. To address such technical shortcomings, some embodiments of the systems, methods, and devices described herein are configured to integrate and/or account for one or more inputs of stenosis, atherosclerosis, ischemia, or a combination thereof, and/or additional inputs, such as potential treatments, to provide improved and/or more accurate risk stratification and/or staging of CAD of a subject.

In some embodiments, the systems, methods, and devices described herein can be configured to be used to screen symptomatic and/or asymptomatic subjects for risk stratification of CAD. In some embodiments, the systems, methods, and devices described herein can be configured to provide prognostic outputs for MACE. In some embodiments, the systems, methods, and devices described herein can be configured to provide prognostic outputs for MACE which are superior to the atherosclerosis cardiovascular disease (ASCVD) risk score or ASCVD risk calculator. In some embodiments, the systems, methods, and devices described herein can be configured to provide prognostic outputs for MACE that improve upon and/or are superior to the ASCVD risk score or risk calculator in terms of positive predictive value (PPV) by stage of disease or CAD. In some embodiments, the systems, methods, and devices described herein can be configured to provide prognostic outputs for MACE that comprise a disease stage-based hazards ratio, for example with a 95% or greater confidence interval. Prognostic outputs for MACE obtained via the approaches described herein may show an improved and/or superior integrated discrimination improvement (IDI) index compared to the ASCVD risk score or risk calculator. In some embodiments, the systems, methods, and devices described herein can be configured to output a CAD staging system and/or CAD risk stratification system that improves patient outcomes. In some embodiments, the systems, methods, and devices described herein can be configured to output a CAD staging system and/or CAD risk stratification system that directs guideline-directed treatment tailored to underlying disease risk (e.g., CAD risk) to prevent or reduce the likelihood of MACE.

In some embodiments, the systems, methods, and devices described herein are configured to generate a CAD stage for a subject. In some embodiments, the systems, methods, and devices described herein are configured to classify and/or generate a CAD stage for a subject. In some embodiments, the CAD stage can be ordinal, for example where the system determines that a subject has CAD risk corresponding to stage 0, stage 1, stage 2, or stage 3. In some embodiments, the system can be configured to determine a subject to have stage 0 CAD risk when the subject's total plaque volume or other plaque volume is about 0 mm$^3$. In some embodiments, the system can be configured to determine a subject to have stage 1 CAD risk when the subject's total plaque volume or other plaque volume is between about 1 and about 250 mm$^3$. In some embodiments, the system can be configured to determine a subject to have stage 2 CAD risk when the subject's total plaque volume or other plaque volume is between about 251 and about 750 mm$^3$. In some embodiments, the system can be configured to determine a subject to have stage 3 CAD risk when the subject's total plaque volume or other plaque volume is above about 750 mm$^3$. In some embodiments, the systems, devices, and methods described herein are configured to output a CAD risk assessment of the subject that is continuous. That is, in some embodiments, the system can be configured to generate a number or value on a continuous scale that is representative of CAD risk for the subject. In some embodiments, an end user (e.g., a physician) can adjust thresholds that differentiate between different CAD stages.

In some embodiments, the systems, methods, and devices described herein can be configured to increase, decrease, bump up or down, or otherwise modify CAD risk assessment or stratification of a subject that was previously generated, for example based on plaque volume or total plaque volume. For example, in some embodiments, the system can be configured to increase or bump up or otherwise modify a CAD risk assessment or stage for a subject when severe stenosis is found in a certain location or coronary artery, for example in the left main coronary artery (LMCA), right coronary artery (RCA), right marginal artery, left coronary artery, circumflex artery, left obtuse marginal artery, left anterior descending artery, proximal left anterior descending artery, or diagonal arteries. In particular, in some embodiments, the system can be configured to increase or bump up or otherwise modify a CAD risk assessment or stage for a subject when severe stenosis is found in the left main or proximal LAD. In some embodiments, the system can be configured to increase or bump up or otherwise modify a CAD risk assessment or stage for a subject when ischemia or likelihood of ischemia is found in any one or more of the coronary aforementioned arteries.

In some embodiments, the system can be configured to bump up or down or increase or decrease or otherwise modify CAD risk assessment or stratification on a continuous scale and/or by 1, 2, 3, or more stages on an ordinal scale. In some embodiments, the system is configured to bump up a stage by a limited number of stages, for example only by 1 or 2 stages, regardless of the number of stenoses and/or ischemia found.

In some embodiments, the systems, methods, and devices described herein are configured to combine one or more of atherosclerosis, plaque, stenosis, and/or ischemia to generate a CAD risk assessment or stratification or classification of a subject. In some embodiments, the system can be configured to combine one or more of atherosclerosis, plaque, stenosis, and/or ischemia by utilizing one or more ratios, exponents, any mathematical function, logarithmic equation, algorithmic equation, and/or machine learning. In some embodiments, the generated CAD risk assessment or stratification can comprise one or more of a value on a continuous scale, staging, or classification.

In some embodiments, the systems, methods, and devices can be configured to utilize any one or more plaque characteristics discussed herein in generating a CAD risk stratification, including for example amount or type of plaque, location, remodeling, embeddedness in other types of plaque, distance from a plaque to the vessel or lumen wall, or shape.

In some embodiments, the systems, methods, and devices herein can be configured to take into account stenosis when generating a CAD risk assessment or stratification. In some embodiments, the system can be configured to utilize stenosis in a binary form, for example as either the presence or absence of stenosis. In some embodiments, the system can be configured to utilize as an input the presence or absence of severe and/or non-severe stenosis, for example with a predetermined cutoff value. In some embodiments, the system can be configured to utilize as an input severity of stenosis on a continuous, stepwise, or ordinal scale.

In some embodiments, the systems, methods, and devices herein can be configured to take into account ischemia in generating a CAD risk assessment or stratification. In some embodiments, the system can be configured to utilize ischemia in a binary form, for example as the presence or absence or the likelihood of presence or absence of ischemia (e.g., likely or not likely). In some embodiments, the system can be configured to utilize as an input the presence or absence of severe and/or non-severe ischemia, for example with a predetermined cutoff value. In some embodiments, the system can be configured to utilize as an input severity of ischemia on a continuous, stepwise, and/or ordinal scale, for example using AI-based fractional flow reserve or AI-FFR.

In some embodiments, the systems, methods, and devices described herein can be configured to combine analysis of plaque, stenosis, ischemia, and/or pericoronary adipose tissue in generating a risk stratification or assessment of CAD for a subject. In some embodiments, the system can be configured to also take into account the percentage of subtended myocardium, perfusion, and/or endothelial wall shear stress in generating a risk stratification or assessment of CAD for a subject. In some embodiments, additional factors may be taken into account, such as treatments which can include lifestyle changes, medication, and/or surgical intervention.

In some embodiments, the systems, methods, and devices described herein can be configured to bump up or down, increase or decrease, or otherwise modify CAD risk stratification or assessment based solely on image analysis. In some embodiments, the systems, methods, and devices described herein can be configured to bump up or down, increase or decrease, or otherwise modify CAD risk stratification or assessment based on image analysis and in combination with one or more other factors, such as for example a lab test, symptoms of a subject, biometrics, risk factors, and/or molecular diagnostics.

In some embodiments, the systems, methods, and devices described herein can be configured to generate a CAD risk assessment or stratification based on an ordinal scale or continuous scale. In some embodiments, the systems, methods, and devices described herein can be configured to generate a CAD risk assessment on an absolute scale or relative scale, for example compared to normal risk levels in a reference population, such as one determined based at least in part on similar demographics, such as gender or age, of the subject.

In some embodiments, the systems, methods, and devices described herein can be configured to generate a CAD risk assessment or stratification that is tied to a specific time horizon for MACE. For example, the CAD risk assessment can be based on the likelihood of a MACE occurring within a certain time frame. In some embodiments, the timeframe can be about 3 months, about 6 months, about 1 year, about 1.5 years, about 2 years, about 2.5 years, about 3 years, about 3.5 years, about 4 years, about 4.5 years, about 5 years, about 5.5 years, about 6 years, about 6.5 years, about 7 years, about 7.5 years, about 8 years, about 8.5 years, about 9 years, about 9.5 years, about 10 years, and/or within a range defined by two of the aforementioned values.

In some embodiments, a risk stratification model can consider various additional and/or alternative information for determining risk stratification. For example, in some embodiments, a system can be configured to use perfusion data (e.g., as obtained using MRI) to determine ischemia. In some embodiments, the system can be configured to use myocardial bloodflow (e.g., as determined via SPECT) to determine ischemia. In some embodiments, a system can be configured to use intravascular ischemia data as determined via invasive FFR, which can provide information relating to stenosis. In some embodiments, intravascular ischemia data can provide information relating to plaque. In some embodiments, an AI/ML model can be provided with anatomic inputs to determine physiology, which can provide information about stenosis, plaque, ischemia, or any combination thereof. In some embodiments, a machine learning model can be trained to predict MACE. For example, a model can be trained using data relating to Type I myocardial infarction, Type II myocardial infarction, stroke, and so forth.

In some embodiments, a prognosis can vary depending on any treatment provided to the patient, such as changes in diet or exercise, medication, local intervention such as stenting, and so forth. In some embodiments, a prognosis can vary depending on a stent length, stent diameter, stent placement, etc. For example, as described in more detail herein, stent choice and placement can have a significant impact on patient outcomes. For example, if a stent is too short, restenosis can be more likely to occur. If a stent is too wide as compared with the diameter of the vessel in which it is placed, there can be a greater likelihood that the vessel ruptures. If a stent is improperly placed, there can be negative consequences such as in-stent restenosis.

In some embodiments, an interventionist may utilize the systems, methods, and devices described herein to aid in selecting a stent and/or to aid in planning a surgical procedure to place the stent. In some embodiments, the interventionist can use the approaches described herein to determine prognoses for different stents, different surgical plans (e.g., different placement of the stent), and so forth.

Plaque Regression Classification

Plaques can change in size for a variety of reasons. For example, a plaque can become smaller due to densification and/or due to the total mass of the plaque decreasing. A decrease that is attributable (or a threshold amount of which is attributable) to a change in the total mass of plaque can be classified as a true regression. Other changes in plaques can be classified as pseudo regressions. It can be difficult to distinguish between true regression and pseudo regression. For example, if humans determine whether a plaque is a true regression or pseudo regression, different observers can vary in how they determine plaque volume, how they determine plaque density, and so forth. Even the same observer can have variation in how they determine plaque volume, plaque density, and so forth. This intra-observer and/or inter-observer variation can lead to unreliable and/or inconsistent determinations of whether a plaque regression is a true regression or a pseudo regression. In some embodiments, the normalization approaches described herein can be used to improve the accuracy, consistency, and/or reproducibility of regression classification.

Disclosed herein are systems, methods, and devices for determining regression and/or stabilization of plaque, such as coronary plaque or atherosclerotic plaque, for example over time and/or post-treatment. In some embodiments, the systems, methods, and devices, described herein are related to plaque analysis to distinguish between true or true regression vs. pseudo regression of plaque, such as coronary plaque. In some embodiments, pseudo regression of plaque can be characterized as a reduction in plaque volume due to increased densification (for example, similar to a fluffy cotton candy becoming balled up or denser) as opposed to a true reduction in plaque volume with relatively consistent material density. In some embodiments, pseudo regression in plaque volume can be characterized as reduction in plaque volume where the material density of plaque has increased above a predetermined threshold amount or percentage. In some embodiments, true regression in plaque volume can be characterized as reduction in plaque volume where the material density has remained constant or relatively constant or has not increased and/or changed by more than a predetermined threshold amount or percentage. In some embodiments, true regression can be characterized as a reduction in plaque volume and mass. In some embodiments, pseudo regression can be characterized as a reduction in volume without a decrease in mass. In some embodiments, the approaches herein can be used to differentiate between more than pseudo regression and true regression. For example, in some embodiments, the approaches herein can be used to classify a change in plaque as a true regression, pseudo regression, stasis, or growth. Stasis can be characterized as the plaque size (e.g., plaque volume) remaining constant or approximately constant or changing by less than a threshold amount. Growth can be characterized as an increase in plaque size (e.g., plaque volume) above a threshold amount (e.g., greater than 0%, greater than 5%, greater than 10%, or any other value between these values, or more).

In some embodiments, true plaque regression and pseudo plaque regression can be determined based on comparison of the change in plaque volume and the change in plaque density, for example based on the mathematical product of plaque volume and plaque density (e.g., plaque mass). For example, if the overall mass of a plaque has decreased, this can indicate a true regression, while if the overall mass of the plaque has stayed constant or approximately constant or increased, this can indicate pseudo regression or continued growth of the plaque. In some embodiments, a material mass can be determined by determining a material density of a plaque based on the radiodensity of the plaque and multiplying the material density by the volume of the plaque. In some embodiments, material mass may not be computed. For example, instead of converting radiodensity to material density and multiplying the material density by the plaque volume, a proxy for mass can be computed by multiplying the radiodensity by the plaque volume.

In some cases, being able to distinguish between pseudo plaque regression and true plaque regression can be important for clinical tracking, decision making, and so forth. For example, in some embodiments, both pseudo regression in plaque volume and true regression in plaque volume can be considered beneficial for a patient. However, there can be clinically relevant differences between the two. As one example, if most plaque in a patient comprises calcified plaque, then pseudo regression in plaque volume might be considered less of an improvement or decline in patient risk of CAD or MACE as compared with true regression in plaque volume. However, if most plaque in a patient comprises non-calcified plaque, low density non-calcified plaque, or a combination of both, pseudo regression in plaque volume may be considered as indicating an improvement or decline in patient risk of CAD or MACE that is the same as or similar to that of a true regression in plaque volume, as calcification of plaque can provide some benefit. As described herein, this can be the case within certain limitations. For example, high-risk plaques (e.g., low-density non-calcified plaques) made up of fat and fibrous tissue can have a higher likelihood of rupture, which can cause, for example, myocardial infarction and/or blood clots, can present a greater danger to a patient than non-calcified plaques (which can be less likely to rupture). Calcified plaques can be comprised mostly of calcium and can be least likely to rupture. Thus, when a non-calcified plaque becomes calcified, the risk associated with the plaque can decrease. However, further densification or calcification of an already-calcified plaque may confer little or no reduced risk to a patient.

In some embodiments, true regression in plaque volume, pseudo regression in plaque volume, or both can be influenced by one or more external factors or treatments, such as age, gender, exercise (exercise intensity, exercise duration, exercise frequency), diet, treatment with medications (e.g., statins, PCSK-9 inhibitors), surgical interventions (e.g., stenting), the like, or any combination thereof.

In some embodiments, the systems, methods, and devices herein can be configured to analyze a medical image to determine and/or distinguish between true plaque regression, pseudo plaque regression, etc. In some embodiments, the systems, methods, and devices described herein can be configured to determine and/or distinguish between true plaque regression and/or pseudo plaque regression based at least in part on a change in total plaque volume and a change in density or radiodensity distribution of plaque over time or between two or more points in time. In some embodiments, the systems, methods, and devices described herein can be configured to determine and/or distinguish between true plaque regression, pseudo plaque regression, etc., based at least in part on one or more of a change in total plaque volume, area, or length, change in low density non-calcified plaque volume, area, or length, change in non-calcified plaque volume, area, or length, change in calcified plaque volume, change in material density, change in radiodensity, or change in Hounsfield unit density distribution of one or more aforementioned types of plaque over time or between two or more points in time.

In some embodiments, the systems, methods, and devices described herein can be configured to utilize and artificial intelligence (AI) and/or machine learning (ML) algorithm (also referred to herein as a model) trained on a dataset comprising known distinctions between true regression in plaque volume and pseudo regression in plaque volume. For example, in some embodiments, a set of images showing known true regression and pseudo regression can be labeled as true regression or pseudo regression and can be used to train a machine learning model to classify regression as true regression or pseudo regression. In some embodiments, specific features can be identified for determining plaque regression type. In some embodiments, a user may not identify specific features, but may instead provide a relatively large number of features to a machine learning model.

Local Treatment and Systemic Treatment Guidance

Also described herein are systems, methods, and devices for guiding local treatment, systemic treatment, or both using image-based plaque analysis. In some embodiments, the systems, methods, and devices described herein are related to image-based analysis of one or more regions of plaque, such as coronary plaque, based on one or more distances, volumes, densities, radiodensities, shapes, morphologies, embeddedness, axes measurements, or any combination thereof. For example, in some embodiments, the systems, methods, and devices described herein are related to using one or more analyses of plaque to determine or guide the determination of local treatment, systemic treatment, or both, of plaque for a patient. In some embodiments, the systems, methods, and devices described herein are configured to utilize AI/ML as described in more detail herein.

In some embodiments, the systems, methods, and devices described herein can be configured to determine and/or guide determination of local plaque treatment, systemic plaque treatment, or both, for a particular patient based at least in part on image-based analysis of plaque (e.g., coronary plaque) from a medical image (e.g., a CT image). In some embodiments, the systems, methods, and devices described herein can be used to determine a patient-specific treatment or therapy. In some embodiments, the treatment or therapy can include local treatment, systemic treatment, or both. For example, in some embodiments, local treatment can include one or more of percutaneous stenting, percutaneous coronary intervention (PCI), coronary artery bypass grafting (CABG), and/or the like to target treatment at one or more particular regions of plaque. In some embodiments, systemic treatment can include one or more of medical therapy, medication, diet, physical exercise, and/or the like. Systemic treatments can target all plaque as a whole. In some embodiments, the systems, methods, and devices described herein can be configured to determine whether combined local treatment and systemic treatment, local treatment alone, or systemic treatment alone is recommended for a particular patient based on image-based plaque analysis. In some embodiments, additional information can be considered, such as a patient's weight, activity level, age, and so forth. For example, if a patient already exercises regularly, a recommendation for more exercise may be unlikely to be helpful to the patient. As another example, a patient with mobility issues may not be able to make certain changes to exercise.

In some embodiments, the systems, methods, and devices described herein can be configured to recommend a particular local treatment, systemic therapy, or both for a patient in order to improve coronary artery disease (CAD) prognosis, coronary plaque, ischemia, atherosclerosis, or any combination thereof. In some embodiments, the systems, methods, and devices herein can be configured to recommend one or more particular local treatments, systemic therapies, or any combination thereof for a patient in order to improve a hard outcome such as the prevention of death, myocardial infarction, or other adverse outcome. In some embodiments, the systems, methods, and devices herein can be configured to output a plurality of treatment options to a user (e.g., a physician) to provide guidance to the physician for determining a treatment plan.

In some embodiments, the systems, methods, and devices herein can be configured to use a generated lesion-level risk score to guide or recommend medical decision making in a manner that provides therapeutic benefit via local mechanical treatment with percutaneous coronary intervention (PCI) and/or with a minimal or otherwise appropriate level of systemic treatment. For example, in some cases, as lesions treated with PCI may represent the sole lesions, systemic treatment may not be warranted. In some cases, a treatment plan may still include systemic treatment even when local treatment has treated current lesions, for example to reduce the risk of the development of additional lesions.

In some cases or patients, the total patient-level plaque volume may be high, but no high-risk plaques may exist. In these patients, patient- and lesion-level risk scores may fail to identify those that can benefit from local treatment by PCI. As such, in some embodiments, for such patients, the systems, devices, and methods described herein can be configured to recommend that the patient be managed with systemic, medical treatment alone.

In some cases or patients, the total patient-level plaque volume may be high, and high-risk local plaques may also exist. In these patients, patient- and lesion-level risk scores may identify those that can benefit from local treatment by PCI and lesions that do not qualify for PCI but may benefit from systemic treatment. As such, in some embodiments, the systems, devices, and methods described herein can be configured to recommend that both local PCI and systemic medical treatment may benefit the patient.

In some embodiments, the systems, devices, and methods described herein can utilize image-based plaque and/or atherosclerosis analysis to determine a patient-specific need for systemic treatment (for example, through medication, dietary changes, exercise, etc.), local treatment (for example, PCI or CABG), both, or neither.

In some embodiments, the risk stratification approaches described herein can be used to generate a risk stratification for various systemic treatments, local treatments, or both. For example, in some embodiments, the risk stratification approaches herein can be used to determine prognoses for various interventions for a specific patient, which can aid an interventionist in determining an appropriate treatment plan.

Coronary Artery Tree Reconstruction

Also disclosed herein are systems, methods, and devices for reconstructing coronary artery trees. Accurate construction of coronary artery trees can be significant. For example, accurately determining the structure of a patient's coronary artery tree can be significant for diagnosing coronary disease, evaluating the progression of coronary disease, determining treatment plans for coronary disease, and so forth.

The coronary artery tree can refer to a network of blood vessels that supply the heart muscle with oxygen and nutrients. The coronary artery tree can include, for example, the left coronary artery (LCA), right coronary artery (RCA), and the left circumflex artery (LCx). The coronary arteries can branch out into smaller vessels and capillaries and can form an intricate network.

Disruption of bloodflow in the coronary arteries can lead to coronary artery disease (CAD) or coronary heart disease (CHD). Coronary arteries can become narrowed or blocked by the buildup of fatty deposits, cholesterol, plaque, or a combination thereof.

Various techniques exist to image the coronary arteries, including, for example, coronary computed tomography angiography (CCTA), coronary angiography, and magnetic resonance angiography (MRA). While such imaging techniques can be helpful in constructing a coronary artery tree, there are many challenges associated with constructing coronary artery trees. Vessels can be small and can have complex anatomy with various twists and turns. The heart can undergo constant motion due to its pumping action. Pumping of the heart can introduce blur and other artifacts into images. In some cases, an echocardiogram (ECG) can be used to trigger image capture in order to ensure that image capture occurs during a particular phase of a heartbeat (e.g., during contraction (systole), during relaxation (diastole), or in between phases). In some embodiments, images can be captured at specific points in the heartbeat, such as at maximum contraction or maximum relaxation.

Vessels can be located in close proximity to other tissue and structures, such as heart chambers, valves, and surrounding tissue. It can be difficult to distinguish vessels from neighboring structures. In some cases, contrast can be used to improve visibility, but achieving sufficient contrast can be challenging, and can be especially difficult in the presence of calcified plaques. Capturing images can involve patients being still for a significant period of time (e.g., up to about half an hour). During capture, a patient can move, breathe, or otherwise shift position, resulting in blur and/or other image artifacts.

Problems with images (e.g., blur, noise, poor contrast, or other issues) can make vessel extraction difficult or impossible, which can result in image rejection. When images are rejected, a patient can have to return for additional imaging, which can result in patient frustration, cause delays, have significant costs, and/or occupy potentially limited resources as hospitals or other medical facilities may have only a limited amount of equipment capable of collecting images. In some cases, computational analysis of images of a patient may simply not be performed if images of sufficient quality are not available, in which case physicians may make decisions without such information, potentially leading to worse patient outcomes.

Images collected during a coronary artery imaging procedure can, in some cases, be divided into multiple series which can, for example, correspond with different cardiac phases, such as contraction or relaxation. Some vessels can be adequately imaged in a first series (e.g., corresponding to a first cardiac phase), while different vessels can be adequately imaged in a second, different series, a third, different series, a fourth, different series, and so forth. While adequate imaging information may exist for each vessel, when the image information is split across different series, it can be challenging to identify which series should be used for which vessel.

Even if vessels can be identified in different series and quality images can be extracted, extractions of individual vessels or groups of vessels can be of limited utility as they fail to provide a complete picture of the coronary artery tree. Conventional approaches may not be able to combine images from different series to produce a complete coronary artery tree or may produce an anatomically inaccurate coronary artery tree.

It can also be significant to co-register different series to produce an accurate coronary artery tree, which can be difficult as vessels tend to move as the heart beats, the patient moves, and so forth. In some implementations, a common reference point can be used to register the multiple series.

In some implementations, a machine learning model or a plurality of machine learning models can be trained to extract vessels from CCTA images or other coronary images. The extracted vessels can then undergo further processing for use in reconstructing a coronary artery tree. As described herein, images can be divided into a plurality of series. In some implementations, vessels can be extracted from each series of the plurality of series.

After extracting the vessels, it can be significant to identify which series provides the highest quality images of each vessel. For example, the left anterior descending (LAD) artery and the circumflex branch of the left coronary artery can be imaged with higher quality in a first series (e.g., a series corresponding to the diastolic phase) while other vessels, such as the left LCA can be imaged at higher quality in another phase (e.g., the systolic phase).

In some implementations, each vessel can be labeled. In some implementations, the labels can correspond to particular anatomical features, though this is not necessary. For example, in some embodiments, vessels can be labeled as LAD, LCA, and so forth. In some implementations, vessels can be assigned a numerical, alphabetical, or other label (e.g., vessel 1, vessel 2, etc.). Labeling vessels can be significant as it enables comparing a particular vessel or group of vessels across multiple image series.

Choosing a best series for each vessel can be challenging and can involve considerations such as motion blur, contrast, image noise, and so forth. For example in some embodiments, a best series for each vessel can be selected based at least in part to minimize motion blur, maximize contrast, minimize image noise, and/or the like. In some implementations, a machine learning model or a plurality of machine learning models can be used to select the best series for each vessel. In some embodiments, a first step in selecting a series for each vessel can involve straightening each vessel. Straightened vessel images can then be input into a machine learning model that is trained to identify the best series from a plurality of series. In some implementations, the vessels may not be straightened prior to being input into the machine learning model, and the machine learning model can be trained to identify the best series from a plurality of series without straightening the vessels.

In some implementations, the aorta can be segmented from images of one or more of the image series. In some implementations, extracting the aorta can be relatively easy as the aorta can be large in comparison to vessels of the coronary artery tree. In some cases, contrast can be used during an image collection procedure, which can result in the aorta being readily visible in images.

While the above operations can be used to extract vessels and identify the best series for each vessel, it can be significant to combine or register images of each vessel to reconstruct a complete coronary artery tree. In some implementations, the aorta can be used as a reference for combining images to generate a reconstructed complete (or nearly complete) coronary artery tree. In some embodiments, ostia can be used as reference(s) for reconstructing the coronary artery tree. In some embodiments, images from different series can be stitched together based at least in part on one or more reference points or landmarks, for example one or more bifurcation landmarks. The reconstructed coronary artery tree can be used for various purposes.

In some implementations, the systems and methods described herein can be used in the visualization of plaques. For example, plaques can be overlaid onto a complete or almost complete coronary artery tree. In some implementations, the systems and methods herein can enable more accurate fractional flow reserve CT (FFR-CT) analysis, which can be used to determine or estimate the impact of coronary artery stenoses. In some implementations, the systems and methods herein can be used to assess or visualize myocardial mass at risk (MMAR), which can require an accurate and complete or nearly complete coronary artery tree.

Variable Plaque Categorization Thresholds

Plaque calcification can be an important indicator of disease and can help to identify, for example, the risk of adverse cardiac events. Correct identification of calcified plaques can have important implications for medical interventions, for example to determine whether or not a stent should be placed in a vessel, whether procedures such as atherectomy or angioplasty should be performed, a type of stent to be used, and so forth. In some embodiments, plaque categorization can inform whether systemic interventions, local interventions, or both should be pursued.

While plaque categorization can be significant, it can be difficult to determine whether plaque is calcified or not, the degree of calcification, and so forth. Invasive procedures such as optical coherence tomography (OCT) can provide relatively accurate and/or reproducible determination of the presence and size of calcified plaques, but such invasive procedures can be time-consuming, present a risk for procedural complications, and so forth. Additionally, OCT typically offers limited tissue penetration, and thus may not fully characterize a plaque.

Coronary computed tomography angiography (CCTA) imaging offers high spatial and temporal resolution, and it can provide detailed information about plaque morphology. However, CCTA has limited ability to differentiate between calcified and non-calcified plaques, and the apparent size of a plaque can vary depending upon image acquisition parameters, attenuation within a patient's body, attenuation within nearby areas (e.g., within the lumen), and so forth. In some implementations, a plaque can be characterized (e.g., classified as calcified or non-calcified) based on its Hounsfield intensity, but the appropriate characterization can vary depending on attenuation, acquisition parameters, and so forth. The peak kilovoltage (kVp) can have a significant impact on the apparent size of a calcified plaque.

Thus, while CCTA can provide valuable insights, its utility in classifying plaques as calcified or non-calcified, or in determining a degree of calcification, can be limited. Described herein are approaches that can be used to mitigate or overcome these limitations, enabling CCTA imaging to be used to gain valuable insights into plaques, which can reduce or eliminate the need for invasive procedures.

In some implementations, the approaches herein can be used to normalize CCTA images so that they can provide reliable, reproducible insight into plaque calcification. In some embodiments, the approaches described herein can improve the accuracy of identification and/or classification of calcified plaques.

In CCTA, the boundary between non-calcified and calcified plaque (or between plaques with different levels of calcification) can be defined in terms of radiodensity. In some implementations, boundaries can be defined in terms of Hounsfield units (HU). In some embodiments, the appropriate boundaries can be defined in relation to peak kilovoltage and lumen HU values. For example, it has been observed that lumen contrast can influence the apparent size of plaques. Thus, a boundary between plaque types (e.g., between calcified plaque and non-calcified plaque) can depend on the observed lumen contrast. Changes in peak kilovoltage (kVp) can have a significant impact on the x-ray spectrum produced by an x-ray source, which can in turn have a significant influence on a resulting CCTA image.

Many factors can influence the appropriate threshold for identifying calcified plaques and distinguishing them from non-calcified plaques. For example, the specific x-ray source, x-ray detector, collimators, geometry (e.g., source to detector distance), and so forth can each influence a final CCTA image. In some embodiments, the boundary between calcified and non-calcified plaque can be determined for specific x-ray detectors, sources, geometry configurations, and so forth. However, such an approach may be undesirable as it can be difficult to predict all possible equipment or combinations of equipment components that may be used for collecting CCTA images. Thus, in some implementations, it can be desirable to reduce or eliminate the need to account for specific types of equipment, configurations, and so forth. As described herein, in some embodiments, a plaque calcification threshold can be defined in terms of kVp and lumen contrast. Using these two parameters, a system can be configured to determine an appropriate boundary between calcified and non-calcified plaque, thereby providing a relationship between kVp, lumen contrast, and plaque calcification threshold that is independent of specific equipment properties and parameters.

Lumen contrast can be an attractive parameter for use in determining a plaque categorization threshold because, for example, the lumen is an empty void and thus is expected to present fairly consistently when imaged.

In some embodiments, OCT images can be used as a baseline or ground truth for the true extent of a calcified plaque. It will be appreciated, however, that OCT may not provide a fully accurate measure of a calcified plaque. However, OCT can be accepted as a suitable reference for determining a threshold between calcified plaque and non-calcified plaque.

While OCT can be used to differentiate between calcified and non-calcified plaque, it can struggle to differentiate between low attenuation plaque (LAP) and fibrofatty plaque. In some embodiments, near-infrared spectroscopy (NIRS) can be used to differentiate between LAP and fibrofatty plaque. The approaches described herein can be readily adapted to other imaging modalities, which can enable the use of CCTA for a wide range of applications.

The approaches herein can be used to more accurately and/or reproducibly determine the presence, size, and so forth of calcified plaques using non-invasive CCTA imaging. In some embodiments, the approaches herein can be used to characterize a volume, area, and/or length of a calcified plaque. For example, in some embodiments, the approaches herein can be used to facilitate more accurate and/or reproducible determination of a thickness of a plaque (e.g., a thickness extending from a vessel wall into the lumen).

While much of the discussion herein relates to differentiating between calcified and non-calcified plaques (e.g., to identification of a plaque calcification threshold for differentiating between calcified and non-calcified plaques), the approaches herein are not so limited. In some embodiments, the approaches herein can be used to differentiate between low-density calcified plaque, medium-density calcified plaque, high-density calcified plaque, and so forth.

In general, it may be expected that thresholds for distinguishing between types of plaque (e.g., non-calcified, low-density calcified, medium-density calcified, high-density calcified) move the same directionally as kVp and lumen density varies. However, they may not move by the same amount. In some embodiments, relationships can be determined using the techniques described herein that can allow for multiple threshold values to be determined. Thus, for example, when a threshold is adjusted to distinguish between calcified and non-calcified plaque, other thresholds (e.g., between low-density and medium-density calcified plaques, or between medium-density and high-density calcified plaques), a known relation, which can be, for example, linear, polynomial, exponential, logarithmic, etc., can be used to shift the other thresholds by an appropriate amount.

In some embodiments, thresholds can be set at a global level (e.g., for an entire image). In some embodiments, thresholds can be set at a local level, which can help to account for localized effects such as, for example, blooming that may be present around a lumen. Typically, blooming affects an area around a lumen in a concentric or approximately concentric fashion, and bloom can fall off with a known or determinable gradient.

In some embodiments, a system can be configured with one or more default thresholds for differentiating between types of plaque. In some embodiments, the system can include a graphical interface, configuration file, etc., that can enable a user (e.g., a physician) to customize one or more thresholds, thereby enabling the physician to more readily utilize their experience and expertise when analyzing plaques.

In some cases, when determining thresholds, there can be one or more outlier thresholds (e.g., thresholds that are significantly higher or lower than thresholds indicated by other images with similar imaging conditions). In some embodiments, one or more outlier thresholds can be discarded when determining plaque categorizations thresholds.

Thin Cap Fibroatheroma Identification

In the present disclosure, approaches for detecting thin cap fibroatheroma (TCFA) using coronary computed tomography angiography (CCTA) imaging are disclosed. The approaches described herein can enable non-invasive detection of TCFA.

Fibroatheroma is a type of plaque that can present a significant risk of adverse health events. Some fibroatheromas are more likely to result in adverse health events than others. Fibroatheromas can be characterized by the presence of a fibrous cap that forms a boundary between the core of the fibroatheroma and a lumen. The thickness of the cap can be an indicator of the likelihood that a fibroatheroma will erupt. When a fibroatheroma ruptures, the thrombogenic core of the fibroatheroma can be released into the lumen, resulting in thrombosis. Studies have shown that ruptured plaques can be characterized by the presence of a thin fibrous cap that is less than 65 micrometers or about 65 micrometers thick. Fibroatheromas with such thin caps can be categorized as thin cap fibroatheromas (TCFAs).

Accurately imaging thin caps can be difficult. For example, intravascular ultrasound virtual histology (IVUS-VH) can have an axial resolution of about 200 micrometers, limiting its ability to identify TCFA. CCTA also lacks the ability to reliably image thin caps.

According to some embodiments described herein, TCFA can be identified without necessarily imaging the cap itself and/or without having a high accuracy measure of the thickness of the cap. For example, the presence of low attenuation non-calcified plaque near a lumen can indicate the presence of TCFA. However, CCTA can struggle to identify low-attenuation plaques. Invasive procedures such as optical coherence tomography may be more reliable but can be complex and pose some patient risk.

Determining plaque density, calcification, or both can be accomplished using CCTA imaging according to some embodiments described herein. The apparent size, density, and so forth of a plaque can be influenced by the contrast of the nearby lumen, the peak kilovoltage of an x-ray source used to collect the CCTA image, and so forth. According to some implementations, CCTA images can be normalized based on lumen contrast (which can be measured in Hounsfield units (HU)) and kVp, for example as described above with respect to variable plaque categorization. In some embodiments, low attenuation plaque (LAP) can be differentiated from other non-calcified and/or calcified plaque.

According to some embodiments, TCFA can be determined by the presence of LAP at or near a boundary of a plaque, for example at the interface between the plaque and the lumen.

Plaque types can be classified in CCTA images based on their attenuation, which can be measured in HU. Typically, lower HU values can indicate less calcification and/or other differences in plaques, such as lower material density. While CCTA alone can provide relative information about plaques (e.g., more calcification or less calcification relative to other plaques), it can be important to obtain a more absolute measure of plaque properties (e.g., calcification) so that plaques can be accurately classified and treatment approaches can be determined based on reliable, accurate information.

In some cases, OCT imaging may not be able to resolve a thin cap but may be able to be used to differentiate between LAP and other non-calcified plaque. In some embodiments, a threshold between LAP and other non-calcified plaque for CCTA images can be determined based on, for example, analysis of OCT images.

In some embodiments, a set of CCTA images and a set of OCT images can be co-registered, and a threshold cutoff (e.g., in HU) between LAP and other non-calcified plaque can be adjusted for the CCTA images so that the CCTA images reflect the extent of LAP as determined using OCT. In some embodiments, only cross-sectional images may be used. Cross-sectional images can show the proximity of LAP to the boundary between the plaque and the lumen. In some embodiments, three-dimensional images can be used, which can provide additional and/or different insight into the extent of LAP.

To identify TCFA, in some embodiments, it may not be necessary to know the precise size and shape of the LAP. For example, it can be sufficient to determine that the LAP extends to or close to the surface of the plaque. In some implementations, a set of OCT images can be divided into groups, with one group comprising images where TCFA is present and the other comprising images where TCFA is not present. In some implementations, thresholds for differentiating between LAP and other non-calcified plaque can be adjusted so that CCTA images can reliably be categorized as showing TCFA or not showing TCFA, e.g., as determined by comparison with OCT images. In some embodiments, a system can be configured to allow a user to adjust one or more thresholds, thereby enabling the user (e.g., a physician) to more readily utilize their expertise and/or experience when looking for the presence of TCFA.

In some embodiments, an apparent thickness of a cap can be determined from CCTA images. As described herein, such thickness may not be accurate, but it may not be necessary to have an accurate thickness measurement or accurate information about the size and shape of LAP in order to detect TCFA. Rather, it can be sufficient that there is a clear separation between apparent cap thicknesses in CCTA images where TCFA is present and CCTA images where TCFA is not present, and/or it can be sufficient that the location of LAP (e.g., relative to the boundary between the plaque and the lumen) is determined accurately enough to differentiate between TCFA and non-TCFA.

In some embodiments, a system can determine a probability of TCFA. In some embodiments, the system can determine that TCFA is likely if the probability is above a threshold value. In some embodiments, the system can determine that TCFA is not likely if the probability is below a threshold value. In some embodiments, a system can be configured to output an indication that TCFA is likely, an indication that TCFA is not likely, and/or the probability of TCFA.

Stent Selection and Surgical Planning

Also disclosed herein are systems, methods, and devices for analyzing lesions. Such analysis can be used in stent selection, surgical planning (e.g., manual surgical planning and/or robotic surgical planning), and so forth.

Coronary artery disease is a significant problem. Stenting procedures can be beneficial to reduce the risk of adverse events; however, there are significant challenges associated with stenting procedures. For example, it can be important to select a stent based on the length of plaque, the normal diameter of the vessel being stented, the density of the plaque, the location of the plaque, and so forth. There are many types of stents available, which can have different mechanical properties. It can be important to select a stent with mechanical properties that are adapted to the specific needs of a patient. For example, it can be important to consider how the stent behaves when deflected, under tension, under compression, under flexion, and so forth.

It can be important to avoid using a stent that is too short to fully cover a plaque. Uncovered plaque can lead to adverse outcomes such as in-stent restenosis, in which a vessel begins to narrow again at or near the site of the stent, and/or other complications.

In conventional approaches, many decisions are typically made during an intervention rather than being pre-planned. For example, during a procedure, an interventionist may use techniques such as intravascular ultrasound (IVUS) and/or fluoroscopic imaging to aid in determining placement of a stent. A lack of information prior to a procedure can lead to sub-optimal treatment, such as the use of a stent that is not long enough, too long, too narrow, too wide, etc., wasted time during the procedure, post-surgical complications (which can include major adverse cardiac events), and so forth.

Deficiencies in pre-planning can mean that interventionists do not know ahead of time what they will need to carry out a procedure, which can lead to wasted medical supplies, wasted preparation time, sub-optimal patient outcomes, and so forth. For example, surgical support staff may select several stents ahead of time, and then during a procedure, the interventionist can select the best available stent. The interventionist may not have the length and/or diameter stent that they need, and thus may pick a closest available stent. If the stent is too short, the patient runs a risk of restenosis. Longer stent lengths can also have complications. For example, the risk of thrombosis has been linked to stent length, as has the risk of myocardial infarction.

The approaches described herein can provide for more accurate, thorough, and/or complete planning of stenting procedures. Using the approaches described herein, the length, diameter, position, and so forth of a stent can be determined prior to carrying out a procedure. In some embodiments, stent positioning can be determined ahead of time. As described herein, positioning determinations can be made without the use of an absolute reference frame. Rather, positioning of a stent can be determined based on the relative distance from one or more reference points. A reference point can include, for example, the ostium, left main trifurcation, left main bifurcation, or any other reference point.

In some embodiments, the approaches described herein can be used in surgical training, for example to train new or otherwise inexperienced surgeons to perform stenting procedures. In some embodiments, the approaches described herein can be used in robotic surgery. For example, the approaches described herein can be used to generate instructions that direct a surgical robot to make one or more movements to a desired location for placement of a stent.

The approaches herein can offer many advantages, such as reduced medical supply waste, reduced procedure time, and/or improved patient outcomes. For example, the approaches herein can reduce the risk of restenosis, thrombosis, myocardial infarction, and/or other adverse outcomes. Costs can be reduced as a treatment facility can plan ahead of time and order only stents on planned procedures where the stents that will be needed are known ahead of time.

Conventionally, techniques such as fractional flow reserve (FFR) are used to analyze stenoses. In FFR, pressure differences across a stenosis are measured to determine a likelihood that the stenosis significantly reduces oxygen delivery. FFR is an invasive procedure in which a catheter is inserted into a patient and routed to the patient's heart. Various other techniques can be used additionally or alternatively to obtain information for diagnosing and treating a patient. For example, invasive angiography can be used to determine stenosis, ultrasound can be used to determine length and volume of a plaque, near field infrared spectroscopy can be used to identify lipid-rich plaque, optical coherence tomography can be used to determine a minimum luminal diameter, and so forth.

According to some implementations, the approaches herein can be used to non-invasively obtain information similar to what is conventionally obtained only via invasive procedures. The techniques herein can be used to identify ischemia, identify lesions (e.g., lesions in the left main artery, lesions in the left anterior descending artery, etc.), and so forth. In some implementations, the approaches described herein can be used to differentiate between plaque types (e.g., between calcified and non-calcified plaque), determine a required stent length, and/or determine whether multiple stents will be needed. In some implementations, data from multiple data collection modalities can be included in a same user interface, thereby facilitating easier interpretation of the data.

In some implementations, CCTA images can be analyzed to make surgical decisions. However, information is often scattered in multiple places, making planning difficult. In some implementations, multiple kinds of information on a single screen can be helpful for a user to determine stenting procedure, stent length, stent design, whether or not to intervene, etc. In some implementations, a system can be configured to identify likely ischemia. In some cases, an interventionist may decide to perform a stenting procedure only on plaques that are likely to be ischemic. By using the approaches described herein, surgical procedures can be planned ahead of time and the right size, material, shape, etc., for stents can be selected, which can provide clinical and economic advantages. For example, patients may experience fewer complications, and facilities may stock only needed stents. In some cases, an interventionist may want to calcify soft plaques. Using the techniques herein, the interventionist can identify soft plaques and choose, for example, a drug-eluting stent that includes a drug that will help to calcify the plaque.

According to some implementations, a user interface can be provided that illustrates vessels and labels the vessels to indicate stenosis, likely ischemia, chronic total occlusion, and so forth. In some implementations, a user interface can be provided that shows an elongated view of a vessel and that identifies lesions (e.g., plaques) in the vessel. In some implementations, a user can click on or otherwise select a lesion to view information about the lesion, such as maximum diameter stenosis, plaque length, minimum luminal diameter, normal lumen diameter, plaque volume, calcification, and so forth.

As described herein, in some implementations, a system can be configured to generate a surgical plan. For example, in some implementations, a user can select one or more plaques for treatment and can generate a treatment plan. The treatment plan can include, for example, the location of the plaque (e.g., distance from a reference point such as the ostium), stent length, and/or stent diameter.

In some implementations, a system can be configured to generate a robotic surgery plan. The robotic surgery plan can include, for example, instructions for movements of a surgical robot. For example, a surgical robot can be instructed to follow a path along a vessel until the robot reaches a particular distance from a reference point (e.g., the ostium).

Example Embodiments

Figure 7:
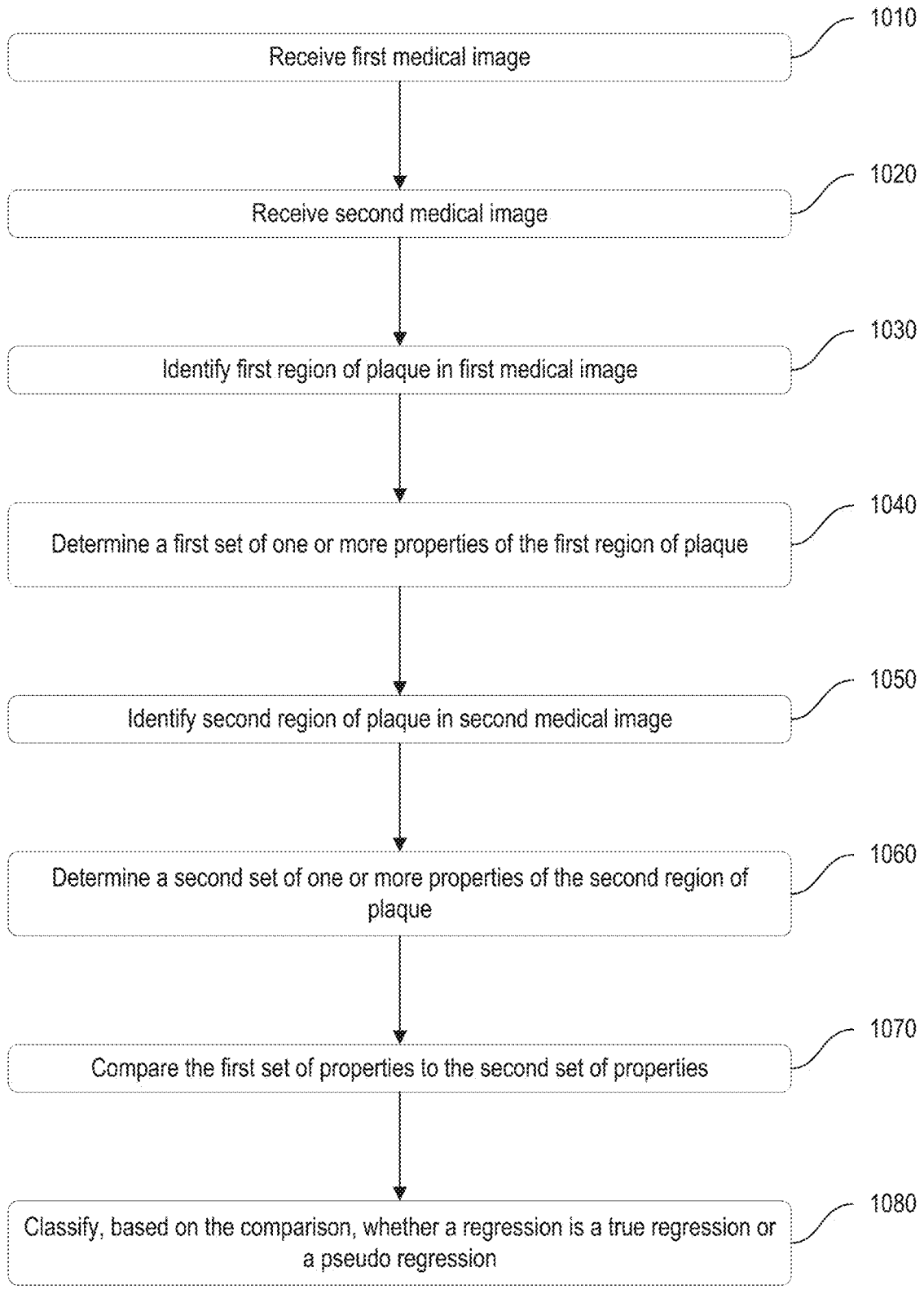
FIG. 7 is a block diagram that illustrates an example process for differentiating between true and pseudo plaque regression according to some embodiments.

FIG. 7 is a block diagram that illustrates an example process for differentiating between true and pseudo plaque regression according to some embodiments. The process shown in FIG. 7 can be carried out on a computer system. In some embodiments, the operations shown in FIG. 7 can be performed in an order different from that shown, additional operations may be present, and/or one or more illustrated operations may be omitted or combined with other operations.

At operation 1010, the computer system can receive a first medical image. At operation 1020, the computer system can receive a second medical image. The first medical image and second medical image can include a region of plaque. At operation 1030, the computer system can identify a first region of plaque in the first medical image. At operation 1040, the computer system can determine a first set of one or more properties of the first region of plaque. The one or more properties can include, for example and without limitation, total plaque volume, low density non-calcified plaque volume, non-calcified plaque volume, calcified plaque volume, material density, radiodensity, Hounsfield unit density of one or more types of plaque, or any combination thereof. At operation 1050, the computer system can identify a second region of plaque in the second medical image. The second region of plaque can be the same region of plaque as the first region of plaque. The second medical image can be, for example, an image of the same region of plaque at a later point in time. At operation 1060, the computer system can determine a second set of one or more properties of the second region of plaque. At operation 1070, the computer system can compare at least one property of the first set of properties with a corresponding at least one property of the second set of properties to determine a change in at least one property between the first medical image and the second medical image. At operation 1080, the computer system can classify, based on the at least one property comparison, classify whether an observed plaque regression is a true regression or a pseudo regression.

Figure 8:
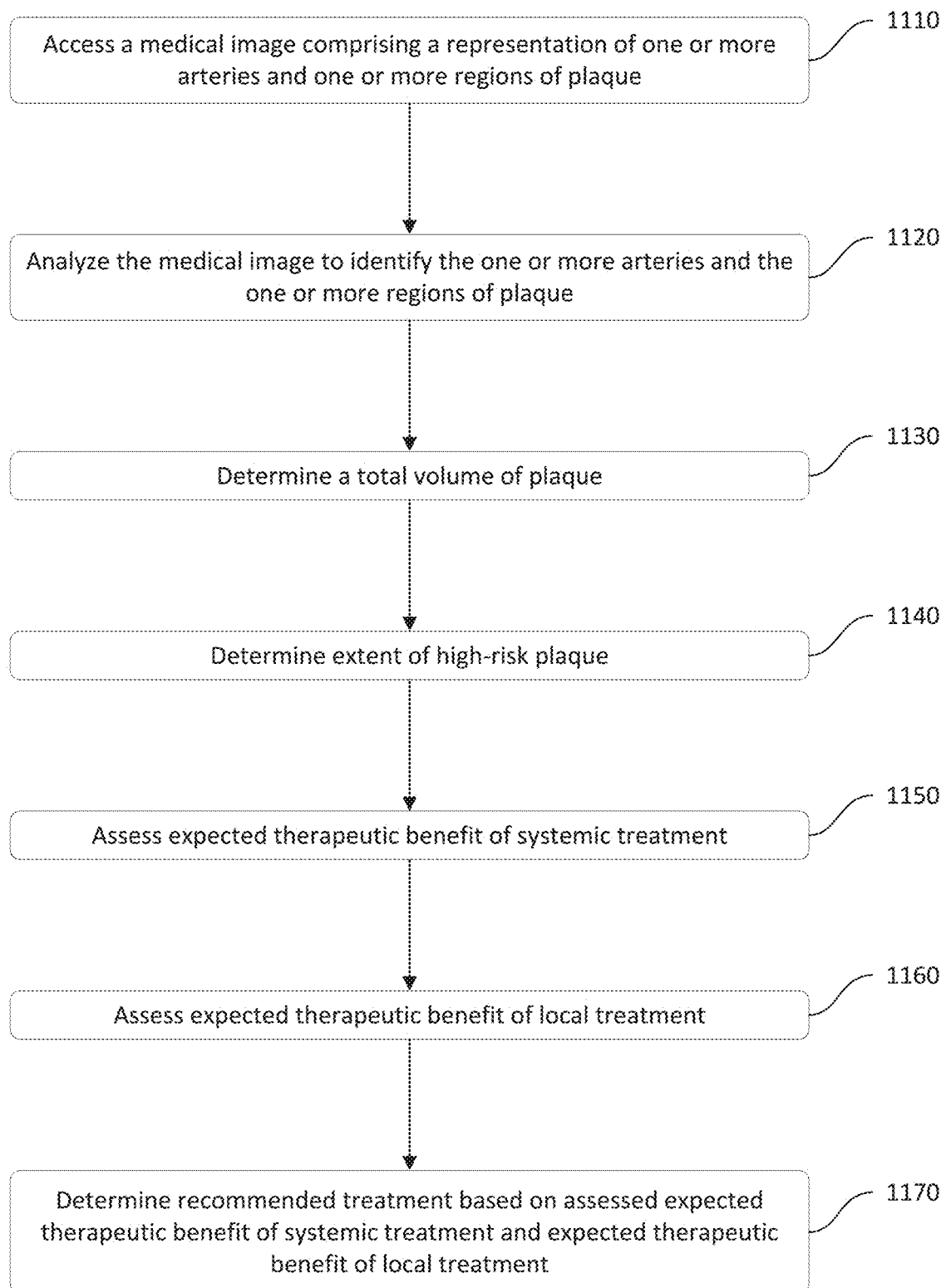
FIG. 8 is a block diagram that illustrates an example process for determining a recommended treatment according to some implementations.

FIG. 8 is a block diagram that illustrates an example process for determining a recommended treatment according to some implementations. The process shown in FIG. 8 can be carried out using a computer system. In some embodiments, the operations shown in FIG. 8 can be carried out in an order different from that shown, additional operations may be present, and/or one or more illustrated operations may be omitted or combined with other operations.

At operation 1110, the system can access a medical image comprising a representation of one or more arteries and one or more regions of plaque (e.g., one or more regions of atherosclerotic plaque). At operation 1120, the computer system can analyze the medical image to identify the one or more arteries and the one or more regions of plaque. In some embodiments, identifying the one or more arteries can include determining anatomical labels for the one or more arteries, although this is not necessary and may not occur in some other embodiments. At operation 1130, the computer system can determine a total plaque volume. At operation 1140, the computer system can determine an extent of high-risk plaque. At operation 1150, the system can assess an expected therapeutic effect of systemic treatment, for example based on the total volume of plaque, the total volume of high risk plaque, or both. In some embodiments, the expected therapeutic effect can consider other factors, such as a patient's age, weight, activity level, prior interventions, and so forth. At operation 1160, the system can assess the expected therapeutic benefit of local treatment, for example based on the total volume of plaque, the extent of high-risk plaque, or both. In some embodiments, the computer system can consider other factors, such as the patient's age, weight, activity level, prior interventions, and so forth. At operation 1170, the computer system can, based on the expected therapeutic benefit of systemic treatment and the expected therapeutic benefit of local treatment, determine a recommended treatment or a plurality of recommended treatments. In some embodiments, the computer system can cause the recommended treatment or the plurality of recommended treatments to be presented to a physician or other user. In some embodiments, systemic treatment may be preferred as there can be a lower likelihood of complications with medications, changes to diet, changes to exercise, and so forth than with local treatments, such as stenting. In some embodiments, local treatment may be favored when systemic treatment is less likely to be effective and/or when there may be difficulties with systemic treatments, such as drug interactions, limitations on the patient's physical activity, the patient's demonstrated failure to adhere to diet or exercise plans, and so forth.

Figure 9:
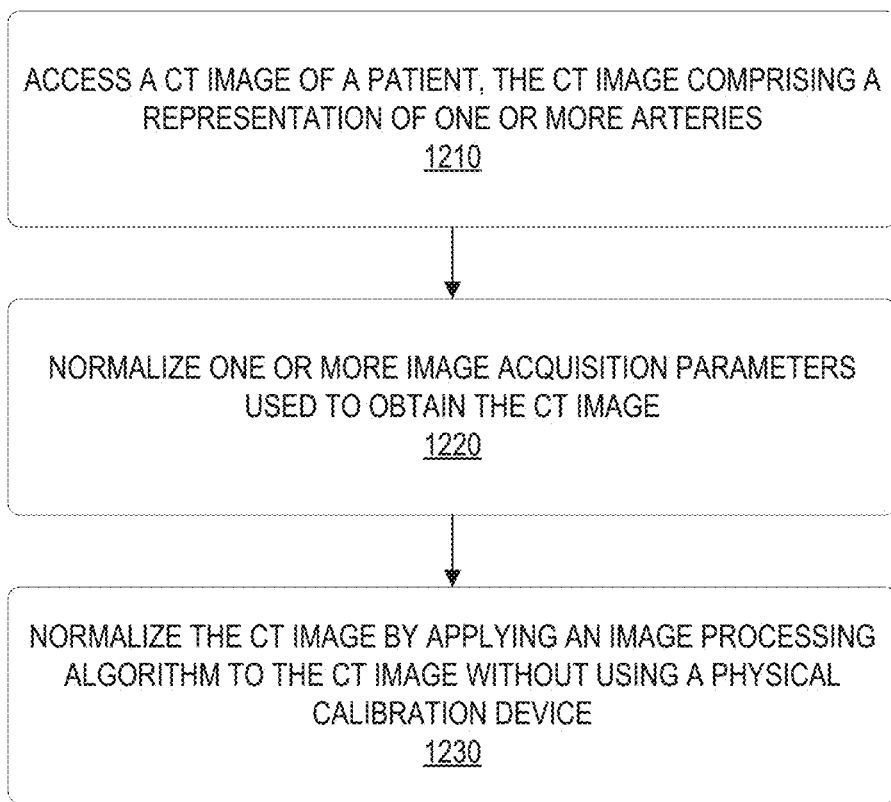
FIG. 9 is a flowchart that illustrates an example image normalization process according to some embodiments.

FIG. 9 is a flowchart that illustrates an example image normalization process according to some embodiments. The example process of FIG. 9 can be performed on a computer system.

At operation 1210, the system can access a CT image of a patient. In some embodiments, the CT image can include a representation of one or more arteries. In some embodiments, the one or more arteries can include one or more regions including atherosclerotic plaque. At operation 1220, the system can access one or more image acquisition parameters used to obtain the CT image. In some embodiments, the image acquisition parameters can include, for example and without limitation, method of helical CT, type of CT detector, type of CT based on number of photon energy spectra, x-ray generator current (mA), peak kilovoltage (kVp), image noise, image signal, signal to noise ratio, contrast opacification, and/or contrast to noise ratio. At operation 1230, the system can normalize the CT image by applying an image processing algorithm to the CT image. In some embodiments, normalization may not make use of a physical calibration device. In some embodiments, the image processing algorithm can be derived by analyzing a plurality of test CT images obtained from a same subject and one or more image acquisition parameters used to obtain the plurality of test CT images. In some embodiments, the test CT images can include one or more regions including atherosclerotic plaque. In some images, the image processing algorithm can be derived by analyzing simulated CT images.

In some embodiments, the normalized CT image can be analyzed to generate one or more plaque parameters and/or one or more vascular parameters. The one or more plaque parameters can include, for example, total plaque volume, non-calcified plaque volume, and/or calcified plaque volume. In some embodiments, the one or more vascular parameters can include one or more lumen measurements. In some embodiments, the one or more plaque parameters and/or the one or more vascular parameters generating from the normalized CT image can be compared to one or more corresponding plaque parameters and/or vascular parameters generated from another (e.g., a prior) CT image of the patient.

Figure 10:
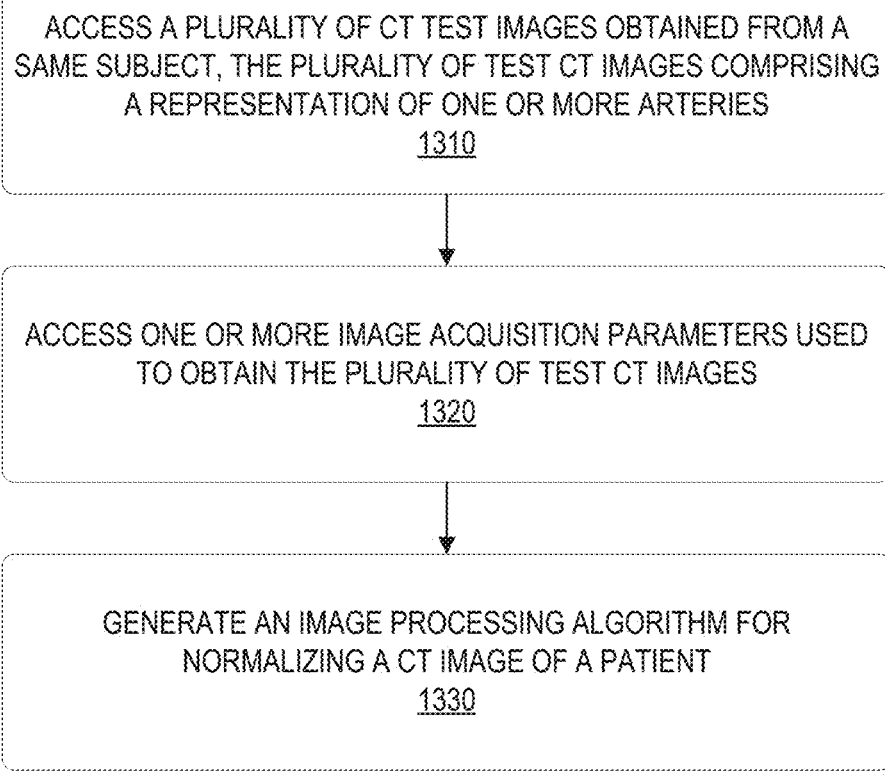
FIG. 10 is a flowchart that illustrates an example process for generating an image processing algorithm according to some embodiments.

FIG. 10 is a flowchart that illustrates an example process for generating an image processing algorithm (e.g., the image processing algorithm discussed above with reference to FIG. 9) according to some embodiments. The example process of FIG. 8 can be performed on a computer system.

At operation 1310, the system can access a plurality of test CT images obtained from a same subject. In some embodiments, the plurality of test CT images can include a representation of one or more arteries of the subject. In some embodiments, the one or more arteries can include one or more regions including atherosclerotic plaque. At operation 1320, the system can access one or more image acquisition parameters used to capture the plurality of test CT images. At operation 1330, the system can generate an image processing algorithm for normalizing a CT image of a patient based at least in part on the plurality of test CT images. In some embodiments, physical calibration device images may not be used to generate the image processing algorithm.

In some embodiments, the image processing algorithm can be generated using a regression (e.g., a linear regression or nonlinear regression). In some embodiments, the image processing algorithm can be generated by training a machine learning model. For example, test images and image acquisition parameters of the test images (which may be real images or simulated images) can be used as inputs for training a machine learning model (e.g., the test images and image acquisition parameters can be used to generate feature vectors for a machine learning model). In some embodiments, the generated image processing algorithm can receive two sets of image acquisition parameters associated with a first image and a second image, and the generated image processing algorithm can use the received image acquisition parameters to determine normalization parameters to apply to one of the first image or the second image to normalize the first image and second image with respect to one another.

Figure 11:
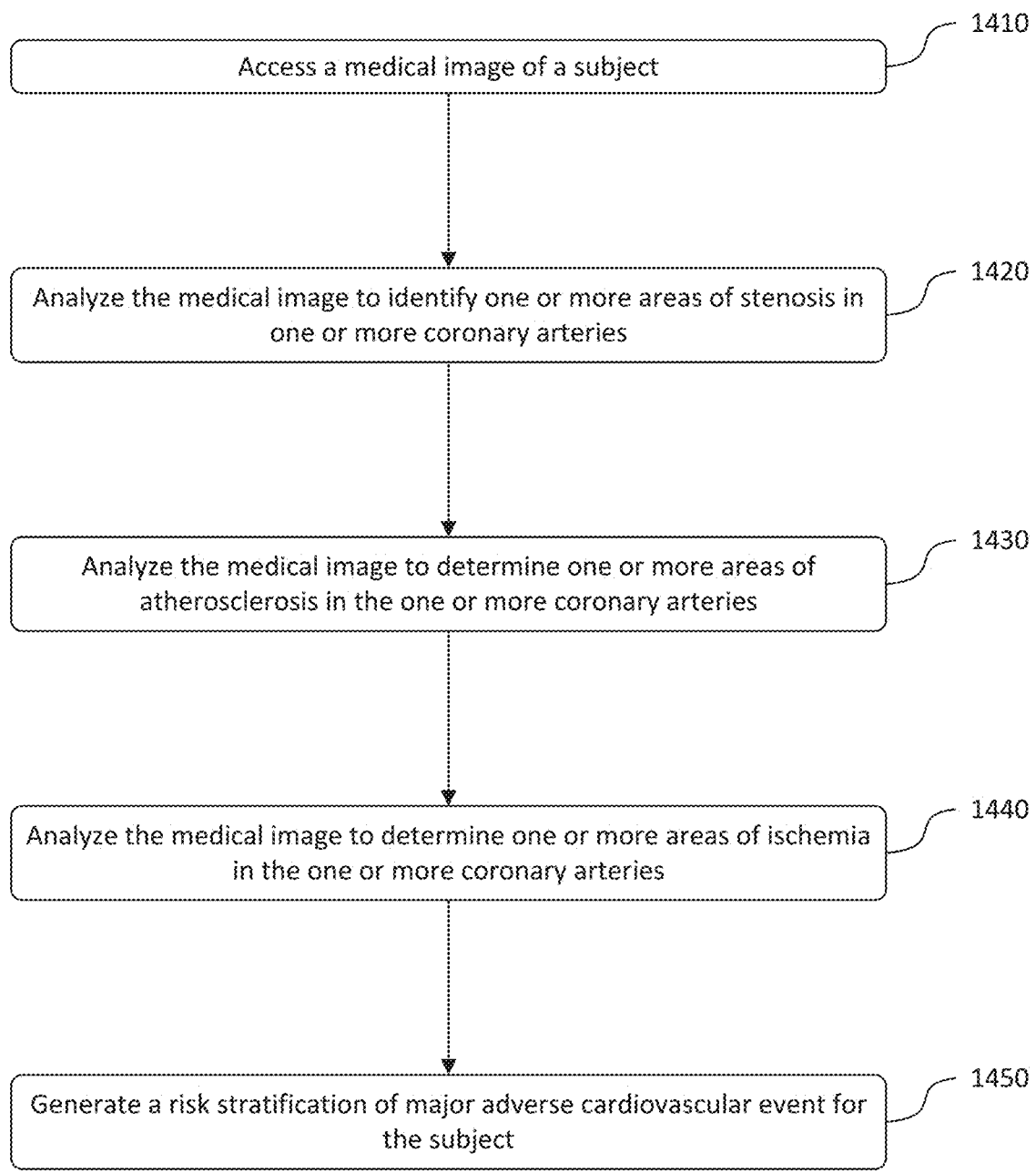
FIG. 11 is a block diagram that illustrates an example process for determining risk stratification according to some embodiments.

FIG. 11 is a block diagram that illustrates an example process for determining risk stratification according to some embodiments. The process shown in FIG. 11 can be carried out on a computer system. At operation 1410, the computer system can access a medical image of a subject. At operation 1420, the computer system can analyze the medical image to identify one or more areas of stenosis in one or more coronary arteries. At operation 1430, the computer system can analyze the medical image to determine one or more areas of atherosclerosis in the one or more coronary arteries. At operation 1440, the computer system can analyze the medical image to determine one or more areas of ischemia in the one or more coronary arteries. At operation 1450, the system can generate a risk stratification of MACE for the subject. In some embodiments, the system can cause the generated risk stratification to be provided to a user, such as a physician.

Figure 12:
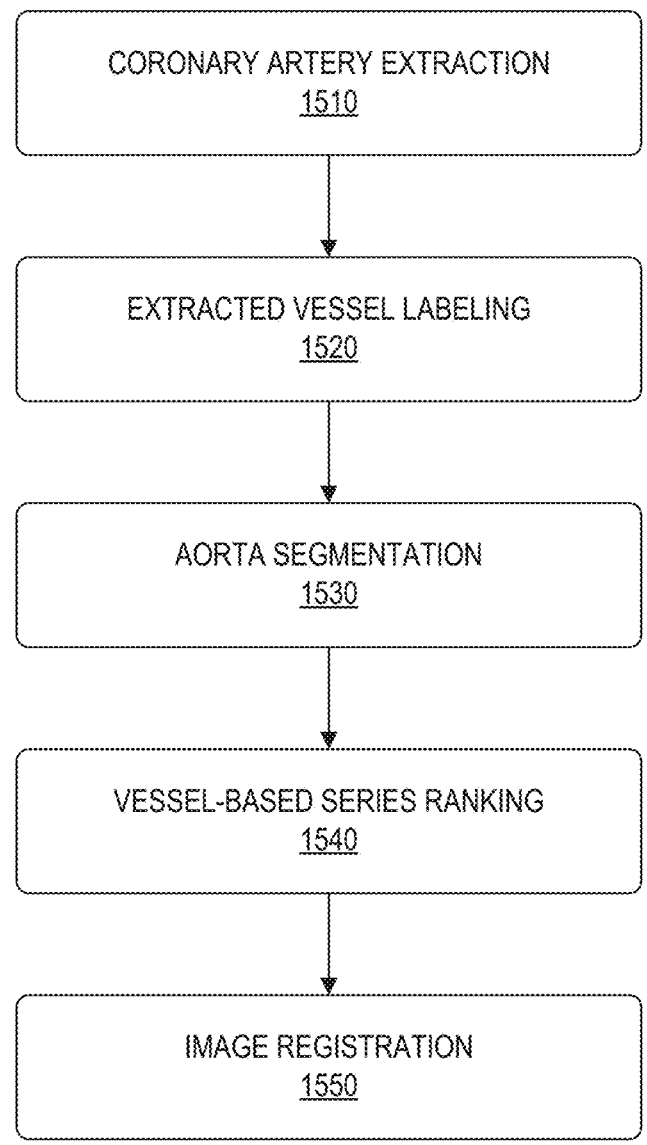
FIG. 12 is a flowchart that shows an example process for reconstructing a coronary artery tree according to some implementations.

FIG. 12 is a flowchart that shows an example process for reconstructing a coronary artery tree according to some implementations. The process illustrated in FIG. 12 can be carried out on a computer system using a plurality of images. The plurality of images can be, for example, coronary computed tomography angiography (CCTA), coronary angiography, and/or magnetic resonance angiography (MRA) images.

At operation 1510, the method includes extracting coronary artery vessels from a plurality of images corresponding to a plurality of series. The method can include extracting the coronary artery vessels for each series. Each series can correspond to a phase of a heartbeat. For example, images can be captured in response to an ECG trigger so that each image series can correspond to a particular phase of a heartbeat. In implementations, one or more machine learning models can be used to extract the coronary artery vessels. In some embodiments, the one or more machine learning models can include a convolutional neural network.

At operation 1520, the method includes labeling the extracted vessels in each series. In some implementations, the labeling can correspond to anatomical features. In some implementations, the labeling may not correspond to anatomical features. The labels can be the same for the same vessel across the plurality of series.

At operation 1530, the method includes segmenting the aorta. For example, the aorta of a patient can be visible in each series of the plurality of series. The aorta or parts thereof can be used as a reference when reconstructing the complete coronary artery tree.

At operation 1540, the method includes ranking each series of the plurality of each series for each labeled vessel. Ranking the series can be carried out using a machine learning model or multiple machine learning models. The machine learning model(s) can include a convolutional neural network, deep neural network, and so forth. A highest ranked image series can be an image most suitable for coronary artery tree reconstruction. A highest ranked image series can have, for example, higher contrast, less noise, and/or less blue than other series.

In some implementations, prior to ranking the series, the method can include straightening each vessel. For example, an image of a vessel can undergo geometric transformations to make the vessel appear straight.

At operation 1550, the method includes registering the selected series for each vessel to generate a reconstructed coronary artery tree. For example, the aorta or one or more portions thereof can be used as reference point(s) for reconstructing the coronary artery tree. For example, the left and right main coronary arteries just above the coronary ostia, and the coronary ostia can be used in determining the relative positioning of the left and right main coronary arteries. In some embodiments, an overlap ratio can be used to determine a quality of the reconstructed coronary artery tree.

Figure 13:
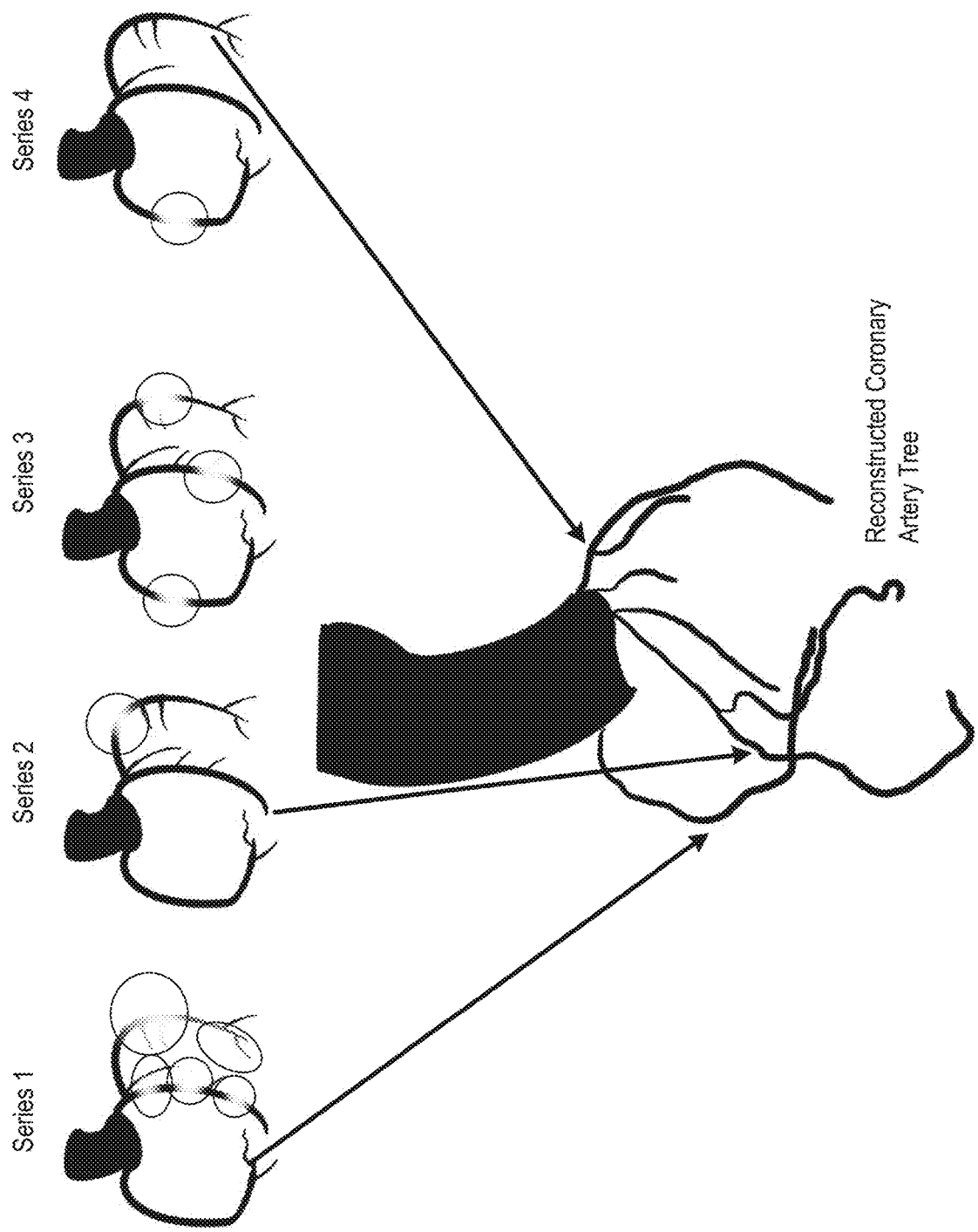
FIG. 13 shows an illustration of a reconstructed coronary artery tree and the series used to generate the reconstructed coronary artery tree.

FIG. 13 shows an illustration of a reconstructed coronary artery tree and the series used to generate the reconstructed coronary artery tree. In FIG. 13, there are four series, and the vessels are divided into three vessels. In some implementations, there can be more or fewer series and/or more or fewer vessels. In FIG. 13, regions of poor image quality are indicated by the ovals. In FIG. 13, Series 1 is used for a first vessel, Series 2 is used for a second vessel, and Series 4 is used for a third vessel. Series 3 exhibits regions of poor quality on each vessel and thus is not used for any vessels in the reconstructed coronary artery tree because there are other series with higher quality images. While in FIG. 8, there is a one-to-one mapping between series and vessels, it will be appreciated that a single series can be the best series for more than one vessel. For example, in the illustrated example, Series 1 and Series 2 are drawn with similar quality for the first vessel, and Series 2 could be the best series for both the first vessel and the second vessel.

Figure 14:
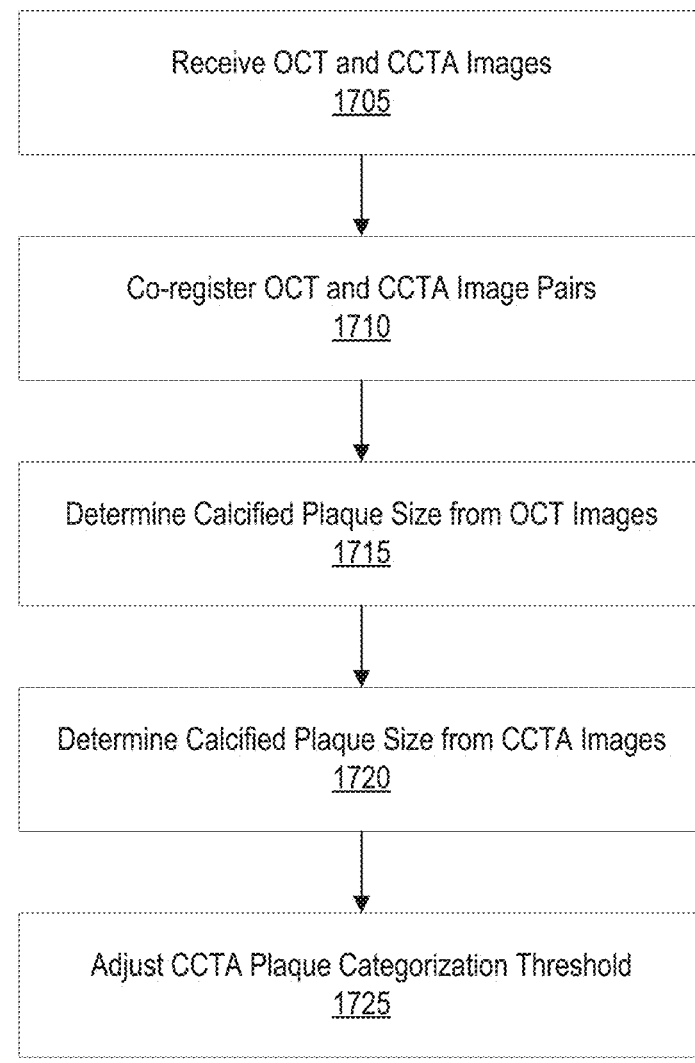
FIG. 14 is a flowchart that illustrates an example process for adjusting a plaque categorization threshold for coronary computed tomography angiography images according to some implementations.

FIG. 14 is a flowchart that illustrates an example process for adjusting a plaque categorization threshold for CCTA images according to some implementations. The process can be performed by a computer system. In the following discussion, it is assumed that a threshold is set in HU. However, it will be appreciated that any suitable scale describing attenuation in CCTA images can be used.

At operation 1705, the system can receive a set of OCT images and a set of CCTA images. Each OCT image can correspond to a CCTA image to form an image pair. At operation 1710, the system can co-register each OCT and CCTA image pair. At operation 1715, the system can determine calcified plaque sizes from the OCT images. In some implementations, the calcified plaque sizes may have been previously determined, in which case operation 1715 can be skipped or modified to include receiving the previously determined calcified plaque sizes. At operation 1720, the system can determine calcified plaque sizes from the received CCTA images. At operation 1725, the system can adjust CCTA plaque categorization thresholds so that the calcified plaque sizes determined from CCTA images more closely matches the calcified plaque sizes determined from OCT images.

While not illustrated in FIG. 14, it will be appreciated that, as described herein, the threshold can vary depending upon the kVp used to capture images and the lumen contrast. Thus, in some implementations, the process depicted in FIG. 14 can be carried out for a plurality of kVp and lumen contrast combinations to produce a plurality of plaque categorization thresholds corresponding to the different kVp and lumen contrast combinations. Typically, kVp values are limited to a few values, such as 80 kV, 100 kV, or 120 kV. However, lumen contrast can vary from image to image. Thus, in some embodiments, lumen contrast can be binned into groups with similar contrast. For example, a bin can include a range of about 20 HU, about 25 HU, about 50 HU, about 100 HU, or any value between these values, or more or less.

In some implementations, lumen contrast values may not be binned. For example, in some implementations, the determined thresholds can be used to calculate an equation that outputs the plaque categorization threshold and receives the lumen contrast and kVp as inputs. In some implementations, the equation can be a linear equation, polynomial equation, logarithmic equation, exponential equation, and so forth.

Figure 15:
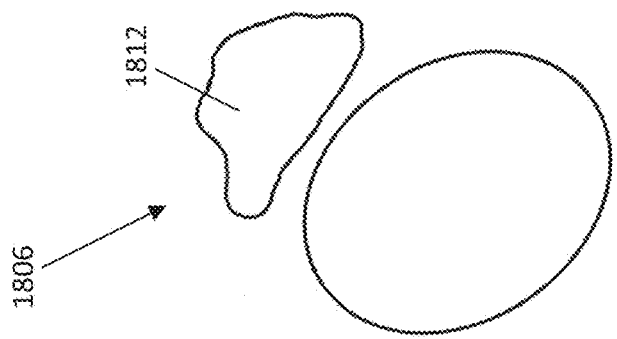
FIG. 15 is a drawing that schematically illustrates the impact of a plaque calcification threshold according to some implementations.
Figure 15:
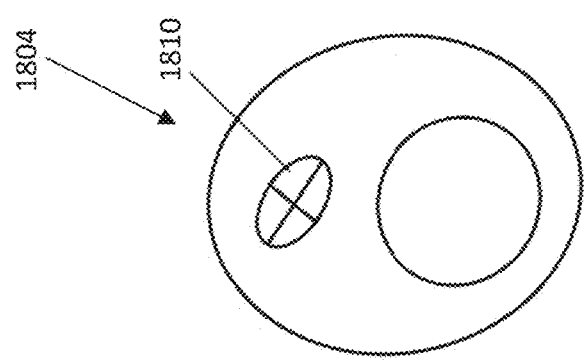
Figure 15:
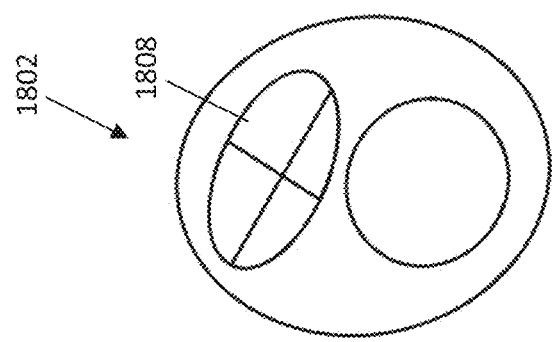

FIG. 15 is a drawing that schematically illustrates the impact of a plaque calcification threshold according to some implementations. In FIG. 15, a first CCTA image 1802 with a first plaque calcification threshold shows a first calcified plaque region 1808, a second CCTA image 1804 can be a same image as the first CCTA image 1802, but with a second, different plaque calcification threshold. The second CCTA image 1804 can show a second calcified plaque region 1810. The first plaque calcification threshold can be lower than the second plaque calcification threshold, causing the first calcified plaque region 1808 to appear larger than the second calcified plaque region 1810. An OCT image 1806 can be taken as a "ground truth" image. As discussed herein, while an OCT image may not represent the true size of a calcified plaque region, in some cases it can be considered as a good approximation. In the OCT image 1806, a calcified plaque region 1812 is illustrated. As shown in FIG. 15, the size of the first calcified plaque region 1808 is closer to the size of the calcified plaque region 1812. This can be because the first plaque calcification threshold more accurately represents the threshold between calcified and non-calcified plaque than the second threshold, in which plaque that was identified as calcified in the OCT image 1806 is identified as non-calcified in the second CCTA image 1804.

Figures 16, 17:
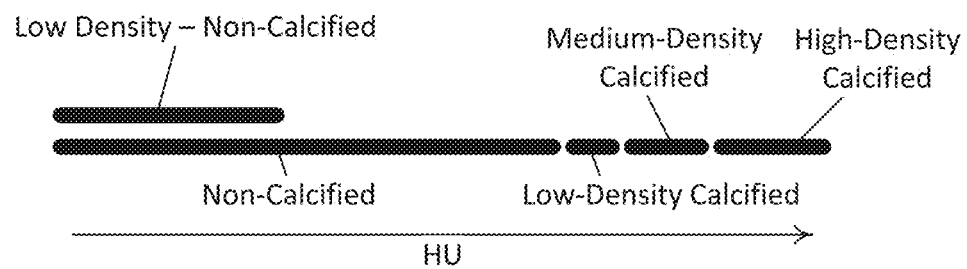
FIG. 16 is a drawing that schematically illustrates various possible thresholds for plaques according to some implementations.
FIG. 17 is a table that illustrates an example of plaque calcification thresholds in relation to lumen contrast and kilovoltage.

FIG. 16 is a drawing that schematically illustrates various possible thresholds for plaques according to some implementations. As shown in FIG. 16, typically, more calcified plaques will show higher contrast (e.g., higher HU values). In some implementations, plaques can be divided into two categories: calcified and non-calcified. However, it will be appreciated that there may not be a clear cutoff between calcified and non-calcified, and the level of calcification can fall on a spectrum. In some implementations, calcified plaques can be subdivided into, for example, low-density calcified plaques, medium-density calcified plaques, and high-density calcified plaques. In some cases, such information can be helpful for determining treatment plans. In other cases, such information may have limited clinical relevance. In some implementations, non-calcified plaques can include low density, non-calcified plaques, also known as low attenuation plaques.

FIG. 17 is a table that illustrates an example of plaque calcification thresholds in relation to lumen contrast and kVp. As shown in FIG. 17, a plaque calcification threshold can generally increase with decreasing kVp and can generally increase with increasing lumen contrast. It will be appreciated, however, that the specific thresholds shown in FIG. 17 are merely for illustration, and actual thresholds can vary. In some implementations, a table such as that shown in FIG. 17 can be used as a lookup table for determining a plaque calcification threshold for a given kVp and lumen contrast. In some implementations, the information presented in such a table can be used to create a multivariable equation that describes the relationship between kVp, lumen contrast, and plaque calcification threshold. In some embodiments, interpolation can be used to determine thresholds for intermediate values of lumen contrast and/or kVp.

Figure 18:
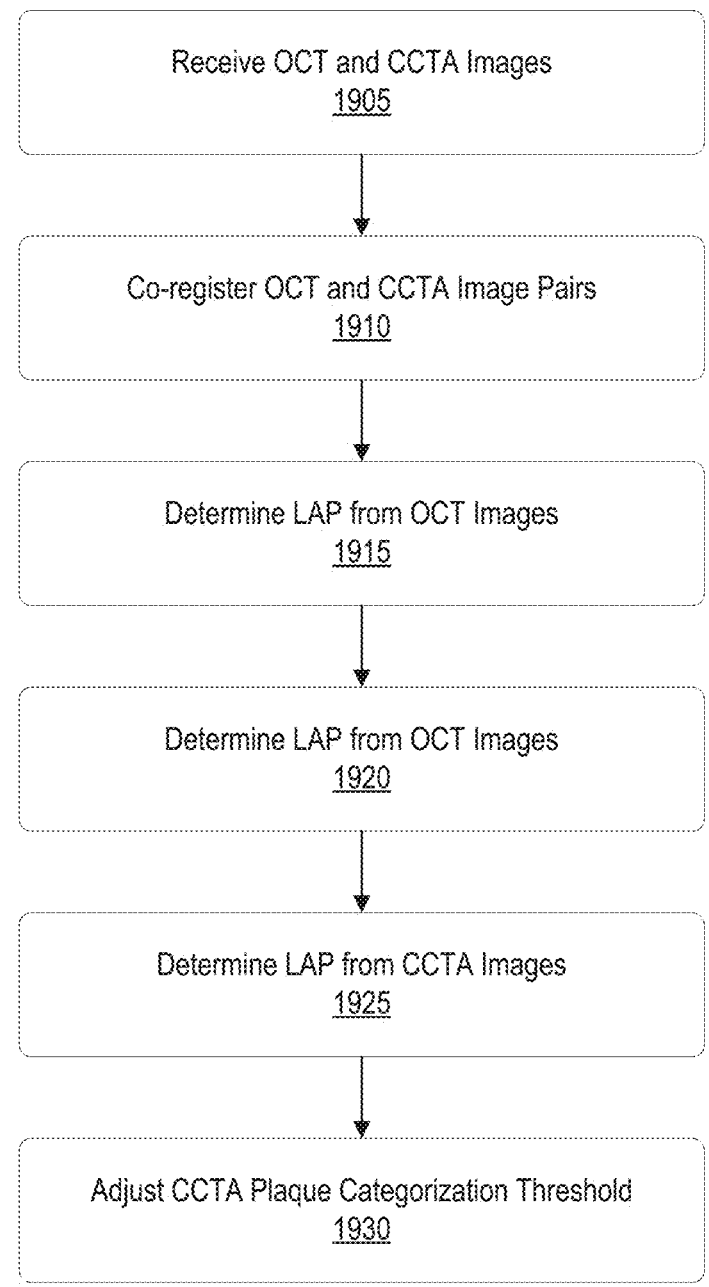
FIG. 18 is a flowchart that shows an example process for determining a threshold Hounsfield unit value for differentiating between low attenuation plaque and other non-calcified plaque according to some implementations.

FIG. 18 is a flowchart that shows an example process for determining a threshold HU value for differentiating between LAP and other non-calcified plaque according to some implementations. The process shown in FIG. 18 can be performed by a computer system.

At operation 1905, the system can receive a set of CCTA images and a set of OCT images. At operation 1910, the system can co-register the CCTA images and OCT images. For example, for each CCTA image, there can be a corresponding OCT image, and the CCTA image and OCT image can be co-registered. At operation 1915, the system can determine the presence of LAP in an OCT image. At operation 1920, the system can determine the presence of LAP in the OCT image. At operation 1925 the system can determine the presence of LAP in the CCTA image. At operation 1930, the system can adjust a CCTA plaque categorization threshold such that the determined presence of LAP in the CCTA image is within a threshold amount of the determined presence of LAP in the corresponding OCT image.

Figure 19:
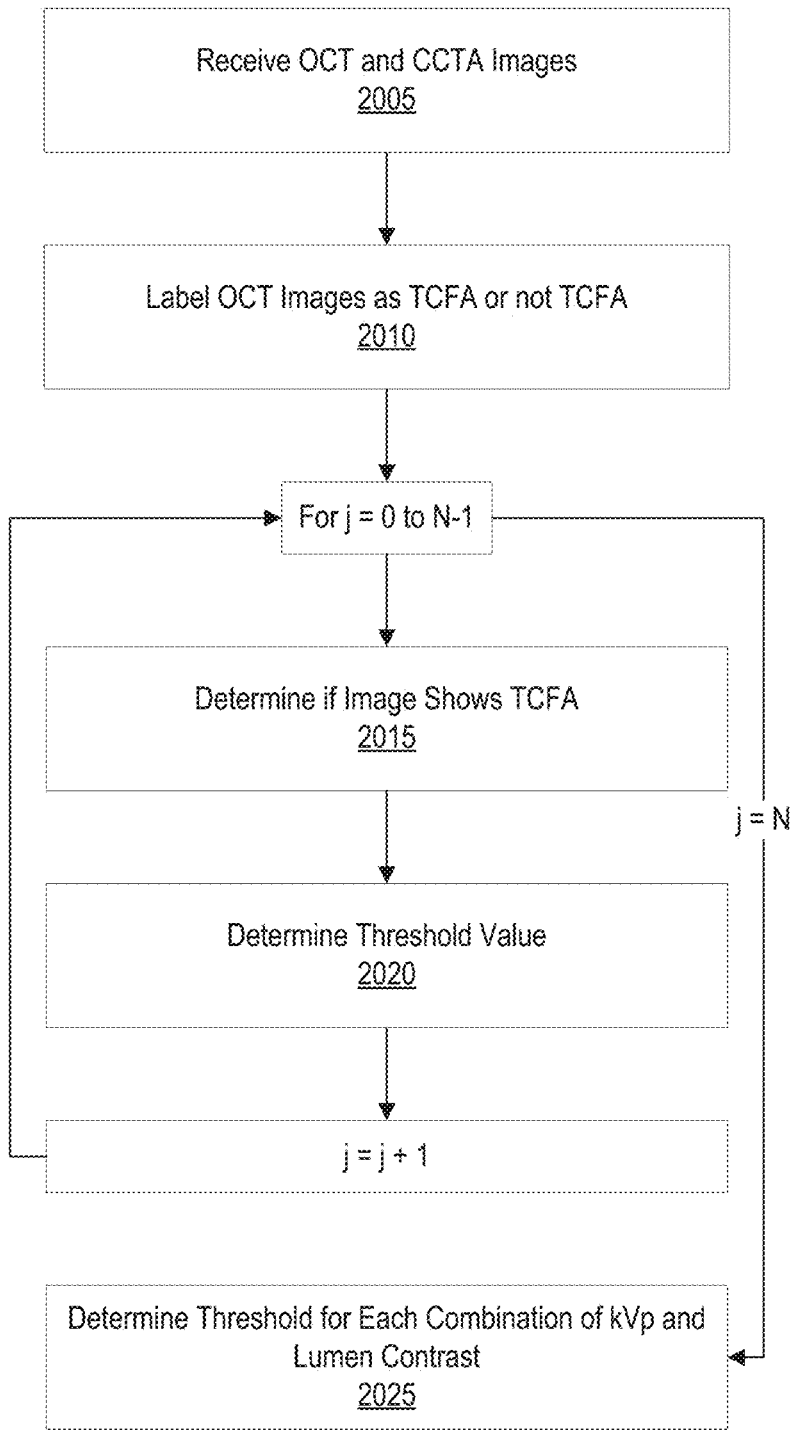
FIG. 19 is a flowchart that illustrates an example process for determining a threshold Hounsfield unit value for identifying thin cap fibroatheroma according to some implementations.

FIG. 19 is a flowchart that illustrates an example process for determining a threshold HU value for identifying TCFA according to some implementations. The process shown in FIG. 8 can be performed by a computer system.

At operation 2005, the system can receive a set of OCT images and a set of CCTA images. At operation 2010, the system can label the OCT images as TCFA or not TCFA. In some implementations, the system can analyze each OCT image to determine if it shows signs of TCFA or not. In some implementations, the OCT images can be pre-labeled as showing TCFA or not. Each OCT image can correspond to a CCTA image. For each CCTA image, the system can, at operation 2015, determine if the image shows TCFA, for example by determining whether or not LAP in the image extends to the boundary between the core of a plaque in the image and a lumen in the image. The system can compare this result to the label for the corresponding OCT image, and can, at operation 2020, determine a threshold value. For example, the system can iteratively modify the threshold value. In some implementations, the system can adjust the threshold value just until the analysis gives the incorrect result. In some implementations, the iterative adjustment can be, for example, 10 HU or about 10 HU, 20 HU or about 20 HU, 50 HU or about 50 HU, or more or less, or any value between these values. In this way, assuming a roughly equal distribution of TCFA and non-TCFA images, the system can determine a range of threshold values for identifying TCFA. In some implementations, equal or roughly equal fractions of images with and without TCFA may not be required. For example, results can be weighted such that an overall threshold value for a kVp and lumen contrast can be determined. At operation 2025, the system can determine a threshold value for each combination of kVp and Lumen contrast. In some implementations, Lumen contrast can be binned, for example in groups of 10 HU, 20 HU, 30 HU, 40 HU, 50 HU, 100 HU, or any value between these values, or more or less. Binning can ensure that each combination of kVp and lumen contrast has a sufficient number of samples to determine a reliable threshold value.

Figure 20:
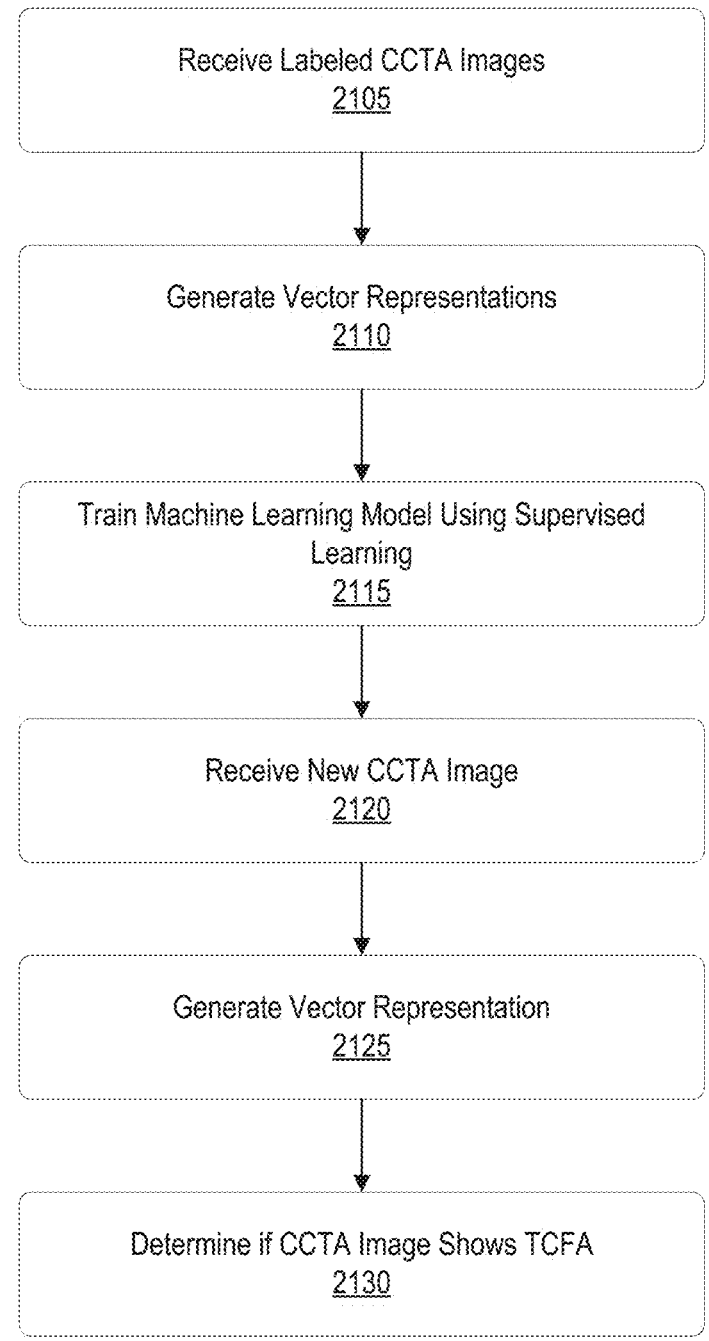
FIG. 20 is a flowchart that illustrates an example process for identifying thin cap fibroatheroma in coronary computed tomography angiography images using machine learning according to some implementations.

In some implementations, a machine learning model can be trained to identify TCFA in CCTA images. The machine learning model can be trained using supervised learning as described herein. FIG. 20 is a flowchart that illustrates an example process for identifying TCFA in CCTA images using machine learning according to some implementations. The process of FIG. 20 can be carried out by a computer system. In FIG. 20, training and deployment are illustrated as a single process. However, it will be understood that training and deployment can be implemented as separate processes that can be carried out on the same computer system or different computer systems.

At operation 2105, the system can receive a plurality of labeled CCTA images. The labels can indicate whether or not the CCTA image shows TCFA as well as the kVp used to capture the CCTA image. In some implementations, the labels can include a lumen contrast, although such information may not be included in some other implementations. At operation 2110, the system can generate vector representations of the CCTA images. In some implementations, the vector representations can include representations of one or more labels or parts of one or more labels. For example, the vector representation of an image can encode image data as well as the kVp used to capture the image. At operation 2115, the system can train a machine learning model using supervised learning. For example, a "TCFA present" label can indicate whether or not an image shows TCFA, and the model can be trained using supervised learning where "TCFA present" is the desired output.

After training, the model can be deployed. During deployment, the model can receive new CCTA images for which the presence of TCFA is unknown. The presence of TCFA can be determined by the model. At operation 2120, the system can receive a new CCTA image. At operation 2125, the system can generate a vector representation of the received CCTA image. The vector representation can include, in some implementations, a kVp value used to capture the CCTA image. At operation 2130, the system can, using the machine learning model trained at operation 2115, determine if the received CCTA image shows TCFA.

In the description of FIGS. 18, 19, and 20, it is assumed that identification of TCFA is agnostic to the equipment used to capture images. However, in some cases, that may not be the case. For example, in some implementations, the x-ray source, x-ray detector, geometry (e.g., distance from source to detector), collimator used, and so forth can impact the resulting image. In some implementations, the total radiation dose to which a patient is exposed can impact the resulting image. While in many cases, consideration of lumen contrast can be used to account for the impact of such variations in image capture, in some cases, including some or all of the information above may result in improved accuracy.

Figure 21B:
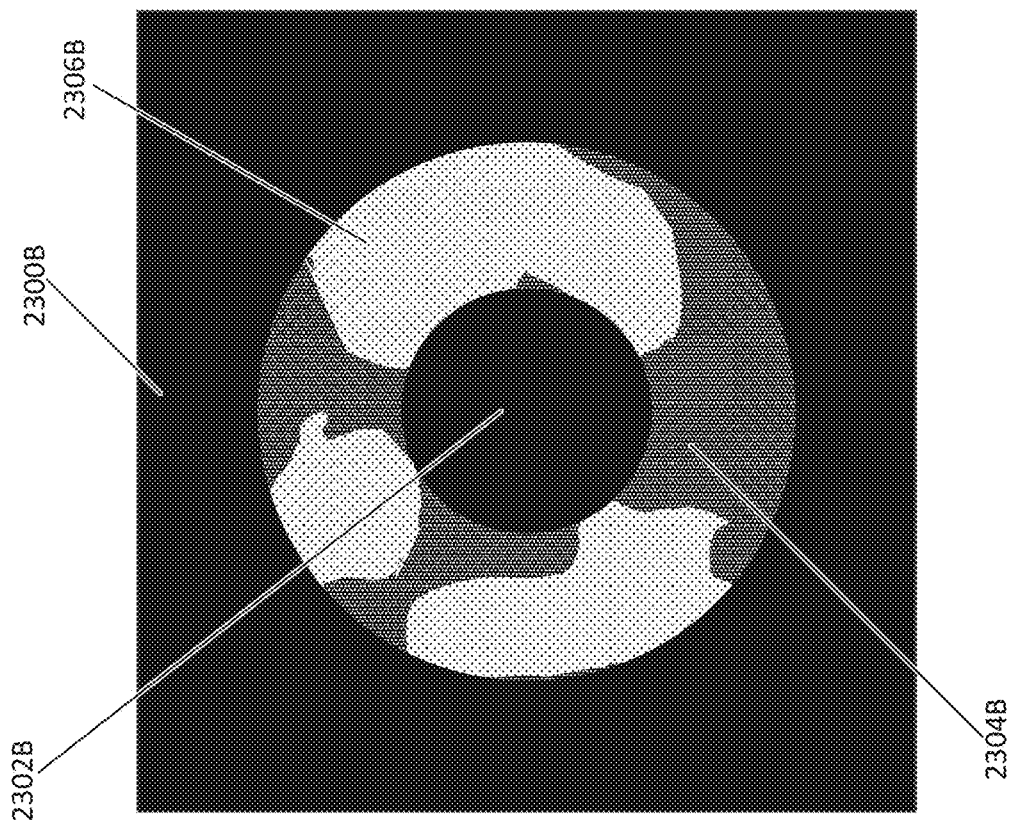
FIGS. 21A and 21B schematically illustrate examples of coronary computed tomography angiography images that do not show thin cap fibroatheroma and that do show thin cap fibroatheroma.
Figure 21A:
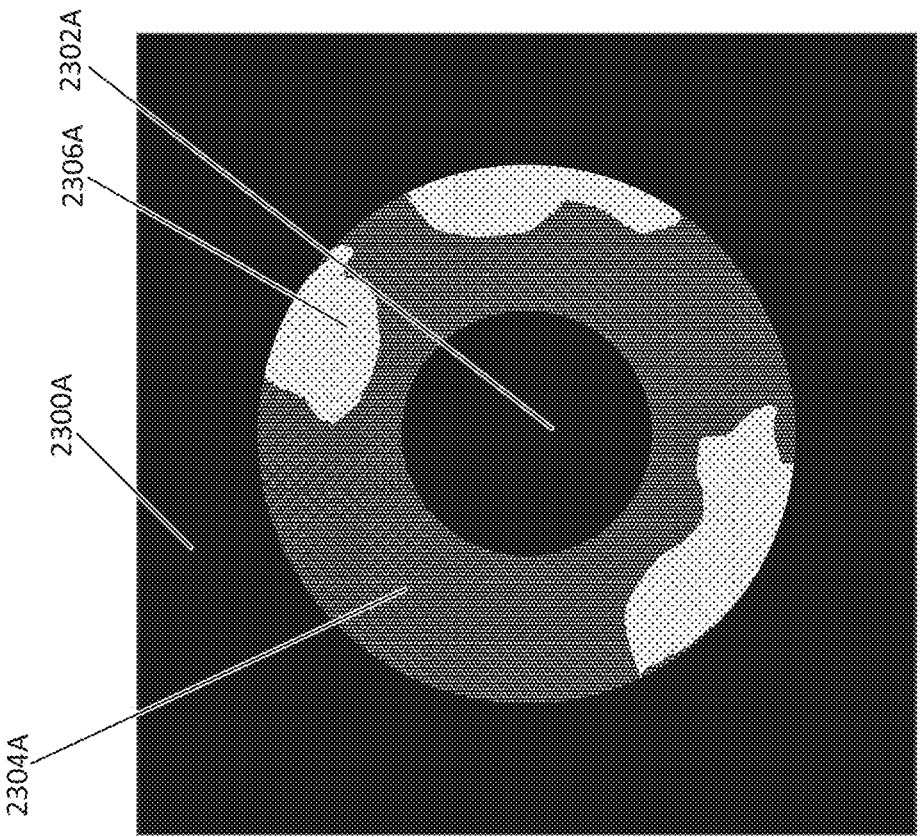

FIGS. 21A and 21B schematically illustrate examples of CCTA images that do not show TCFA (FIG. 21A) and do show TCFA (FIG. 21B). In the CCTA image 2300A, the lumen 2302A is surrounded by a plaque 2304A. In some regions, a low attenuation plaque 2306A is present. However, the low attenuation plaque 2306A does not extend to the interface between the lumen and the plaque. In some implementations, a system that implements one or more of the approaches described herein can identify the CCTA image 2300A as not showing TCFA. In the CCTA image 2300B, the plaque 2304B includes low attenuation plaque 2306B. In FIG. 21B, the low attenuation plaque 2306B extends to the boundary between the plaque and the lumen 2302B. In some implementations, a system that implements one or more of the approaches described herein can identify the CCTA image 2300B as showing the presence of TCFA.

Figure 22B:
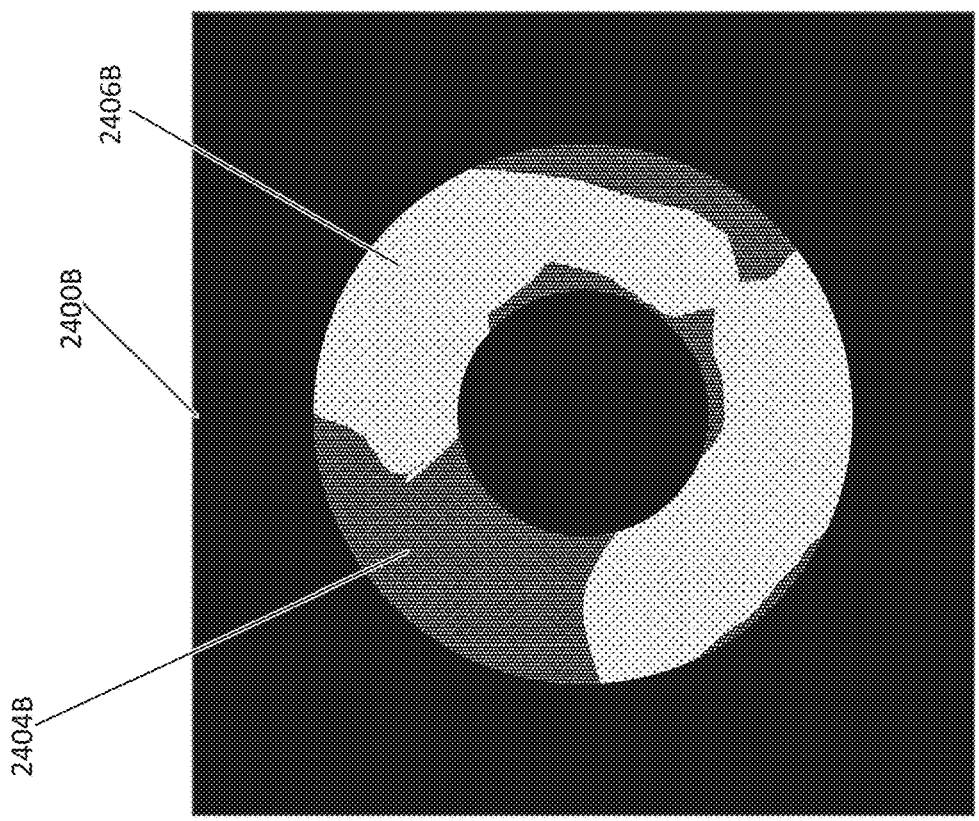
FIGS. 22A and 22B schematically illustrate an example of a coronary computed tomography angiography image with different cutoff thresholds for low attenuation plaque.
Figure 22A:
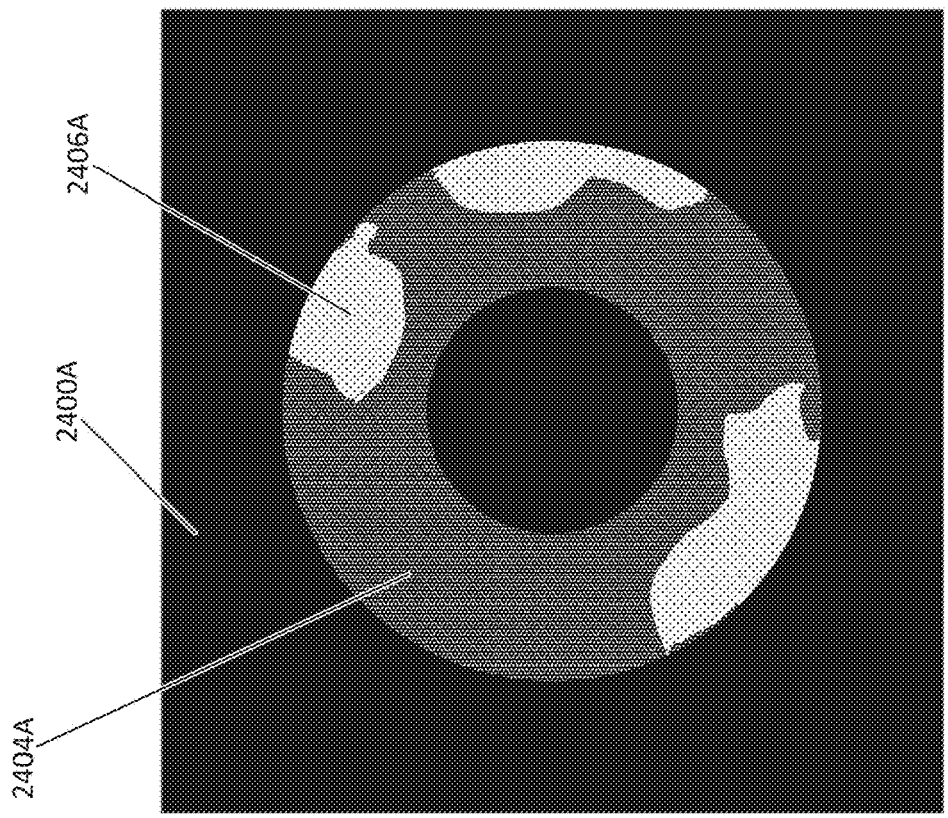

FIGS. 22A and 22B schematically illustrate an example of a CCTA image with different cutoff thresholds for LAP. In the CCTA image 2400A, a lower contrast cutoff is used to differentiate between LAP 2406A and non-LAP 2404A (which can include non-calcified and/or calcified plaque). The CCTA image 2400B schematically illustrates the CCTA image 2400A, but with a different threshold for separating the LAP 2406B from other plaque 2404B. As shown in FIGS. 22A and 22B, the determination of whether or not TCFA is present (e.g., whether or not low attention plaque reaches the boundary between the plaque and a lumen) can change depending upon the selected threshold.

Figure 23:
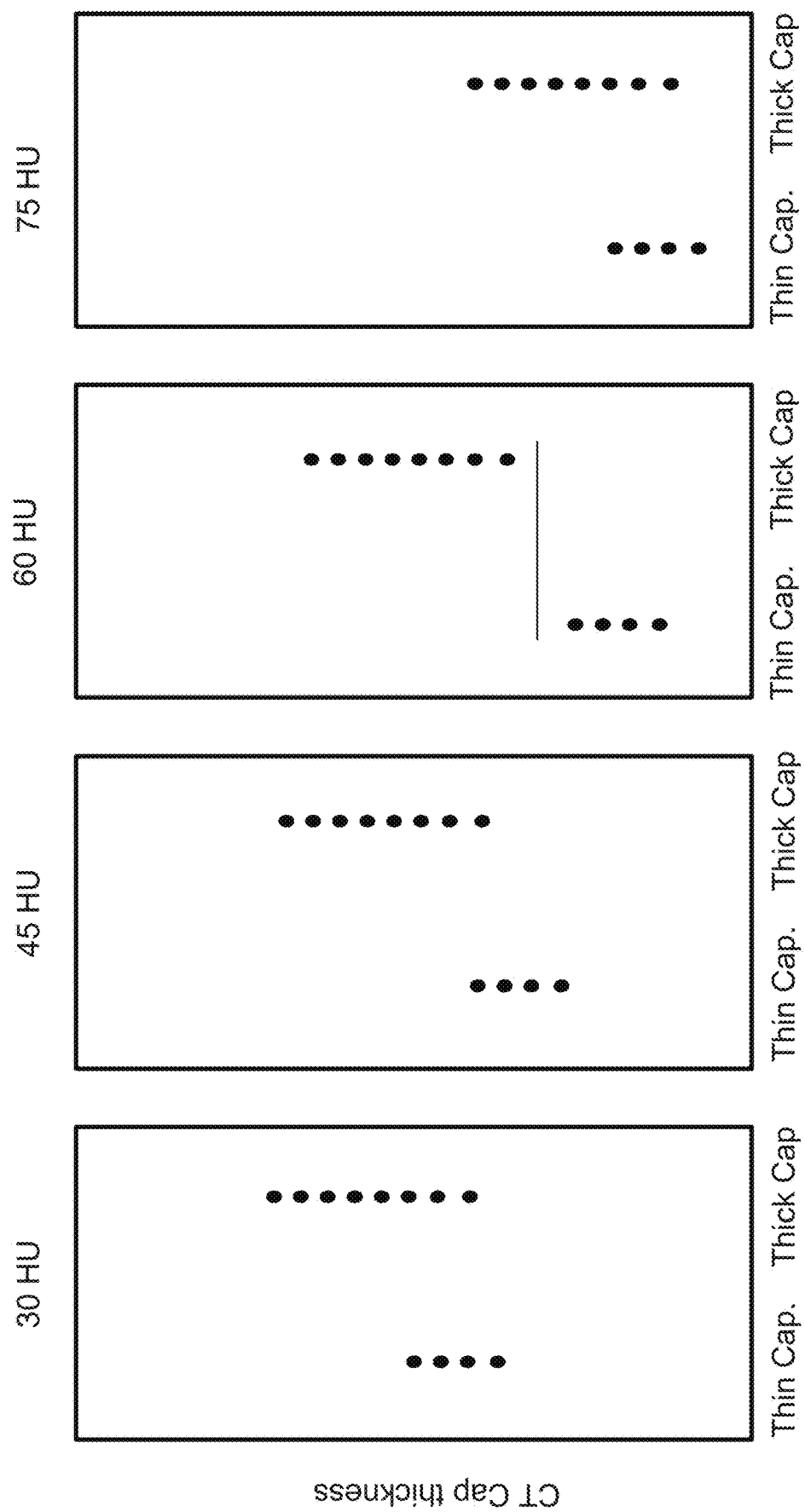
FIG. 23 illustrates an example of the separation between thin cap and thick cap fibroatheromas at different Hounsfield unit thresholds according to some implementations.

FIG. 23 illustrates an example of the separation between thin cap and thick cap fibroatheromas at different Hounsfield unit thresholds according to some implementations. In FIG. 23, the apparent cap thickness using CT can fail to distinguish between thin caps and thick caps, depending upon the chosen threshold. For example, at a threshold of 30 HU, thin caps can appear to be thick, and at 75 HU, thick caps can appear to be thin. In the illustrated example, at 60 HU, there is a clean separation between thin cap fibroatheromas and thick cap fibroatheromas, enabling the two to be readily distinguished from one another. It will be appreciated that FIG. 23 is merely for illustrative purposes. In practice, the actual thresholds can be different from those depicted in FIG. 23.

Figure 24:
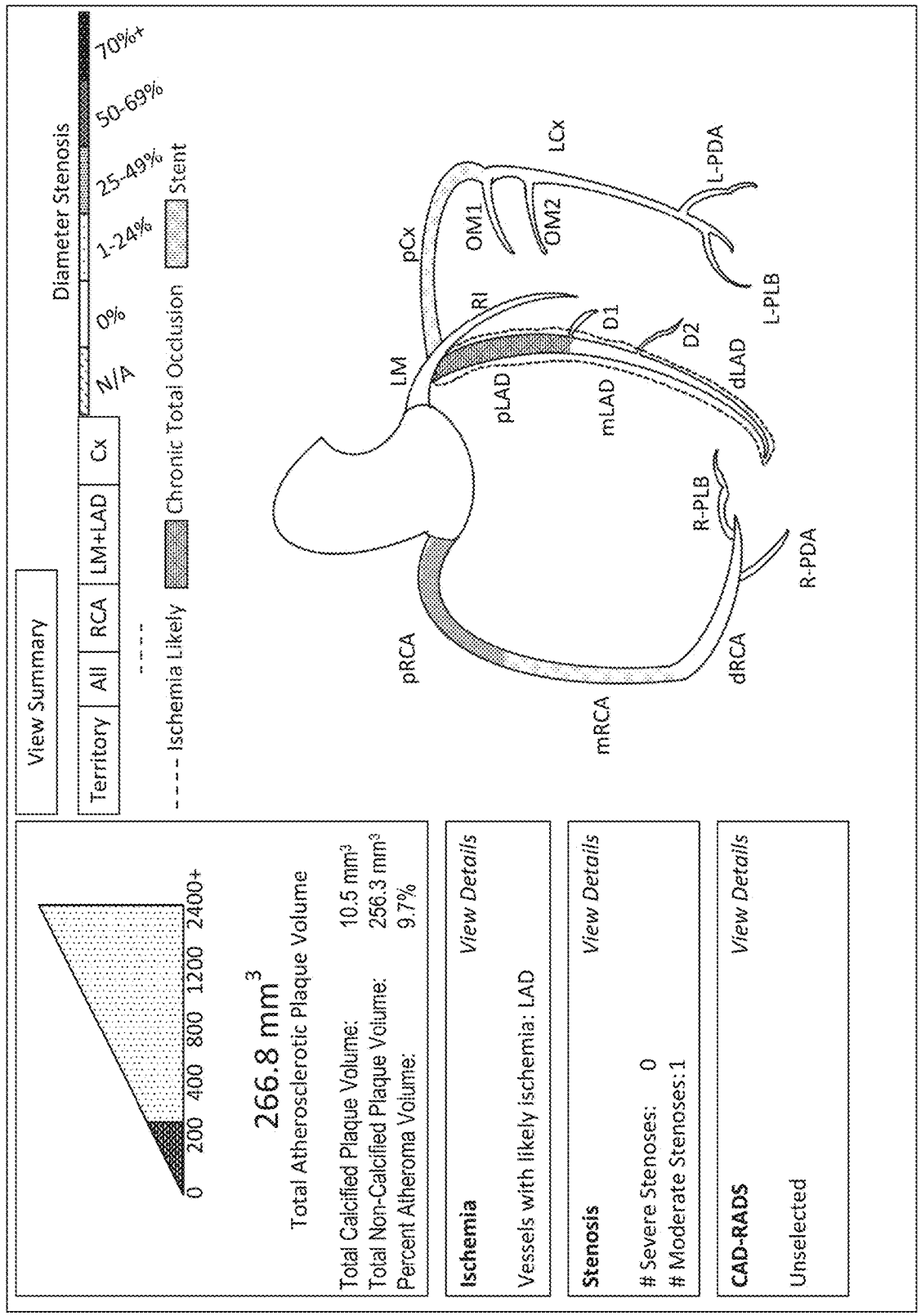
FIG. 24 is a drawing that illustrates an example user interface according to some implementations.

FIG. 24 is a drawing that illustrates an example user interface according to some implementations. In FIG. 24, a coronary artery tree is illustrated. In some implementations, anatomical labels can be shown on the coronary artery tree. In some implementations, portions of the coronary artery tree can be shaded, highlighted, colored, or otherwise marked so as to display clinically relevant information. For example, in some implementations, portions of the coronary artery tree can be colored or otherwise differentiated to indicate a level of diameter stenosis. In some implementations, areas of chronic total occlusion can be indicated (e.g., by coloring). In some implementations, areas that have been stented can be indicated. In some implementations, areas of likely ischemia can be identified. In some implementations, the user interface can show a total atherosclerotic plaque volume, total calcified plaque volume, total non-calcified plaque volume, percent atheroma volume, and/or any other clinically relevant information. In some implementations, the user interface can identify vessels with likely ischemia. For example, in FIG. 24, the left anterior descending vessel is identified as likely ischemic. In some implementations, the user interface can identify severe stenoses and/or moderate stenoses. In some implementations, the user interface can show Coronary Artery Disease-Reporting and Data System (CAD-RADS) information. In some implementations, the user interface can include links or other user interface elements to view additional details. In some implementations, the user interface can include a selector for selecting a territory for visualization and/or analysis (e.g., All, RCA, LM+LAD, Cx, etc.).

Figure 25:
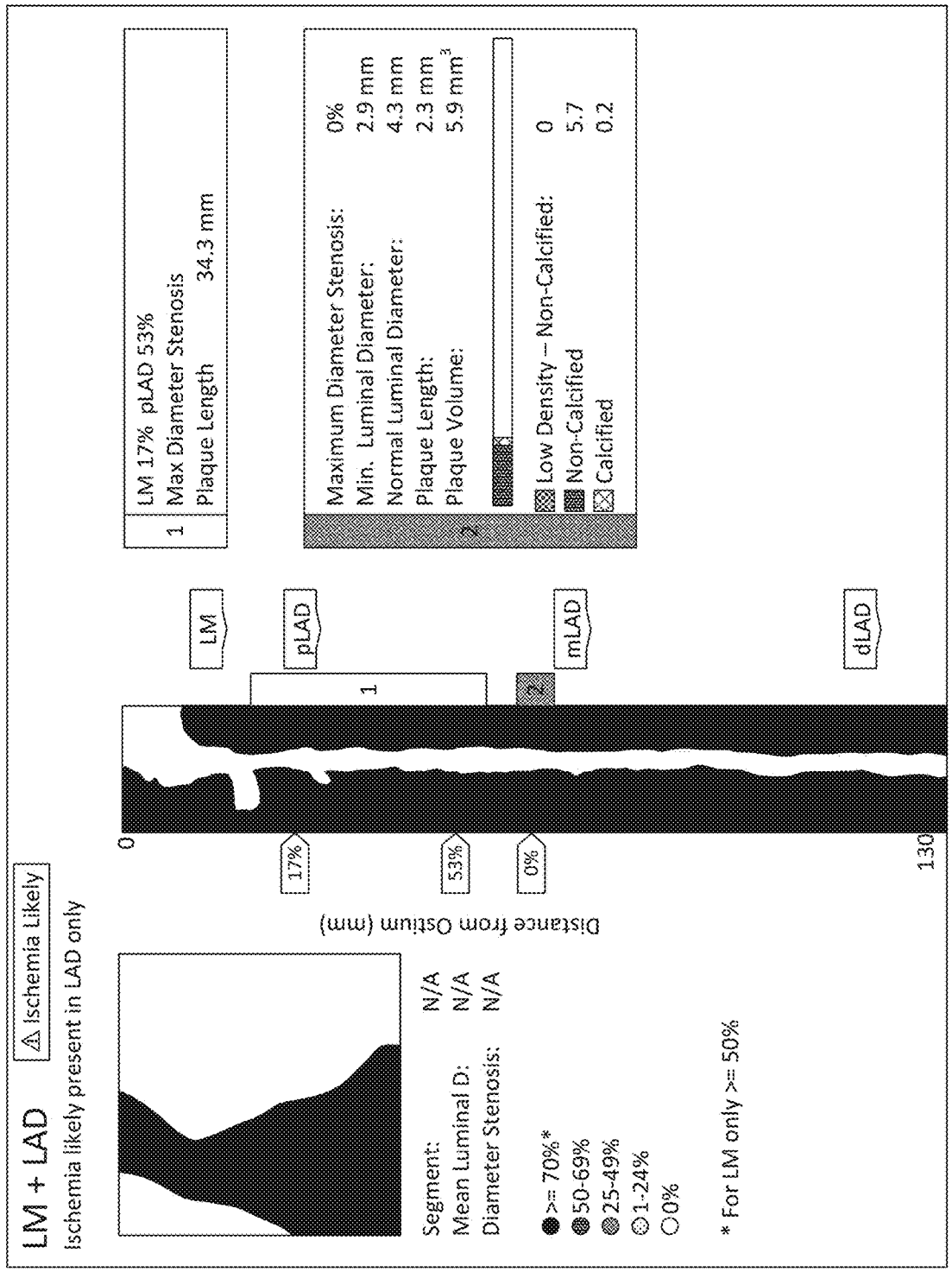
FIG. 25 is a drawing that illustrates another example user interface according to some implementations.

FIG. 25 is a drawing that illustrates another example user interface according to some implementations. The user interface can include a straightened view of an artery (in FIG. 24, LM+LAD). The straightened view can be augmented with various labels (also referred to herein as markers). For example, numerical labels or location markers can be added to the straightened view to show the location of lesions, for example the distance of lesions from the ostium. In some implementations, anatomical labels can be added to the straightened view. For example, in FIG. 8, labels are provided that indicate the left main artery, proximal left anterior descending, medial left anterior descending, and distal left anterior descending. In some implementations, labels can show the position of a maximum diameter stenosis and the value of the maximum diameter stenosis. For example in FIG. 8, for the first lesion, the maximum diameter stenosis in the left main artery is 17% and the maximum diameter stenosis in the proximal left anterior descending is 53%.

In some implementations, the user interface can include a detailed view. A segment, mean luminal diameter, diameter stenosis, and so forth can be provided for the detailed view. In some implementations, the detailed view can be shaded, color-coded, or otherwise can indicate a level of diameter stenosis.

Information boxes can be provided in the user interface. The information boxes can provide information about each observed lesion. In some implementations, a user can click on or otherwise select a lesion in the straightened view to expand the corresponding information box. In some implementations, the user can select an information box and the corresponding lesion can be highlighted or otherwise selected in the straightened view.

Figure 26:
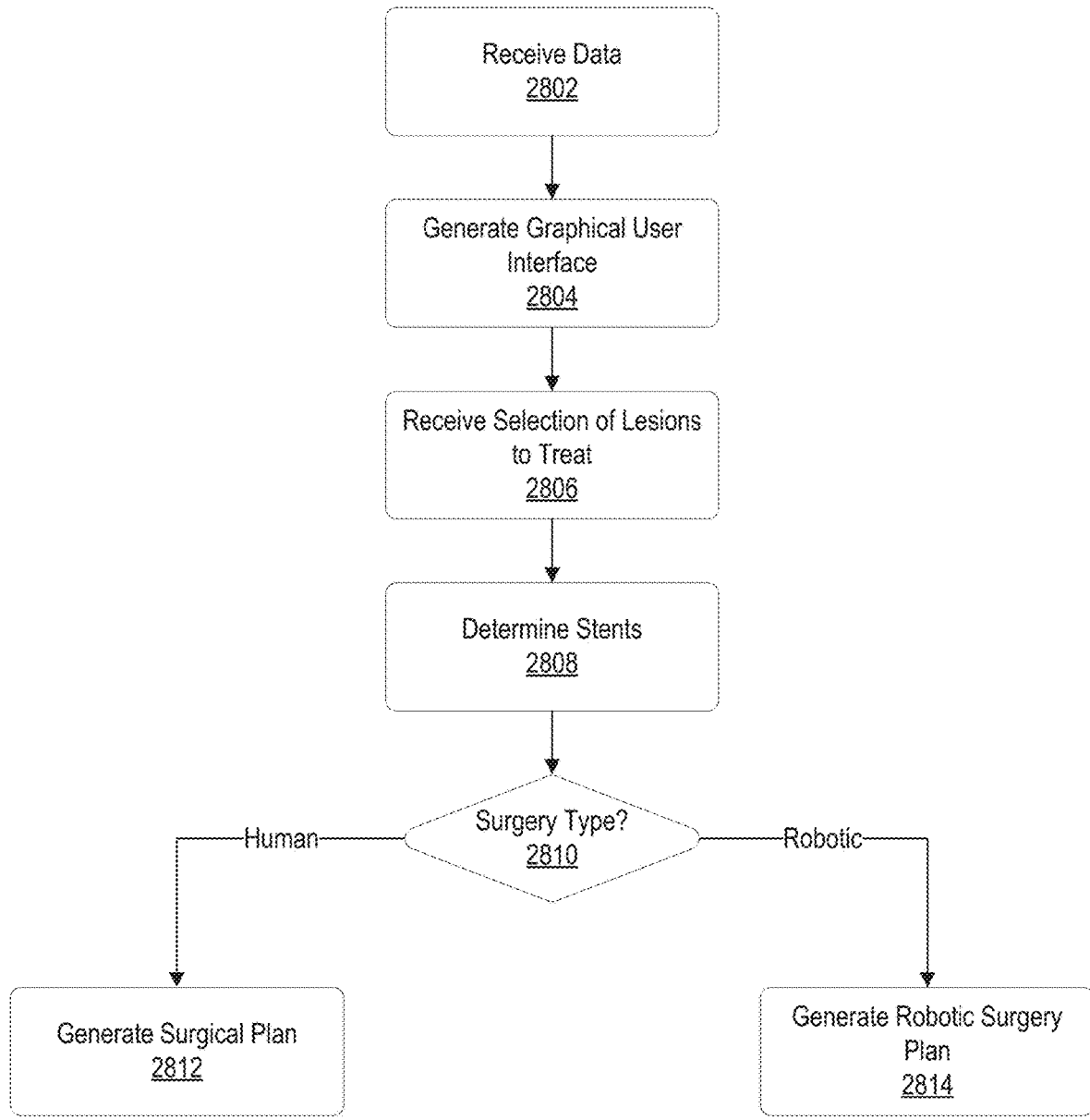
FIG. 26 is a flowchart that illustrates an example process for generating a surgical plan according to some implementations.

FIG. 26 is a flowchart that illustrates an example process for generating a surgical plan according to some implementations. The process shown in FIG. 26 can be carried out on a computer system. At operation 2802, the system can receive data, for example CCTA image(s), OCT data, IVUS data, near infrared spectroscopy data, and so forth. At operation 2804, the system can generate a graphical user interface indicating one or more lesions. At operation 2806, the system can receive a user selection of one or more lesions to treat. At operation 2808, the system can determine one or more stents. For example, the system can determine one or more stent lengths, stent diameters, stent materials, stent structures, etc. At operation 2810, the system can determine a surgery type. If the surgery is to be performed by a human, the system can generate a surgical plan at operation 2812. If the surgery is to be performed robotically, the system can generate a robotic surgery plan at operation 2814.

Example Embodiments

In one or more aspects, the techniques described herein relate to a computer-implemented method for plaque regression classification, the computer-implemented method including: receiving a first medical image, the first medical image showing a first region of plaque; receiving a second medical image, the second medical image showing a second region of plaque; identifying the first region of plaque in the first medical image; identifying the second region of plaque in the second medical image; determining a first set of one or more properties for the first region of plaque; determining a second set of one or more properties for the second region of plaque; comparing at least one property of the first set of properties to at least one corresponding property of the second set of properties; determining, based on the comparing, a regression of plaque between the first medical image and the second medical image; and determining, based on the comparing, a classification of the regression of plaque.

In one or more aspects, the techniques described herein relate to a computer-implemented method, wherein the first region of plaque and the second region of plaque are a same region of plaque.

In one or more aspects, the techniques described herein relate to a computer-implemented method, further including: co-registering the first image and the second image.

In one or more aspects, the techniques described herein relate to a computer-implemented method, wherein the classification is one of regression or pseudo regression.

In one or more aspects, the techniques described herein relate to a computer-implemented method, wherein the classification is one of true regression, pseudo regression, stasis, or growth.

In one or more aspects, the techniques described herein relate to a computer-implemented method, wherein the first set of properties includes a first plaque mass, wherein the second set of properties includes a second plaque mass, wherein comparing includes determining a difference between the first plaque mass and the second plaque mass, wherein a pseudo regression is characterized by the difference being below a threshold value, and wherein a true regression is characterized by the first plaque mass being greater than the second plaque mass by at least the threshold value.

In one or more aspects, the techniques described herein relate to a computer-implemented method, wherein the first plaque mass is defined as a product of a first density and a first volume, and wherein the second plaque mass is defined as a product of a second density and a second volume.

In one or more aspects, the techniques described herein relate to a computer-implemented method, wherein the first density and the second density include material density or radiodensity.

In one or more aspects, the techniques described herein relate to a computer-implemented method, wherein the first set of one or more properties and the second set of one or more properties each include at least one of: total plaque volume, total plaque area, total plaque length, high density plaque volume, high density plaque area, high density plaque length, low density plaque volume low density plaque area, low density plaque length, material density, or radiodensity.

In one or more aspects, the techniques described herein relate to a computer-implemented method, wherein the first set of one or more properties and second set of one or more includes each include total plaque mass, wherein the total plaque mass is determined by a product of material density and total plaque volume.

In one or more aspects, the techniques described herein relate to a computer-implemented method, further including: causing display of the classification to a user via a graphical user interface.

In one or more aspects, the techniques described herein relate to a computer-implemented method for plaque regression classification, the computer-implemented method including: receiving a first medical image, the first medical image showing a first region of plaque; receiving a second medical image, the second medical image showing a second region of plaque; providing a representation of the first medical image and the second medical image to a machine learning model, wherein the model is configured to analyze the first medical image and the second medical image to determine a regression classification; determining, using the machine learning model, a classification of a plaque regression between the first medical image and the second medical image.

In one or more aspects, the techniques described herein relate to a computer-implemented method, wherein the machine learning model is trained using supervised learning on image pairs showing true regression and pseudo regression.

In one or more aspects, the techniques described herein relate to a computer-implemented method, wherein a first image of an image pair of the image pairs and a second image of an image pair of the image pairs show a same region of plaque.

In one or more aspects, the techniques described herein relate to a computer-implemented method, wherein the first image and the second image are captured at different points in time.

In one or more aspects, the techniques described herein relate to a computer-implemented method, wherein the first image is captured at an earlier point in time than the second image.

In one or more aspects, the techniques described herein relate to a computer-implemented method, wherein the regression classification is selected from true regression or pseudo regression.

In one or more aspects, the techniques described herein relate to a computer-implemented method, wherein the regression classification is selected from true regression, pseudo regression, stasis, or growth.

In one or more aspects, the techniques described herein relate to a computer-implemented method, further including: causing display of the plaque regression classification to a user via a graphical user interface.

In one or more aspects, the techniques described herein relate to a computer-implemented method for facilitating determination of arterial disease treatment for a patient having an arterial disease based at least in part on medical image analysis, the computer-implemented method including: accessing, by a computer system, a medical image of a patient, the medical image including a representation of one or more arteries, the one or more arteries including one or more regions of plaque; analyzing, by the computer system, the medical image to identify the one or more arteries and the one or more regions of plaque; determining, by the computer system, a total volume of plaque based at least in part on the identified one or more regions of plaque; assessing, by the computer system, expected therapeutic benefit from systemic therapy based at least in part on the total volume of plaque for the patient; determining, by the computer system, presence and extent of high-risk plaque based at least in part on one or more densities of the identified one or more regions of plaque; assessing, by the computer system, an expected therapeutic benefit from local intervention based at least in part on the presence and extent of high-risk plaque; determining, by the computer system, a recommended arterial disease treatment for the patient based on the assessed expected therapeutic benefit from local intervention and the assessed expected therapeutic benefit from systemic therapy, wherein the computer system includes a computer processor and an electronic storage medium.

In one or more aspects, the techniques described herein relate to a computer-implemented method, wherein the recommended arterial disease treatment includes one or more of systemic therapy or local intervention, wherein the recommended arterial disease treatment includes systemic therapy when the total volume of plaque is above a first predetermined threshold, and wherein the recommended arterial disease treatment includes local intervention when the presence and extent of high-risk plaque is above a second predetermined threshold.

In one or more aspects, the techniques described herein relate to a computer-implemented method, wherein the recommended arterial disease treatment includes both local treatment and systemic treatment.

In one or more aspects, the techniques described herein relate to a computer-implemented method, further including determining an appropriate type or level of systemic treatment, wherein the recommended arterial disease treatment for the patient includes the appropriate type or level of systemic treatment.

In one or more aspects, the techniques described herein relate to a computer-implemented method, wherein one or more of the first predetermined threshold or the second predetermined threshold is determined using a machine learning algorithm.

In one or more aspects, the techniques described herein relate to a computer-implemented method, wherein systemic treatment includes one or more of medication, lifestyle, or dietary treatment.

In one or more aspects, the techniques described herein relate to a computer-implemented method, wherein local intervention includes one or more of percutaneous coronary intervention (PCI) or coronary artery bypass grafting (CABG).

In one or more aspects, the techniques described herein relate to a computer-implemented method, further including determining one or more recommended parameters for a local treatment.

In one or more aspects, the techniques described herein relate to a computer-implemented method, wherein the one or more recommended parameters includes one or more of: dimensions, type, or material of a stent.

In one or more aspects, the techniques described herein relate to a computer-implemented method, wherein the arterial disease includes coronary artery disease (CAD).

In one or more aspects, the techniques described herein relate to a computer-implemented method, wherein the medical image includes a coronary computed tomography angiography (CCTA) image.

In one or more aspects, the techniques described herein relate to a computer-implemented method, wherein the one or more densities include material density.

In one or more aspects, the techniques described herein relate to a computer-implemented method, wherein the one or more densities include radiodensity.

In one or more aspects, the techniques described herein relate to a computer-implemented method, wherein high-risk plaque is determined on a lesion level.

In one or more aspects, the techniques described herein relate to a computer-implemented method, further including: generating a patient-level risk score for the patient based at least in part on the determined total volume of plaque for the patient; and generating a lesion-level risk score for the patient based at least in part on the determined presence and extent of high-risk plaque, wherein the recommended arterial disease treatment is determined based at least in part on the patient-level risk score and the lesion-level risk score.

In one or more aspects, the techniques described herein relate to a computer-implemented method of normalizing a computed tomography (CT) image without using a physical calibration device for analysis of one or more plaque or vascular parameters, the method including: accessing, by a computer system, a CT image of a patient, the CT image including a representation of one or more arteries, the one or more arteries including one or more regions of plaque; accessing, by the computer system, one or more image acquisition parameters used to obtain the CT image, the one or more image acquisition parameters including one or more of method of helical CT, type of CT detector, type of CT based on number of photon energy spectra, current (mA), peak kilovoltage (kVp), image noise, signal, signal to noise ratio, contrast opacification, or contrast to noise ratio; and normalizing, by the computer system, the CT image by applying an image processing algorithm to the CT image without using a physical calibration device, wherein the image processing algorithm is derived from analyzing a plurality of test CT images obtained from a same subject and the one or more image acquisition parameters used to obtain the plurality test CT images, wherein the plurality of test CT images includes one or more arteries including one or more regions of plaque; wherein the normalized CT image is configured to be analyzed to generate one or more plaque parameters and one or more vascular parameters, wherein the one or more plaque parameters includes one or more of total plaque volume, non-calcified plaque volume, or calcified plaque volume, and wherein the one or more vascular parameters includes one or more lumen measurements, wherein the one or more plaque parameters and the one or more vascular parameters generated from the normalized CT image are configured to be compared to one or more plaque parameters and one or more vascular parameters generated from a second CT image of the patient, and wherein the computer system includes a computer processor and an electronic storage medium.

In one or more aspects, the techniques described herein relate to a computer-implemented method, wherein the method of helical CT includes one or more of single source, dual source, multi-source, fast switching, or fast pitch helical.

In one or more aspects, the techniques described herein relate to a computer-implemented method, wherein the type of CT detector includes one or more of an energy integrating detector or a photon counting detector.

In one or more aspects, the techniques described herein relate to a computer-implemented method, wherein the type of CT based on number of photon energy spectra includes one or more of a single energy CT, dual energy CT, spectral CT, or multispectral CT.

In one or more aspects, the techniques described herein relate to a computer-implemented method, wherein the two or more test CT images are obtained using one or more different image acquisition parameters.

In one or more aspects, the techniques described herein relate to a computer-implemented method, wherein the two or more test CT images are obtained at two or more different points in time.

In one or more aspects, the techniques described herein relate to a computer-implemented method, wherein the image processing algorithm includes a polynomial regression equation.

In one or more aspects, the techniques described herein relate to a computer-implemented method, wherein the image processing algorithm includes a linear regression equation.

In one or more aspects, the techniques described herein relate to a computer-implemented method, wherein the image processing algorithm includes a machine learning algorithm.

In one or more aspects, the techniques described herein relate to a computer-implemented method, wherein the image processing algorithm includes a mathematical algorithm.

In one or more aspects, the techniques described herein relate to a computer-implemented method, wherein one or more of the image acquisition parameters linearly affect the CT image.

In one or more aspects, the techniques described herein relate to a computer-implemented method, wherein one or more of the image acquisition parameters nonlinearly affect the CT image.

In one or more aspects, the techniques described herein relate to a computer-implemented method, wherein the second CT image of the patient is obtained at a different point in time than the CT image of the patient.

In one or more aspects, the techniques described herein relate to a computer-implemented method, wherein the second CT image of the patient is obtained using one or more different image acquisition parameters than the CT image of the patient.

In one or more aspects, the techniques described herein relate to a computer-implemented method, wherein the CT image includes a coronary computed tomography angiography (CCTA) image.

In one or more aspects, the techniques described herein relate to a computer-implemented method, wherein normalizing the CT image includes normalizing a plurality of CT images, wherein the computer-implemented method further includes: generating, based on the normalized CT image, a coronary artery tree, wherein generating the coronary artery tree includes: extracting, by a computer system from the plurality of normalized CT images, coronary artery vessels; labeling, by the computer system, the extracted vessels; segmenting, by the computer system, an aorta of the patient present in each image of the plurality of normalized CT images; ranking, by the computer system, for each extracted vessel, each image of the plurality of normalized CT images; selecting, by the computer system, for each extracted vessel based on the ranking, an image; and registering, by the computer system, each selected image to generate the tree.

In one or more aspects, the techniques described herein relate to a computer-implemented method of generating an image processing algorithm for normalizing a computed tomography (CT) image without using a physical calibration device for analysis of one or more plaque or vascular parameters, the computer-implemented method including: accessing, by a computer system, a plurality of test CT images obtained from a same subject, wherein the plurality of test CT images include a representation of one or more arteries including one or more regions of atherosclerotic plaque; accessing, by the computer system, one or more image acquisition parameters used to obtain the plurality of test CT images, the one or more image acquisition parameters including one or more of method of helical CT, type of CT detector, type of CT based on number of photon energy spectra, current (mA), peak kilovoltage (kVp), image noise, signal, signal to noise ratio, contrast opacification, or contrast to noise ratio; generating, by the computer system, an image processing algorithm for normalizing a CT image of a patient based at least in part on the plurality test CT images and the one or more image acquisition parameters used to obtain the plurality of test CT images and without using a physical calibration device, wherein the image processing algorithm is configured to be used to normalize the CT image of the patient based at least in part on the one or more image acquisition parameters used to obtain the CT image without using a physical calibration device, wherein the normalized CT image is configured to be analyzed to generate one or more plaque parameters and one or more vascular parameters, wherein the one or more plaque parameters includes one or more of total plaque volume, non-calcified plaque volume, or calcified plaque volume, and wherein the one or more vascular parameters includes one or more lumen measurements, wherein the one or more plaque parameters and the one or more vascular parameters generated from the normalized CT image are configured to be compared to one or more plaque parameters and one or more vascular parameters generated from another CT image of the patient, and wherein the computer system includes a computer processor and an electronic storage medium.

In one or more aspects, the techniques described herein relate to a computer-implemented method, wherein the method of helical CT includes one or more of single source, dual source, multi-source, fast switching, or fast pitch helical.

In one or more aspects, the techniques described herein relate to a computer-implemented method, wherein the type of CT detector includes one or more of an energy integrating detector or a photon counting detector.

In one or more aspects, the techniques described herein relate to a computer-implemented method, wherein the type of CT based on number of photon energy spectra includes one or more of a single energy CT, dual energy CT, spectral CT, or multispectral CT.

In one or more aspects, the techniques described herein relate to a computer-implemented method, wherein the two or more test CT images are obtained using one or more different image acquisition parameters.

In one or more aspects, the techniques described herein relate to a computer-implemented method, wherein the two or more test CT images are obtained at two or more different points in time.

In one or more aspects, the techniques described herein relate to a computer-implemented method, wherein the image processing algorithm includes a polynomial regression equation.

In one or more aspects, the techniques described herein relate to a computer-implemented method, wherein the image processing algorithm includes a regression equation.

In one or more aspects, the techniques described herein relate to a computer-implemented method, wherein the image processing algorithm includes a machine learning algorithm.

In one or more aspects, the techniques described herein relate to a computer-implemented method, wherein the image processing algorithm includes a mathematical algorithm.

In one or more aspects, the techniques described herein relate to a computer-implemented method, wherein one or more of the image acquisition parameters linearly affect a CT image.

In one or more aspects, the techniques described herein relate to a computer-implemented method, wherein one or more of the image acquisition parameters nonlinearly affect a CT image.

In one or more aspects, the techniques described herein relate to a computer-implemented method, wherein the another CT image of the patient is obtained at a different point in time than the CT image of the patient.

In one or more aspects, the techniques described herein relate to a computer-implemented method, wherein the another CT image of the patient is obtained using one or more different image acquisition parameters than the CT image of the patient.

In one or more aspects, the techniques described herein relate to a computer-implemented method, wherein the CT image includes a coronary computed tomography angiography (CCTA) image.

In one or more aspects, the techniques described herein relate to a computer-implemented method of risk stratification of coronary artery disease (CAD) based on image analysis of one or more coronary arteries of a subject, the computer-implemented method including: accessing, by a computer system, a medical image of a subject showing one or more coronary arteries; analyzing, by the computer system, the medical image to determine one or more areas of stenosis in the one or more coronary arteries; analyzing, by the computer system, the medical image to determine one or more areas of atherosclerosis in the one or more coronary arteries; analyzing, by the computer system, the medical image to determine one or more areas of ischemia in the one or more coronary arteries; and generating, by the computer system, a risk stratification of major adverse cardiovascular event (MACE) for the subject based at least in part on the one or more areas of stenosis, the one or more areas of atherosclerosis, and the one or more areas of ischemia, wherein the computer system includes a computer processor and an electronic storage medium.

In one or more aspects, the techniques described herein relate to a computer-implemented method, wherein the risk stratification of MACE for the subject is generated by inputting the one or more areas of stenosis, the one or more areas of atherosclerosis, and the one or more areas of ischemia into a machine learning algorithm.

In one or more aspects, the techniques described herein relate to a computer-implemented method, wherein the risk stratification of MACE for the subject includes a CAD risk staging.

In one or more aspects, the techniques described herein relate to a computer-implemented method, wherein the risk stratification of MACE for the subject is generated based at least in part on risk stratification of MACE of a plurality of subjects based on one or more of: one or more areas of stenosis, one or more areas of atherosclerosis, or one or more areas of ischemia identified from one or more medical images collected from the plurality of subjects.

In one or more aspects, the techniques described herein relate to a computer-implemented method, wherein the one or more areas of ischemia in the one or more coronary arteries is determined based at least in part on the one or more areas of stenosis and the one or more areas of atherosclerosis.

In one or more aspects, the techniques described herein relate to a computer-implemented method, wherein the one or more areas of ischemia in the one or more coronary arteries is determined using a machine learning algorithm.

In one or more aspects, the techniques described herein relate to a computer-implemented method for constructing a coronary artery tree of a patient including: extracting, by a computer system from a plurality of image series, coronary artery vessels; labeling, by the computer system, the extracted vessels; segmenting, by the computer system, an aorta of the patient present in each image series of the plurality of image series; ranking, by the computer system, for each extracted vessel, each series of the plurality of image series; selecting, by the computer system, for each extracted vessel based on the ranking, an image series; and registering, by the computer system, each selected image series to generate the tree.

In one or more aspects, the techniques described herein relate to a computer-implemented method, wherein the plurality of image series includes a plurality of coronary computed tomography angiography (CCTA) images.

In one or more aspects, the techniques described herein relate to a computer-implemented method, further including determining an overlap ratio.

In one or more aspects, the techniques described herein relate to a computer-implemented method, wherein each series of the plurality of series corresponds to a cardiac phase.

In one or more aspects, the techniques described herein relate to a computer-implemented method, wherein ranking each series for each extracted vessel includes straightening each extracted vessel.

In one or more aspects, the techniques described herein relate to a computer-implemented method, wherein ranking each series for each extracted includes providing the straightened extracted vessels to a machine learning model, wherein the machine learning model is trained to select a best series from the plurality of series.

In one or more aspects, the techniques described herein relate to a computer-implemented method, wherein selecting the best series includes selecting a series that minimizes one or more of blur or noise.

In one or more aspects, the techniques described herein relate to a computer-implemented method, wherein selecting the best series includes selecting a series that maximizes contrast.

In one or more aspects, the techniques described herein relate to a computer-implemented method, wherein to register each selected image series to generate the coronary artery tree, the method includes determining a common reference.

In one or more aspects, the techniques described herein relate to a computer-implemented method, wherein the common reference includes at least a portion of an aorta of the patient.

In one or more aspects, the techniques described herein relate to a computer-implemented method, wherein the common reference includes one or more coronary artery ostia.

In one or more aspects, the techniques described herein relate to a computer-implemented method, further including generating the coronary artery tree includes stitching a plurality of segments at a plurality of bifurcation landmarks.

In one or more aspects, the techniques described herein relate to a computer-implemented method, further including: overlying a graphical representation of one or more plaques on the generated coronary artery tree.

In one or more aspects, the techniques described herein relate to a computer-implemented method, further including: performing, based at least in part on the generated coronary artery tree, a fractional flow reserve-computed tomography (FFR-CT) calculation.

In one or more aspects, the techniques described herein relate to a computer-implemented method, further including: generating, based at least in part on the generated coronary artery tree, a visualization of a myocardial mass at risk.

In one or more aspects, the techniques described herein relate to a computer-implemented method, further including simulating a virtual myocardial perfusion map.

In one or more aspects, the techniques described herein relate to a computer-implemented method, further including simulating a quantitative myocardial blood flow for a heart.

In one or more aspects, the techniques described herein relate to a computer-implemented method including: receiving a first set of images; receiving a second set of images, wherein the second set of images includes a plurality of coronary computed tomography angiography images, wherein the second set of images has a plurality of peak kilovoltages associated therewith, wherein the second set of images has a plurality of lumen contrast values associated therewith, and wherein each image of the second set of images is associated with a corresponding image of the first set of images to form a plurality of image pairs; determining, for each first image of the first set of images, a first size of a calcified plaque in the first image; determining, for each second image of the second set of images, a second size of the calcified plaque in the second image; for each image pair of the plurality of image pairs: adjusting a plaque calcification threshold of the second image of the image pair, wherein adjusting the plaque calcification threshold causes a change in the determined second size of the calcified plaque in the second image; determining the lumen contrast associated with a lumen of a vessel in the second image; and determining the peak kilovoltage associated with the second image; determining, based on the lumen contrast, the peak kilovoltage, and the plaque calcification threshold of each second image, a resulting plaque calcification threshold for each combination of lumen contrast and peak kilovoltage associated with the second set of images.

In one or more aspects, the techniques described herein relate to a computer-implemented method, wherein the first size and the second size include at least one of: a volume, an area, or a thickness of the calcified plaque.

In one or more aspects, the techniques described herein relate to a computer-implemented method, wherein determining the resulting plaque calcification threshold for each combination of lumen contrast and peak kilovoltage includes: determining, for each combination of lumen contrast and peak kilovoltage, an average plaque calcification threshold.

In one or more aspects, the techniques described herein relate to a computer-implemented method, wherein determining the resulting plaque calcification threshold for each combination of lumen contrast and peak kilovoltage includes removing one or more outlier plaque calcification thresholds.

In one or more aspects, the techniques described herein relate to a computer-implemented method, wherein the first set of images includes a set of near infrared x-ray spectroscopy images.

In one or more aspects, the techniques described herein relate to a computer-implemented method, further including: determining, based on the resulting plaque calcification thresholds for each combination of lumen contrast and peak kilovoltage, an equation configured to output a computed plaque calcification threshold for a provided lumen contrast and peak kilovoltage.

In one or more aspects, the techniques described herein relate to a computer-implemented method for determining a calcified plaque size, the computer-implemented method including: receiving a coronary computed tomography angiography image; identifying a lumen in the coronary computed tomography angiography image; determining a lumen contrast of the lumen; determining a peak kilovoltage associated with the coronary computed tomography image; adjusting a plaque calcification threshold for identifying calcified plaque and non-calcified plaque, wherein the adjusting is based on a plaque calcification threshold value determined by analyzing a plurality of image pairs, wherein each image pair includes a coronary computed tomography angiography image and a ground truth image; and determining the calcified plaque size, wherein determining the calcified plaque size includes determining an amount of plaque above the plaque calcification threshold.

In one or more aspects, the techniques described herein relate to a computer-implemented method, wherein the calcified plaque size is a volume, and wherein the volume is determined by determining a volume of plaque above the plaque calcification threshold.

In one or more aspects, the techniques described herein relate to a computer-implemented method, wherein the calcified plaque size is an area, and wherein the area is determined by determining an area of plaque above the plaque calcification threshold.

In one or more aspects, the techniques described herein relate to a computer-implemented method, wherein the calcified plaque size is a thickness, and wherein the thickness is determined by length of plaque above the plaque calcification threshold.

In one or more aspects, the techniques described herein relate to a computer-implemented method including: receiving a first set of images; receiving a second set of images, wherein the second set of images includes a plurality of coronary computed tomography angiography (CCTA) images, wherein the second set of images has a plurality of peak kilovoltages associated therewith, wherein the second set of images has a plurality of lumen contrast values associated therewith, and wherein each image of the second set of images is associated with a corresponding image of first set of images to form a plurality of image pairs; determining, for each first image of the first set of images, a presence of thin cap fibroatheroma (TCFA); determining, for each second image of the second set of images, a proximity of low attention plaque (LAP) to a boundary between a plaque and a lumen; for each image pair of the plurality of image pairs: adjusting a LAP threshold of the second image of the image pair, wherein adjusting the LAP threshold causes a change in the proximity of LAP to the boundary; determining the lumen contrast associated with the lumen in the second image; and determining the peak kilovoltage associated with the second image; determining, based on the lumen contrast, the peak kilovoltage, and the LAP threshold of each second image, a resulting LAP threshold for each combination of lumen contrast and peak kilovoltage associated with the second set of images.

In one or more aspects, the techniques described herein relate to a computer-implemented method, wherein the first set of images includes a plurality of optical coherence tomography images.

In one or more aspects, the techniques described herein relate to a computer-implemented method, wherein determining the resulting LAP threshold for each combination of lumen contrast and peak kilovoltage includes determining, for each combination of lumen contrast and peak kilovoltage, an average plaque calcification threshold.

In one or more aspects, the techniques described herein relate to a computer-implemented method, wherein determining the resulting LAP threshold for each combination of lumen contrast and peak kilovoltage includes removing one or more outlier LAP thresholds.

In one or more aspects, the techniques described herein relate to a computer-implemented method, wherein determining the resulting LAP threshold for each combination of lumen contrast and peak kilovoltage includes binning the peak kilovoltages.

In one or more aspects, the techniques described herein relate to a computer-implemented method, wherein a bin size is 10 HU, 20 HU, 30 HU, 40 HU, 50 HU, 60 HU, 70 HU, 80 HU, 90 HU, or 100 HU.

In one or more aspects, the techniques described herein relate to a computer-implemented method for identifying thin cap fibroatheroma (TCFA) including: receiving, by a computer system, a coronary computed tomography angiography (CCTA) image; identifying, by the computer system, a lumen contrast of a lumen in the CCTA image; identifying, by the computer system, a peak kilovoltage associated with the CCTA image; adjusting, by the computer system, a low attenuation plaque (LAP) threshold based on the lumen contrast and the peak kilovoltage; identifying, by the computer system, a proximity of low attenuation to the lumen; and determining, by the computer system, a presence of TCFA based on the proximity.

In one or more aspects, the techniques described herein relate to a computer-implemented method, wherein the LAP threshold is determined by: receiving, by the computer system, a first set of images; receiving, by the computer system, a second set of images, wherein the second set of images includes a plurality of coronary computed tomography angiography images, wherein the second set of images has a plurality of peak kilovoltages associated therewith, wherein the second set of images has a plurality of lumen contrast values associated therewith, and wherein each image of the second set of images is associated with a corresponding image of the first set of images to form a plurality of image pairs; determining, for each first image of the first set of images, a first size of a calcified plaque in the first image; determining, for each second image of the second set of images, a second size of the calcified plaque in the second image; for each pair of the plurality of image pairs: adjusting a plaque calcification threshold of the second image of the image pair, wherein adjusting the plaque calcification threshold causes a change in the determined second size of the calcified plaque in the second image; determining a lumen contrast associated with a lumen of a vessel in the second image; and determining the peak kilovoltage associated with the second image; determining, based on the lumen contrast, the peak kilovoltage, and the plaque calcification threshold of each second image, a LAP threshold for each combination of lumen contrast and peak kilovoltage associated with the second set of images.

In one or more aspects, the techniques described herein relate to a computer-implemented method, wherein the second set of images has a plurality of peak kilovoltages associated therewith.

In one or more aspects, the techniques described herein relate to a computer-implemented method, wherein the second set of images has a plurality of lumen contrast values associated therewith.

In one or more aspects, the techniques described herein relate to a computer-implemented method for training a machine learning model to identify thin cap fibroatheroma (TCFA), the computer-implemented method including: receiving a set of coronary computed tomography angiography images, each image having a peak kilovoltage and a label indicating a presence of TCFA associated therewith; and training, using supervised learning, the machine learning model to identify TCFA, wherein the machine learning model accepts a CCTA image and a peak kilovoltage as inputs and is trained to output a probability that the CCTA image shows TCFA, wherein the training includes adjusting one or more weights associated with the machine learning model.

In one or more aspects, the techniques described herein relate to a computer-implemented method for identifying thin cap fibroatheroma (TCFA) using a machine learning model including: receiving, by a computer system, a coronary computed tomography angiography (CCTA) image; receiving, by the computer system, a peak kilovoltage value associated with the CCTA image; generating, by the computer system, a representation of the CCTA image and the peak kilovoltage; applying, by the computer system, the machine learning model to the representation; and determining, by the computer system, an output of the machine learning model, the output indicating a probability that the CCTA image shows TCFA, wherein the machine learning model is trained by: receiving a set of coronary computed tomography angiography images, each image having a peak kilovoltage and a label indicating a presence of TCFA associated therewith; and training using supervised learning, the machine learning to identify TCFA, wherein the machine learning model accepts a CCTA image and a peak kilovoltage and is trained to output a probability that the CCTA image shows TCFA, where the training includes adjusted one or more weights associated with the machine learning model.

In one or more aspects, the techniques described herein relate to a computer-implemented method, further including: determining, by the computer system, that the probability is above a threshold value; and causing display to a user of an indication that TCFA is likely.

In one or more aspects, the techniques described herein relate to a computer-implemented method, further including: determining, by the computer system, that the probability is below a threshold value; and causing display to a user of an indication that TCFA is not likely.

In one or more aspects, the techniques described herein relate to a computer-implemented method, further including: causing display to a user of the probability.

In one or more aspects, the techniques described herein relate to a computer-implemented method for providing a graphical user interface for coronary analysis, the method including: receiving coronary data, the coronary data including a straightened coronary computed tomography angiography image and data related to one or more lesions, wherein the lesions correspond to one or more segments of a vessel where plaque is present; generating the graphical user interface including: the straightened coronary computed tomography image; one or more information boxes, each information box corresponding to a lesion of the one or more lesions; one or more location markers indicating a beginning and an end of each lesion of the one or more lesions; and one or more labels, each label corresponding to a lesion of the one or more lesions, each label positioned in relation to the corresponding lesion as shown in the straightened coronary computed tomography image; and providing the graphical user interface for presentation on a computer system of a user.

In one or more aspects, the techniques described herein relate to a computer-implemented method, further including: receiving a selection of a user selection of a lesion of the one or more lesions; and expanding the corresponding information box to display data related to the lesion, wherein a user selects a lesion by selecting a lesion shown on the straightened coronary computed tomography image or selecting an information box of the one or more information boxes.

In one or more aspects, the techniques described herein relate to a computer-implemented method, wherein the data related to the one or more lesions includes at least one of: a maximum diameter stenosis, a minimum luminal diameter stenosis, a plaque length, a plaque volume, or a normal luminal diameter.

In one or more aspects, the techniques described herein relate to a computer-implemented method, wherein the graphical user interface further includes one or more markers, each marker positioned relative to the straightened coronary computed tomography angiography image to indicate a location of a maximum diameter stenosis.

In one or more aspects, the techniques described herein relate to a computer-implemented method, wherein the graphical user interface further includes a scale that shows a distance from a reference point for the straightened coronary computed tomography angiography image.

In one or more aspects, the techniques described herein relate to a computer-implemented method, wherein the reference point is an ostium.

In one or more aspects, the techniques described herein relate to a computer-implemented method, wherein the graphical user interface further includes an indication of a likelihood of ischemia.

In one or more aspects, the techniques described herein relate to a computer-implemented method, wherein the graphical user interface further includes one or more labels corresponding to one or more anatomical features shown in the straightened coronary computed tomography angiography image.

In one or more aspects, the techniques described herein relate to a computer-implemented method, wherein the coronary data further includes at least one of: optical coherence tomography data, near field infrared spectroscopy data, ultrasound data, or invasive angiography data.

In one or more aspects, the techniques described herein relate to a computer-implemented method, wherein the data related to the one or more lesions includes a plaque length and a normal luminal diameter, wherein the distance from the reference point is used to determine a location for placement of a stent, wherein the plaque length and the normal luminal diameter are used to determine a length and a diameter for the stent.

In one or more aspects, the techniques described herein relate to a computer-implemented method, further including: receiving, from the user, a selection of one or more lesions for intervention, wherein the intervention includes placement of one or more stents at each lesion of the one or more lesions; and generating a surgical plan based on the selected one or more lesions, wherein the surgical plan indicates a position for placing each stent, the position corresponding to a distance from a reference point, wherein the surgical plan indicates a diameter of each stent, and wherein the surgical plan indicates a length of each stent.

In one or more aspects, the techniques described herein relate to a computer-implemented method, wherein the surgical plan is a robotic surgery plan including instructions for movement of a surgical robot.

In one or more aspects, the techniques described herein relate to a computer-implemented method, wherein the reference point is selected from an ostium, a left main trifurcation, or a left main bifurcation.

CONCLUSION

In the foregoing specification, the systems and processes have been described with reference to specific embodiments thereof. It will, however, be evident that various modifications and changes may be made thereto without departing from the broader spirit and scope of the embodiments disclosed herein. The specification and drawings are, accordingly, to be regarded in an illustrative rather than restrictive sense.

Indeed, although the systems and processes have been disclosed in the context of certain embodiments and examples, it will be understood by those skilled in the art that the various embodiments of the systems and processes extend beyond the specifically disclosed embodiments to other alternative embodiments and/or uses of the systems and processes and obvious modifications and equivalents thereof. In addition, while several variations of the embodiments of the systems and processes have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed systems and processes. Any methods disclosed herein need not be performed in the order recited. Thus, it is intended that the scope of the systems and processes herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

It will also be appreciated that conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or operations. Thus, such conditional language is not generally intended to imply that features, elements and/or operations are in any way required for one or more embodiments or that one or more embodiments necessarily include logic for deciding, with or without author input or prompting, whether these features, elements and/or operations are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the embodiments are not to be limited to the particular forms or methods disclosed, but, to the contrary, the embodiments are to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (for example, as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (for example, as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

What is claimed is:

1. A computer-implemented method for preoperatively aiding stent selection and surgical planning for coronary revascularization based on image processing analysis of a medical image, the computer-implemented method comprising:

receiving, by a computer system, a multiplanar reconstruction of a coronary computed tomography angiography (CCTA) image of a subject, the multiplanar reconstruction showing one or more lesions, wherein the one or more lesions correspond to one or more segments of a vessel where plaque is present;

identifying, by the computer system, one or more lesions in the multiplanar reconstruction;

identifying plaque in the one or more lesions based at least in part on applying a trained machine learning algorithm to the multiplanar reconstruction;

determining, by the computer system, a lesion for treatment from the one or more lesions, wherein determining the lesion for treatment comprises:
  generating, by the computer system, a graphical user interface comprising the multiplanar reconstruction; and
  receiving, by the computer system, via the graphical user interface a user selection of a lesion of the one or more lesions;

determining, by the computer system, a density of the plaque present in the lesion corresponding to the user selection based at least in part on analyzing radiodensities of image pixels of the multiplanar reconstruction;

preoperatively determining, by the computer system, a stenting procedure for the lesion corresponding to the user selection based at least in part on the determined density of the plaque, wherein the stenting procedure comprises one or more of angioplasty or atherectomy;

preoperatively determining, by the computer system, based at least in part on a normal lumen diameter, a diameter for a stent, wherein the normal lumen diameter is obtained from a segment of the vessel adjacent to the lesion corresponding to the user selection;

preoperatively determining, by the computer system, based on a length of the lesion, a length of the stent, wherein the length of the lesion is determined along an axis generally parallel to a centerline of the vessel, wherein the centerline of the vessel is determined based at least in part on applying the trained machine learning algorithm to the multiplanar reconstruction;

preoperatively determining, by the computer system, based on a location of the lesion, a location for placement of the stent, wherein the location is determined relative to a reference point along the vessel, the reference point comprising one or more of an ostium, bifurcation point, or trifurcation point defined by a morphology of the vessel;

preoperatively generating, by the computer system, a surgical plan comprising the stenting procedure, diameter of the stent, the length of the stent, and the location for placement of the stent; and preoperatively causing, by the computer system, generation of an updated graphical user interface showing the preoperatively generated surgical plan to preoperatively aid stent selection and surgical planning for coronary revascularization, wherein the computer system comprises at least one processor and an electronic storage medium.

2. The computer-implemented method of claim 1, wherein the graphical user interface further comprises data related to the one or more lesions, wherein the data related to the one or more lesions comprises at least one of: a maximum diameter stenosis, a minimum luminal diameter stenosis, a plaque length, a plaque volume, or a normal lumen diameter.

3. The computer-implemented method of claim 1, wherein the graphical user interface further comprises one or more markers, each marker positioned relative to the multiplanar reconstruction to indicate a location of a maximum diameter stenosis.

4. The computer-implemented method of claim 1, wherein the graphical user interface further comprises an indication of a likelihood of ischemia.

5. The computer-implemented method of claim 1, wherein the location for placement of the stent is measured relative to a reference point for the multiplanar reconstruction.

6. The computer-implemented method of claim 1, wherein the graphical user interface further comprises a user input configured to allow a user to select to perform an atherectomy on the selected lesion.

7. The computer-implemented method of claim 1, wherein the reference point comprises a left main trifurcation or a left main bifurcation.

8. The computer-implemented method of claim 1, wherein the surgical plan is a robotic surgery plan, wherein the robotic surgery plan comprises instructions for controlling movement of a surgical robot.

9. The computer-implemented method of claim 1, further comprising:
receiving coronary data, wherein the coronary data comprises at least one of: optical coherence tomography data, near field infrared spectroscopy data, ultrasound data, or invasive angiography data,
wherein the surgical plan is preoperatively generated further based at least in part on the coronary data.

10. A system for preoperatively aiding stent selection and surgical planning for coronary revascularization based on image processing analysis of a medical image, the system comprising:
at least one processor; and
a computer-readable, non-volatile storage medium,
wherein the computer-readable, non-volatile storage medium has instructions stored thereon that, when executed by the at least one processor, cause the system to:
receive a multiplanar reconstruction of a coronary computed tomography angiography image (CCTA image) of a subject, the multiplanar reconstruction showing one or more lesions, wherein the one or more lesions correspond to one or more segments of a vessel where plaque is present, the one or more lesions;
identify one or more lesions in the multiplanar reconstruction;
identify plaque in the one or more lesions based at least in part on applying a trained machine learning algorithm to the multiplanar reconstruction;
determine a lesion for treatment from the one or more lesions, wherein to determine the lesion for treatment, the system is configured to:
generate a graphical user interface comprising the multiplanar reconstruction; and
receive via the graphical user interface a user selection of a lesion of the one or more lesions;
determine a density of the plaque present in the lesion corresponding to the user selection based at least in part on analyzing radiodensities of image pixels of the multiplanar reconstruction;
preoperatively determine a stenting procedure for the lesion corresponding to the user selection based at least in part on the determined density of the plaque, wherein the stenting procedure comprises one or more of angioplasty or atherectomy;
preoperatively determine, based at least in part on a normal lumen diameter, a diameter for a stent, wherein the normal lumen diameter is obtained from a segment of the vessel adjacent to the lesion corresponding to the user selection;
preoperatively determine, based on a length of the lesion, a length of the stent, wherein the length of the lesion is determined along an axis generally parallel to a centerline of the vessel, wherein the centerline of the vessel is determined based at least in part on applying the trained machine learning algorithm to the multiplanar reconstruction;
preoperatively determine, based on a location of the lesion, a location for placement of the stent, wherein the location is determined relative to a reference point along the vessel, the reference point comprising one or more of an ostium, bifurcation point, or trifurcation point defined by a morphology of the vessel;
preoperatively generate a surgical plan comprising stenting procedure,
the diameter of the stent, the length of the stent, and the location for placement of the stent; and
preoperatively cause generation of an updated graphical user interface showing the preoperatively generated surgical plan to preoperatively aid stent selection and surgical planning for coronary revascularization.

11. The system of claim 10, wherein the graphical user interface further comprises data related to the one or more lesions, wherein the data related to the one or more lesions comprises at least one of: a maximum diameter stenosis, a minimum luminal diameter stenosis, a plaque length, a plaque volume, or a normal lumen diameter.

12. The system of claim 10, wherein the graphical user interface further comprises one or more markers, each marker positioned relative to the multiplanar reconstruction to indicate a location of a maximum diameter stenosis.

13. The system of claim 10, wherein the graphical user interface further comprises an indication of a likelihood of ischemia.

14. The system of claim 10, wherein the location for placement of the stent is measured relative to a reference point for the multiplanar reconstruction.

15. The system of claim 10, wherein the graphical user interface further comprises a user input configured to allow a user to select to perform an atherectomy on the selected lesion.

16. The system of claim 10, wherein the reference point comprises a left main trifurcation or a left main bifurcation.

17. The system of claim 10, wherein the surgical plan is a robotic surgery plan, wherein the robotic surgery plan comprises instructions for controlling movement of a surgical robot.

18. The system of claim 10, wherein the instructions are further configured to cause the system to:
receive coronary data, wherein the coronary data comprises at least one of:

optical coherence tomography data, near field infrared spectroscopy data, ultrasound data, or invasive angiography data, wherein the surgical plan is preoperatively generated further based at least in part on the coronary data.

* * * * *